US008524745B2

(12) United States Patent
Yuan et al.

(10) Patent No.: US 8,524,745 B2
(45) Date of Patent: Sep. 3, 2013

(54) BENZISOTHIAZOL-3(1H)-ONE-5-SULFONYL DERIVATIVES AS CHEMOKINE RECEPTOR MODULATORS

(71) Applicant: Allergan, Inc., Irvine, CA (US)

(72) Inventors: Haiqing Yuan, Irvine, CA (US); Richard L. Beard, Newport Beach, CA (US); Xiaoxia Liu, Lake Forest, CA (US); John E. Donello, Dana Point, CA (US); Veena Viswanath, Irvine, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 13/710,697

(22) Filed: Dec. 11, 2012

(65) Prior Publication Data
US 2013/0150413 A1 Jun. 13, 2013

Related U.S. Application Data

(60) Provisional application No. 61/569,323, filed on Dec. 12, 2011.

(51) Int. Cl.
  *C07D 417/12* (2006.01)
  *C07D 417/14* (2006.01)
  *C07D 275/04* (2006.01)
  *C07D 275/06* (2006.01)
  *A61K 31/428* (2006.01)

(52) U.S. Cl.
  USPC ........ 514/338; 514/373; 546/271.1; 548/207; 548/209; 548/213

(58) Field of Classification Search
  CPC ............................ C07D 275/04; C07D 275/06
  USPC ................................................. 548/207–214
  See application file for complete search history.

(56) References Cited

U.S. PATENT DOCUMENTS

| 7,504,424 B2 * | 3/2009 | Yu et al. ........................ 514/373 |
| 7,585,859 B2 | 9/2009 | Ibrahim |

FOREIGN PATENT DOCUMENTS

| JP | 57108016 A * | 7/1982 |
| JP | 1547077 | 2/1990 |
| WO | 2007014054 | 2/2007 |
| WO | 2007-067875 | 6/2007 |

OTHER PUBLICATIONS

Chen, J. et al. "A fragment-based approach for the discovery of isoform-specific p38α inhibitors." A.C.S. Chem. Biol. 2007, 2, 329-336.*
Taha, M. O. et al. "Combining ligand-based pharmacaphore modeling, quantitative structure-activity realtionsip analysis and in silico screening for the discovery of new potent hormome sensitive lipase inhibitors." J. Med. Chem. 2008, 51, 6478-6494.*
Kharul, R. K. et al. "Effective Synthesis of 1,5-Disubstituted 2,1-Benzisothiazol-3(1H)-ones." Synth. Commun. 2011, 41, 3265-3279.*
Albert, Anthony et al, The Synthesis and Reactions of Certain 3-Substituted-2,1-Benzisothiazoles, J. Heterocyclic Chem., Jun. 1978, 529-536, 15.
Ambati, Jayakrishna et al, An Animal Model of Age-Related Macular Degeneration in Senescent Ccl-2- or Ccr-2Deficient Mice, Nature Medicine, 2003, 1390-1397, 9.
Beech, John et al, Neuroprotection in Ischemia—Reperfusion Injury: An Antiinflammatory Approach Using a Novel Broad-Spectrum Chemokine Inhibitor, Journal of Cerebral Blood Flow and Metabolism, 2001, 683-689, 21.
Cross, L.C. et al, Rules for the Nomenclature of Organic Chemistry, Section E: Stereochemistry, Pure & Appl. Chem., 1976, 11-30, 45.
Fang, I-MO et al, Expression of chemokine and receptors in Lewis rats with experimental autoimmune anterior uveitis, Experimental Eye Research, 2004, 1043-1055, 78, US.
Feria, Manuel et al, The CCR2 Receptor as a Therapeutic Target, Expert Opin. Ther Patents, 2006, 49-57, 16.
Gerard, Craig et al, Chemokines and Disease, nature immunology, Chemokine Reviews, 2001, 108-115, 2, Nature Publishing Group.
Grainger, David et al, Broad-Spectrum Chemokine Inhibitors (BSCIs) and Their Anti-Inflammatory Effects in Vivo, Biochemical Pharmacology, 2003, 1027-1034, 65.
Keino, Kiroshi et al, Chemokine and Chemokine Receptor Expression During Experimental Autoimmune Uveoretinitis in Mice, Graefe's Arch Clin Exp Ophthalmol, 2003, 111-115, 241.
Klitgaard, Torben et al, Chemokine Receptors and Early Activation Markers in Acute Anterior Uveitis, Acta Ophthalmol. Scand., 2004, 179-183, 82.
Meleth, Annal et al, Serum Inflammatory Makers in Diabetic Retinopathy, Investigative Ophthalmology & Visual Science, Nov. 2005, 4295-4301, 46.
Peace, Simon et al, Identification of a Sulfonamide Series of CCR2 Antagonists, Bioorganic & Medicinal Chemistry Letters, 2010, 3961-3964, 20.
Reckless, Jill et al, Identification of Oligopeptide Sequences Which Inhibit Migration Induced by a Wide Range of Chemokines, Biochem. J., 1999, 803-811, 340, GB.
Stahl, Heinrich et al, Handbook of Pharmaceutical Salts, Verlag Helvetica Chimica Acta—Zurich, 2002, 329-345.
Takeuchi, Aya et al, CCR5-Deficient Mice Develop Experimental Autoimmune Uveoretinitis in the Context of a Deviant Effector Response, Investigative Ophthalmology & Visual Science, Oct. 2005, 3753-3760, 46, US.
Tokuyama, Hirotake et al, The Simultaneous Blockage of Chemokine Receptors CCR2, CCR5 and CXCR3 by a Non-peptide Chemokine Receptor Antagonist protects Mice From Dextran Sodium Sulfate-Mediated Colitis, International Immunology, 2005, 1023-1034, 17, US.
Tuaillon, Nadine et al, MCP-1 Expression in Endotoxin-Induced Uveitis, Investigative Ophthalmology & Visual Science, May 2002, 1493-1498, 43.

(Continued)

*Primary Examiner* — Samantha Shterengarts
*Assistant Examiner* — Amanda L Aguirre
(74) *Attorney, Agent, or Firm* — Doina G. Ene

(57) ABSTRACT

The present invention relates to novel benzisothiazol-3(1H)-one-5-sulfonyl derivatives, processes for preparing them, pharmaceutical compositions containing them and their use as pharmaceuticals as modulators of chemokine receptors.

14 Claims, No Drawings

(56) References Cited

OTHER PUBLICATIONS

Wallace, Graham et al, The Role of Chemokines and Their Receptors in Ocular Disease, Progress in Retinal and Eye Research, 2004, 435-448, 23.

Weisberg, Stuart et al, CCR2 Modulates Inflammatory and Metabolic Effects of High-Fat Feeding, The Journal of Clinical Investigation, Jan. 2006, 115-124, 116.

Wells, Timothy et al, Chemokine Blockers—Therapeutics in the Making?, Trends in Pharmacological Sciences, Jan. 2006, 41-47, 27.

Yamagami, Satoru et al, CCR5 Chemokine Receptor Mediates Recruitment of MHC Class II-Positive Langerhans Cells in the Mouse Corneal Epithelium, Investigative Ophthalmology & Visual Science, Apr. 2005, 1201-1207, 46.

Yang, Chang-Hao et al, Effects of the NF-kB Inhibitor Pyrrolidine Dithiocarbamate on Experimentally Induced Autoimmune Anterior Uveitis, Investigative Ophthalmology & Visual Science, 2005, 1339-1347, 46.

Patent Cooperation Treaty, Notification of Transmittal of the International Search Report and the Written Opinion of the International Searching Authority, or the Declaration, Form PCT/ISA/220, Int. App. No. PCT/US2012/068873, Feb. 20, 2013.

* cited by examiner ns for monocytes and T-cells (Fang et al., 2004; Keino et al.,

BENZISOTHIAZOL-3(1H)-ONE-5-SULFONYL DERIVATIVES AS CHEMOKINE RECEPTOR MODULATORS

RELATED APPLICATION

This application claims the benefit of U.S. Provisional Application Ser. No. 61/569,323, filed Dec. 12, 2011, which is incorporated herein by reference in its entirety.

FIELD OF THE INVENTION

The present invention relates to novel benzisothiazol-3 (1H)-one-5-sulfonyl derivatives, processes for preparing them, pharmaceutical compositions containing them and their use as pharmaceuticals as modulators of chemokine receptors. The invention relates specifically to the use of these compounds and their pharmaceutical compositions to treat disorders associated with chemokine receptor (CCR) modulation.

BACKGROUND OF THE INVENTION

Chemokines are a group of 7- to 14-kd peptides that play an important role in orchestrating leukocyte recruitment and migration during inflammation, and therefore represent an important target for anti-inflammatory therapies (Wells et al., 2006). They act by binding to seven-transmembrane, G protein-coupled receptors, the chemokine receptors. The chemokine system is complex, with about ~50 chemokines and 20 chemokine receptors identified in humans, often acting with redundancy, making selection of specific antagonists difficult (Gerard and Rollins, 2001). Genetic knockout strategies have confirmed the importance of chemokines as regulators of immune function, but the deletion of specific chemokines has led to only specific and relatively mild defects in the inflammatory response further emphasizing the complex redundancy of the system. Selectivity is crucial for use of chemokine receptor antagonists in systemic diseases where a single chemokine-receptor system is implicated such as atheroscelorsis where the macrophage/monocyte system is the major player in order to allow a subtle and specific control over immune function (Weisberg et al., 2006; Feria and Diaz Gonzalez et al., 2006).

Many ocular conditions are characterized by inappropriate migration and infiltration of cells such as leukocytes and endothelial cells into the eye with deleterious effects to ocular structures (Wallace et al., 2004). Chemokines have been identified in such diseases and misregulation of the chemokine system is apparent in corneal graft rejection, diabetic retinopathy, age-related macular degeneration (ARMD), chronic inflammatory diseases such as uveitis, dry eye etc. Mice lacking CCR2 or MCP-1 develop features of ARMD with age, including drusen deposits, choroidal neovascularization and photoreceptor atrophy indicating a crucial role for this chemokine and its receptor signaling (Amabati et al., 2003). Thus CCR2 receptor-specific inhibitor might have potential therapeutic benefit in ocular diseases like ARMD. In contrast, various human and animal studies have identified several chemokines in different forms of uveitis, produced both by resident and infiltrating cells, that strongly suggests a prominent role for these molecules in its pathogenesis. Studies in rat and mice models of uveitis have demonstrated up-regulation of monocyte chemoattractant protein-1 (MCP-1), macrophage inflammatory protein-1 (MIP-1), RANTES, stromal derived factor-1 (SDF-1) which are powerful chemoattractants for monocytes and T-cells (Fang et al., 2004; Keino et al., 2003). Similar findings have been reported in peripheral blood mononuclear cells in patients with acute anterior uveitis (AAU), the most common form of human uveitis (Klitgaard et al., 2004). MCP-1 knockout mice and CCR5 knockout mice show reduced endotoxin-induced uveitis, which is the animal model for AAU (Takeuchi et al., 2005; Tuallion et al., 2002). It has also been demonstrated that blocking the chemokine system upstream with the use of NF-κB blockers significantly attenuates experimental AAU in rats (Yang et al., 2005). Blockage of NF-κB results in transcriptional inhibition of multiple chemokines. Given the complexity of pathogenesis in uveitis it is unlikely that a selective inhibition of a chemokine receptor in monotherapy will offer therapeutic benefit. A similar role of multiple chemokines have been shown to be correlated with clinical stage of disease in diabetic retinopathy and dry eye (Meleth et al., 2005; Yamagami et al., 2005). In these ocular diseases the use of broad spectrum chemokine receptor inhibitor which inhibits the function of a wide range of chemokines maybe beneficial.

The first broad spectrum chemokine inhibitor (BSCI) to be reported was termed Peptide 3, which was derived from the sequence of human chemokine MCP-1 and was shown to block the migration of monocytes in response to MCP-1, MIP-1, RANTES and SDF-1 (Reckless and Grainger. 1999). A cyclic retro inverse analogue of Peptide 3, constructed of D-amino acids in the reverse sequence, called NR58-3.14.3 was observed to be a more potent chemokine inhibitor (Beech et al., 2001). NR58-3.14.3 has been used to test for anti-inflammatory activities in animal models of atherosclerosis, lung inflammation, irritable bowel syndrome etc (Beech et al., 2001; Grainger and Reckless. 2003; Tokuyama et al., 2005). However there are several disadvantages to using these BSCI as a long-term therapeutic strategy. The known BSCIs which are peptides which have relatively low potency, poor pharmacokinetics, and are unstable in vivo. In addition, systemic use of broad spectrum chemokine receptor inhibitors could potentially lead to deleterious side effects due to their systemic anti-inflammatory activity. However in ocular diseases, a local or topical application would prevent the broad spectrum inhibitor to be taken up systemically. Identification of a small molecule inhibitor of several chemokine receptors could be very useful for treatment of inflammatory ocular diseases. Given the evidence for the role of multiple chemokines in several ocular diseases and these results, we propose that the use of small and large molecule broad spectrum chemokine receptor inhibitors will have utility in the local treatment of ocular inflammatory diseases including, but not limited to, uveitis, dry eye, diabetic retinopathy, allergic eye disease and proliferative retinopathies. Manipulation of multiple chemokines therefore represents a novel therapeutic approach in treating ocular diseases.

U.S. Pat. No. 7,585,859 discloses the preparation of thiophene and thiazole derivatives as PDE4B inhibitors.

JP 1547077 discloses anticoagulant formulations containing benzisothiazolinones. Journal of Heterocyclic Chemistry (1978), 15(4), 529-36 teaches the synthesis and reactions of certain 3-substituted-2,1-benzisothiazoles.

SUMMARY OF THE INVENTION

A group of novel benzisothiazol-3(1H)-one-5-sulfonyl derivatives, which are potent and selective chemokine receptor modulators has been discovered. As such, the compounds described herein are useful in treating a wide variety of disorders associated with modulation of chemokine receptors. The term "modulator" as used herein, includes but is not limited to: receptor agonist, antagonist, inverse agonist, inverse antagonist, partial agonist, partial antagonist.

This invention describes compounds of Formula I, which have chemokine receptor biological activity. The compounds in accordance with the present invention are thus of use in medicine, for example in the treatment of humans with diseases and conditions that are alleviated by CCR modulation.

In one aspect, the invention provides a compound represented by Formula I, stereoisomeric forms, individual enantiomers, individual diastereoisomers, individual tautomers or a pharmaceutically acceptable salt thereof:

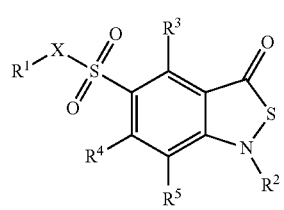

Formula I wherein:

$R^1$ is substituted or unsubstituted $C_{1-10}$ alkyl, substituted or unsubstituted heterocycle, substituted or unsubstituted $C_{3-10}$ cycloalkyl, substituted or unsubstituted $C_{3-10}$ cycloalkenyl or substituted or unsubstituted $C_{6-10}$ aryl;

$R^2$ is substituted or unsubstituted $C_{1-6}$ alkyl;

$R^3$ is hydrogen, substituted or unsubstituted $C_{1-6}$ alkyl, halogen, substituted or unsubstituted $-OC_{1-3}$ alkyl, CN, $NO_2$, $C_{2-6}$ alkenyl, $C_{2-6}$ alkynyl, $C(O)R^6$, $NR^7R^8$ or hydroxyl;

$R^4$ is hydrogen, substituted or unsubstituted $C_{1-6}$ alkyl, halogen, substituted or unsubstituted $-OC_{1-3}$ alkyl, CN, $NO_2$, $C_{2-6}$ alkenyl, $C_{2-6}$ alkynyl, $C(O)R^6$, $NR^7R^8$ or hydroxyl;

$R^5$ is hydrogen, substituted or unsubstituted $C_{1-6}$ alkyl, halogen, substituted or unsubstituted $-OC_{1-3}$ alkyl, CN, $NO_2$, $C_{2-6}$ alkenyl, $C_{2-6}$ alkynyl, $C(O)R^6$, $NR^7R^8$ or hydroxyl;

X is O, S or NH;

$R^6$ is hydrogen or substituted or unsubstituted $C_{1-6}$ alkyl;

$R^7$ is hydrogen or substituted or unsubstituted $C_{1-6}$ alkyl;

$R^8$ is hydrogen or substituted or unsubstituted $C_{1-6}$ alkyl;

with the proviso that the compound of Formula I is not one of the following compounds:

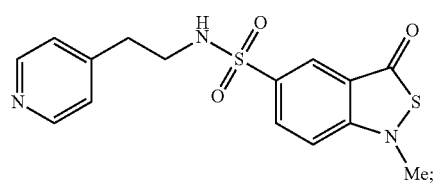

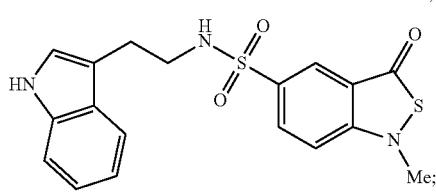

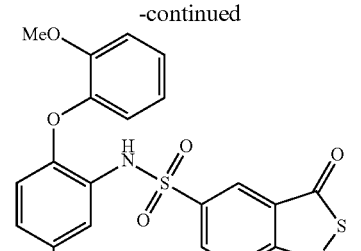

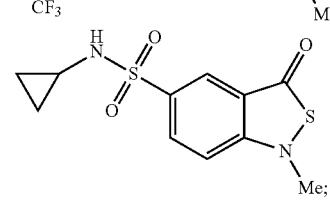

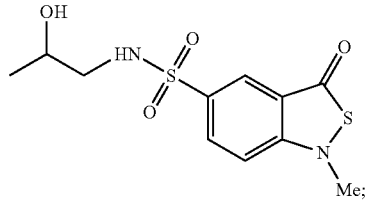

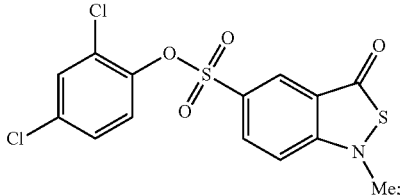

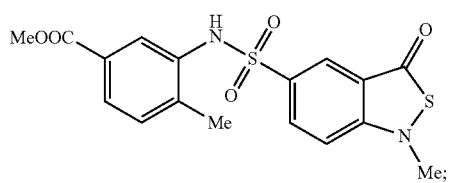

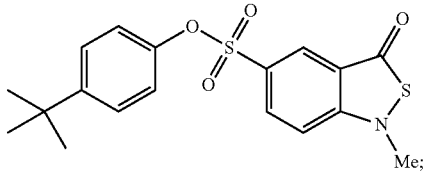

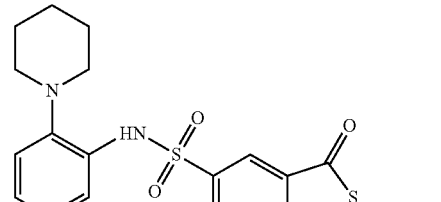 or

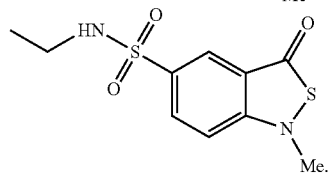

In another aspect, the invention provides a compound represented by Formula I, wherein:

$R^1$ is substituted or unsubstituted $C_{1-10}$ alkyl, substituted or unsubstituted heterocycle, or substituted or unsubstituted $C_{6-10}$ aryl;

$R^2$ is unsubstituted $C_{1-6}$ alkyl;

$R^3$ is hydrogen, substituted or unsubstituted $C_{1-6}$ alkyl, halogen;

$R^4$ is hydrogen, substituted or unsubstituted $C_{1-6}$ alkyl, halogen;

$R^5$ is hydrogen, substituted or unsubstituted $C_{1-6}$ alkyl, halogen;

X is O or NH;

with the proviso that the compound of Formula I is not one of the following compounds:

In another aspect, the invention provides a compound represented by Formula I, wherein:

$R^1$ is substituted or unsubstituted $C_{1-10}$ alkyl;
$R^2$ is unsubstituted $C_{1-6}$ alkyl;
$R^3$ is hydrogen;
$R^4$ is hydrogen;
$R^5$ is hydrogen;
X is NH;

with the proviso that the compound of Formula I is not one of the following compounds:

In another aspect, the invention provides a compound represented by Formula I, wherein:
R¹ is substituted or unsubstituted heterocycle,
R² is unsubstituted $C_{1-6}$ alkyl;
R³ is hydrogen;
R⁴ is hydrogen;
R⁵ is hydrogen; and
X is NH.

In another aspect, the invention provides a compound represented by Formula I, wherein:
R¹ is substituted or unsubstituted $C_{6-10}$ aryl;
R² is unsubstituted $C_{1-6}$ alkyl;
R³ is hydrogen;
R⁴ is hydrogen;
R⁵ is hydrogen;
X is O or NH;
with the proviso that the compound of Formula I is not one of the following compounds:

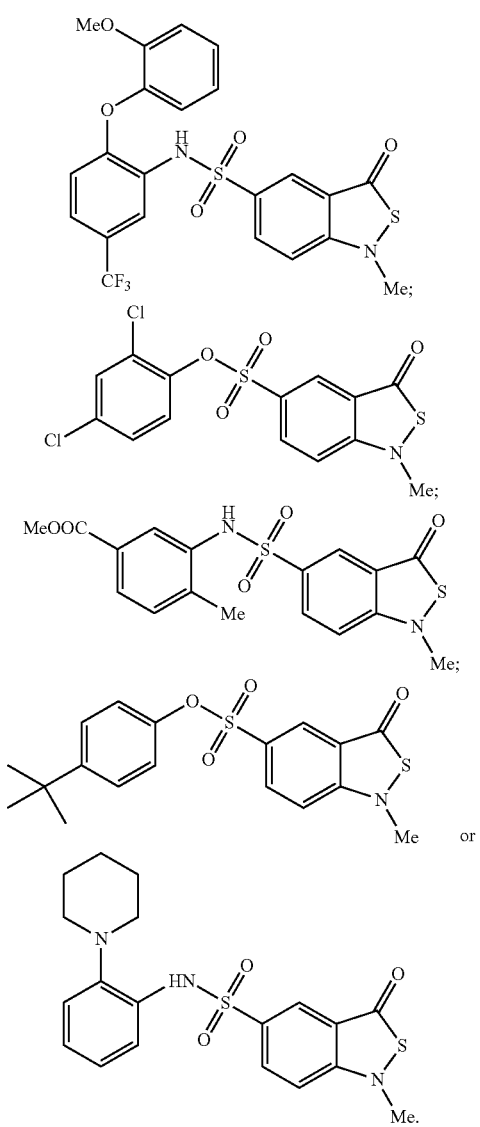

In another aspect, the invention provides a compound represented by Formula I, wherein:
R¹ is substituted or unsubstituted $C_{6-10}$ aryl;
R² is unsubstituted $C_{1-6}$ alkyl;

R³ is hydrogen;
R⁴ is hydrogen;
R⁵ is hydrogen;
X is O;
with the proviso that the compound of Formula I is not one of the following compounds:

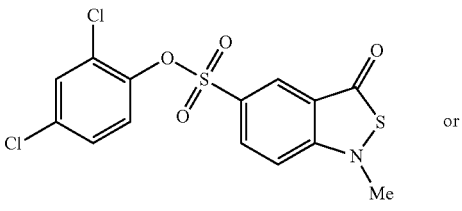

In another aspect, the invention provides a compound represented by Formula I, wherein:
R¹ is substituted or unsubstituted $C_{6-10}$ aryl;
R² is unsubstituted $C_{1-6}$ alkyl;
R³ is hydrogen;
R⁴ is hydrogen;
R⁵ is hydrogen;
X is NH;
with the proviso that the compound of Formula I is not one of the following compounds:

In another aspect, the invention provides a compound represented by Formula I, wherein:
$R^1$ is substituted or unsubstituted $C_{3-10}$ cycloalkyl;
$R^2$ is unsubstituted $C_{1-6}$ alkyl;
$R^3$ is hydrogen,
$R^4$ is hydrogen,
$R^5$ is hydrogen;
X is NH;
with the proviso that the compound of Formula I is not the following compound:

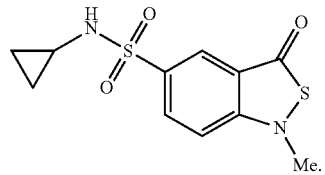 [SMILES: Cn1sc(=O)c2cc(S(=O)(=O)NC3CC3)ccc21]

The term "alkyl", as used herein, refers to saturated, monovalent or divalent hydrocarbon moieties having linear or branched moieties or combinations thereof and containing 1 to 10 carbon atoms. One methylene (—$CH_2$—) group, of the alkyl can be replaced by oxygen, sulfur, sulfoxide, nitrogen, carbonyl, carboxyl, sulfonyl, or by a divalent $C_{3-6}$ cycloalkyl. Hydrogen atoms on alkyl groups can be substituted by groups including, but not limited to: halogens, —OH, $C_{3-8}$ cycloalkyl, non-aromatic heterocycles, aromatic heterocycles, —$OC_{1-6}$ alkyl, —$NH_2$, —$NO_2$, amides, ethers, esters, aldehydes, sulfonamides groups, aryl, carboxylic acid, ketones, amides, phosphonic acid groups, sulphonic acid groups, phosphoric acid.

The term "cycloalkyl", as used herein, refers to a monovalent or divalent group of 3 to 10 carbon atoms, derived from a saturated cyclic hydrocarbon. Cycloalkyl groups can be monocyclic or polycyclic. Cycloalkyl can be substituted by groups including, but not limited to: halogens, —OH, $C_{3-8}$ cycloalkyl, non-aromatic heterocycles, aromatic heterocycles, —$OC_{1-6}$ alkyl, —$NH_2$, —$NO_2$, amides, ethers, esters, ketones, aldehydes, sulfonamides groups, aryl, carboxylic acid, amides, phosphonic acid groups, sulphonic acid groups, phosphoric acid.

The term "cycloalkenyl", as used herein, refers to a monovalent or divalent group of 3 to 10 carbon atoms, derived from a saturated cycloalkyl having one double bond. Cycloalkenyl groups can be monocyclic or polycyclic. Cycloalkenyl groups can be substituted by groups including, but not limited to: halogens, —OH, $C_{3-8}$ cycloalkyl, non-aromatic heterocycles, aromatic heterocycles, —$OC_{1-6}$ alkyl, —$NH_2$, —$NO_2$, amides, ethers, ketones, esters, aldehydes, sulfonamides groups, aryl, carboxylic acid, amides, phosphonic acid groups, sulphonic acid groups, phosphoric acid.

The term "halogen", as used herein, refers to an atom of chlorine, bromine, fluorine, iodine.

The term "alkenyl", as used herein, refers to a monovalent or divalent hydrocarbon radical having 2 to 6 carbon atoms, derived from a saturated alkyl, having at least one double bond. $C_{2-6}$ alkenyl can be in the E or Z configuration. Alkenyl groups can be substituted by groups including, but not limited to: halogens, —OH, $C_{3-8}$ cycloalkyl, non-aromatic heterocycles, aromatic heterocycles, —$OC_{1-6}$ alkyl, —$NH_2$, —$NO_2$, amides, ethers, esters, aldehydes, sulfonamides groups, aryl, carboxylic acid, ketones, amides, phosphonic acid groups, sulphonic acid groups, phosphoric acid The term "alkynyl", as used herein, refers to a monovalent or divalent hydrocarbon radical having 2 to 6 carbon atoms, derived from a saturated alkyl, having at least one triple bond.

The term "heterocycle" as used herein, refers to a 3 to 14 membered ring, which can be aromatic or non-aromatic, saturated or non-saturated, containing at least one heteroatom selected from O or N or S or combinations of at least two thereof, interrupting the carbocyclic ring structure. The heterocyclic ring can be interrupted by a C=O; the S heteroatom can be oxidized. Heterocycles can be monocyclic or polycyclic. Heterocyclic ring moieties can be substituted by groups including, but not limited to: halogens, —OH, $C_{3-8}$ cycloalkyl, non-aromatic heterocycles, aromatic heterocycles, —$OC_{1-6}$ alkyl, —$NH_2$, —$NO_2$, amides, ethers, esters, ketones, aldehydes, sulfonamides groups, aryl, carboxylic acid, amides, phosphonic acid groups, sulphonic acid groups, phosphoric acid.

Usually, in the present case, heterocyclic groups are pyridine, furan, azetidine, thiazole, thiophene, oxazole, pyrazole, benzofuran, methyl-benzofuran, isoxazole, 2-oxoindoline, 2-oxo-2,3-dihydro-1,3-benzoxazole, 2-oxo-2H-chromene, imidazole[2,1-b]thiazole, 1-H-pyrazole, indole, imidazole, quinoline, 1-H-indazole The term "aryl" as used herein, refers to an organic moiety derived from an aromatic hydrocarbon consisting of a ring containing 6 to 10 carbon atoms by removal of one hydrogen. Aryl can be substituted by groups including, but not limited to: halogens, —OH, $C_{3-8}$ cycloalkyl, non-aromatic heterocycles, aromatic heterocycles, —$OC_{1-6}$ alkyl, —$NH_2$, —$NO_2$, amides, ethers, esters, aldehydes, sulfonamides groups, aryl, carboxylic acid, ketones, amides, phosphonic acid groups, sulphonic acid groups, phosphoric acid. Aryl can be monocyclic or bicyclic.

The term "hydroxyl" as used herein, represents a group of formula "—OH".

The term "carbonyl" as used herein, represents a group of formula "—C(O)".

The term "carboxyl" as used herein, represents a group of formula "—C(O)O—".

The term "sulfonyl" as used herein, represents a group of formula "—$SO_2$".

The term "sulfate" as used herein, represents a group of formula "—O—S(O)$_2$—O—".

The term "carboxylic acid" as used herein, represents a group of formula "—C(O)OH".

The term "sulfoxide" as used herein, represents a group of formula "—S=O".

The term "phosphonic acid" as used herein, represents a group of formula "—P(O)(OH)$_2$".

The term "phosphoric acid" as used herein, represents a group of formula "—(O)P(O)(OH)$_2$".

The term "sulphonic acid" as used herein, represents a group of formula "—S(O)$_2$OH".

The formula "H", as used herein, represents a hydrogen atom.

The formula "O", as used herein, represents an oxygen atom.

The formula "N", as used herein, represents a nitrogen atom.

The formula "S", as used herein, represents a sulfur atom.

The term "amine" as used herein, represents a group of formula "—$NR^xR^y$", wherein $R^x$ and $R^y$ can be the same or independently H, alkyl, aryl, cycloalkyl, cycloalkenyl, heterocycle as defined above.

The term "amide" as used herein, represents a group of formula "—C(O)$NR^xR^y$," or "—C(O)N($R^x$)($R^Y$)" or "$NR^xC$ (O)R^y''' wherein R^x and R^y can be the same or independently H, alkyl, aryl, cycloalkyl, cycloalkenyl, heterocycle as defined above.

The term "sulfonamide" as used herein, represents a group of formula "—S(O)$_2$NR$^x$R$^y$'" or "NR$^x$R$^y$S(O)$_2$" or "—NR$^x$S(O)$_2$R$^y$'" wherein R$^x$ and R$^y$ can be the same or independently H, alkyl, aryl, cycloalkyl, cycloalkenyl, heterocycle as defined above.

The term "ester" as used herein, represents a group of formula "—C(O)O(R$^x$)", wherein Rx is alkyl, aryl, cycloalkyl, cycloalkenyl, heterocycle as defined above.

The term "aldehyde" as used herein, represents a group of formula "—C(O)H".

The term "ketone" as used herein, represents a group of formula "—C(O)(R$^x$)", wherein R$^x$ is alkyl, aryl, cycloalkyl, cycloalkenyl, heterocycle as defined above.

Usually R$^1$ is substituted or unsubstituted C$_{1-10}$ alkyl, substituted or unsubstituted heterocycle, substituted or unsubstituted C$_{3-10}$ cycloalkyl, substituted or unsubstituted C$_{3-10}$ cycloalkenyl or substituted or unsubstituted C$_{6-10}$ aryl. Preferred R$^1$ is substituted or unsubstituted C$_{6-10}$ aryl, substituted or unsubstituted C$_{1-10}$ alkyl, substituted or unsubstituted heterocycle, substituted or unsubstituted C$_{3-10}$ cycloalkyl. More preferred R$^1$ is 2,4-dichlorophenyl, methyl 4-methyl-3-benzoate, N,N-dimethyl-N-benzyl-tetrahydro-2H-pyran-4-aminium, 3-(1H-tetrazol-5-yl)phenyl, 2-benzamide, 5-chloro-2-benzamide, 2-methyl-phenyl, 2-aminophenyl, 2-(hydroxymethyl)phenyl, 5-fluoro-2-methylphenyl, 4-fluoro-2-methylphenyl, 1H-indol-4-yl, 2-acetylphenyl, 2-(propan-2-yl)phenyl, 4-methoxy-2-methylphenyl, 2-methoxy-5-methylphenyl, 5-(hydroxymethyl)-2-methylphenyl, 5-methoxy-2-methylphenyl, 2-(methylsulfanyl)phenyl, 5-chloro-2-methylphenyl, 4-chloro-2-methylphenyl, 2-amino-4-chlorophenyl, 2-amino-5-chlorophenyl, 2-methyl-1-benzofuran-7-yl, 5,6,7,8-tetrahydronaphthalen-1-yl, N-methyl-2-benzamide, N-(2-phenyl)acetamide, methyl-2-benzoate, 2,5-dimethoxyphenyl, 3-chloro-2-methoxyphenyl, 4-chloro-2-(hydroxymethyl)phenyl, 2-(1H-pyrrol-1-yl)phenyl, 7-methylquinolin-8-yl, 2-amino-4-chlorophenyl, 2-(1H-tetrazol-1-yl)phenyl, 2-(pyrrolidin-1-yl)phenyl, methyl 3-methyl-4-benzoate, biphenyl-2-yl, 5-methyl-2-(1H-pyrrol-1-yl)phenyl, 5-chloro-2-(methylsulfanyl)phenyl, 2,4-dichloro-6-methylphenyl, 1-acetyl-2,3-dihydro-1H-indol-7-yl, 2-(2-oxopyrrolidin-1-yl)phenyl, 2-(piperidin-1-yl)phenyl, 2-(trifluoromethoxy)phenyl, 5-oxo-2,3,4,5-tetrahydro-1H-1,4-benzodiazepin-9-yl, 2-(morpholin-4-yl)phenyl, 2-benzylphenyl, 2-(phenylamino)phenyl, 2-phenoxyphenyl, 2-(pyridin-3-yloxy)phenyl, 5-methoxy-2-(1H-pyrrol-1-yl)phenyl, 2-(cyclohexylamino)phenyl, 2-(4-methylpiperazin-1-yl)phenyl, N-tert-butyl-2-benzamide, 2-(tetrahydrofuran-2-ylmethoxy)phenyl, 2-(phenylcarbonyl)phenyl, 2-(benzylamino)phenyl, 2-(2-methylphenoxy)phenyl, 2-(4-methylphenoxy)phenyl, 2-(benzyloxy)phenyl, 2-(3-methylphenoxy)phenyl, 2-(2-aminophenoxy)phenyl, 2-(pyridin-2-ylmethoxy)phenyl, 2-(phenylsulfanyl)phenyl, 2-(1H-benzimidazol-2-yl)phenyl, 9-oxo-9,10-dihydroacridin-4-yl, N-phenylbenzamide, 2-methoxy-5-phenoxyphenyl, N-cyclohexyl-2-benzamide, 5-acetyl-2-(piperidin-1-yl)phenyl, cyclohexyl(methyl)amino]methyl}phenyl, 2-[(4-chlorophenyl)amino]phenyl, 5-chloro-2-phenoxyphenyl, 5-acetyl-2-(morpholin-4-yl)phenyl, 2,4-dimethoxy-5-(trifluoromethyl)phenyl, 2,2,3,3-tetrafluoro-2,3-dihydro-1,4-benzodioxin-5-yl, 5-cyano-2-(phenylsulfanyl)phenyl, 2-(1,3-benzothiazol-2-yl)phenyl, benzyl 2 benzoate, 2-(pyrrolidin-1-yl)-5-(trifluoromethyl)phenyl, 4-chloro-2-(phenylcarbonyl)phenyl, 4-chlorophenyl)carbonyl]phenyl, 2-(phenylsulfonyl)phenyl, -[5-chloro-2-(3-methylphenoxy)phenyl, 2-(2-methoxyethoxy)-5-(trifluoromethyl)phenyl, 5-cyano-2-[(4-methylphenyl)sulfanyl]phenyl, 2-phenylethyl2benzoate, benzyl phenyl)carbamate, 2-(piperidin-1-yl)-5-(trifluoromethyl)phenyl, 4'-amino-3,3'-dimethoxybiphenyl-4-yl, -[2-(morpholin-4-yl)-5-(trifluoromethyl)phenyl, methyl 3 thiophene-2-carboxylate, 5-chloro-2-(4-chlorophenoxy)phenyl, 2-[(thiophen-2-ylsulfonyl)amino]phenyl, 2-{[(4-methylphenyl)sulfonyl]amino}phenyl, 4-fluorophenyl)sulfonyl]amino}phenyl, 2-chloro-6-fluorobenzyl)sulfanyl]phenyl, 2-[cyclohexyl(methyl)sulfamoyl]phenyl, 2-[ethyl(phenyl)sulfamoyl]phenyl, tert-butyl 4-(phenyl)piperazine-1-carboxylate, 2-(4-cyanophenoxy)-5-(trifluoromethyl)phenyl, phenyl)-4-(trifluoromethyl)benzamide, 2-[(1-benzylpiperidin-4-yl)amino]phenyl, 2-[(5-bromopyrimidin-2-yl)sulfanyl]phenyl, -[2-(2-methoxyphenoxy)-5-(trifluoromethyl)phenyl, 2-(4-methoxyphenoxy)-5-(trifluoromethyl)phenyl, 2-{[3-chloro-5-(trifluoromethyl)pyridin-2-yl]oxy}phenyl, 2-(4-ethoxyphenoxy)-5-(trifluoromethyl)phenyl, 2-(4-chloro-3,5-dimethylphenoxy)-5-(trifluoromethyl)phenyl, 3-(hydroxymethyl)phenyl, 2,4-difluorophenyl, 1H-indol-5-yl, 1H-benzimidazol-2-yl, 1H-indazol-5-yl, 2,3-dihydro-1H-inden-2-yl, 2,3-dihydro-1H-inden-4-yl, naphthalen-1-yl, naphthalen-2-yl, quinolin-3-yl, quinolin-8-yl, isoquinolin-5-yl, 2,3-dihydro-1,4-benzodioxin-6-yl, 1H-imidazol-1-yl) phenyl, 1H-imidazol-1-yl)phenyl, 3-(thiophen-2-yl)-1H-pyrazol-5-yl, biphenyl-4-yl, biphenyl-3-yl, 4-cyclohexylphenyl, 4-(morpholin-4-yl)phenyl, 5-chloro-2-[(4-oxopiperidin-1-yl)carbonyl]pyridin-3-yl, N,N-dimethyltetrahydro-2H-pyran-4-aminium, 2,3-dimethoxyphenyl, 2,3-dihydro-1,4-benzodioxin-5-yl, propan-2-yl)-N-{2-[(thiophen-2-ylsulfonyl)amino]phenyl, 2,2-difluoro-1,3-benzodioxol-4-yl, 2-[(thiophen-2-ylsulfonyl)amino]pyridin-3-yl, 5-chloro-2-[(thiophen-2-ylsulfonyl)amino]phenyl, 4-chloro-2-[(thiophen-2-ylsulfonyl)amino]phenyl, 1,3-benzodioxol-4-yl, 4-chloro-3-(trifluoromethyl)phenyl]sulfonyl}amino)phenyl, 4,5-dichloro-2-[(thiophen-2-ylsulfonyl)amino]phenyl, 5-chloro-2-[(thiophen-2-ylsulfonyl)amino, 3-(trifluoromethoxy)phenyl, oxanthren-1-yl, 7-chloro-2,3-dihydro-1,4-benzodioxin-5-yl, 2-{[(5-chlorothiophen-2-yl)sulfonyl]amino}phenyl, 2-{[(4,5-dichlorothiophen-2-yl)sulfonyl]amino}phenyl, 2-[(phenylsulfonyl)amino]phenyl, 2-{[(4-chlorophenyl)sulfonyl]amino}phenyl, 2-[(furan-2-ylsulfonyl)amino]phenyl, 5-bromo-2-[(thiophen-2-ylsulfonyl)amino]phenyl, 2-[(thiophen-2-ylsulfonyl)amino]-5-(trifluoromethyl)phenyl, 2{[(1-methyl-1H-imidazol-4-yl)sulfonyl]amino}phenyl, 2-{[(1-methyl-1H-pyrazol-3-yl)sulfonyl]amino}phenyl, 4-methyl-2-[(thiophen-2-ylsulfonyl)amino]phenyl thiophen-2-ylsulfonyl)amino]-5-(trifluoromethyl)phenyl, 5-methoxy-2-[(thiophen-2-ylsulfonyl)amino]phenyl, 2-[(pyridin-3-ylsulfonyl)amino]phenyl, 2-[(4H-1,2,4-triazol-3-ylsulfonyl)amino]phenyl, 1H-imidazol-4-ylsulfonyl)amino]phenyl, 2-{[(3,4-dichlorophenyl)sulfonyl]amino}phenyl, 2-{[(2,5-dichlorophenyl)sulfonyl]amino}phenyl, 2-{[(2-chlorophenyl)sulfonyl]amino}phenyl, 2-{[(2-fluorophenyl)sulfonyl]amino}phenyl, 2-({[3,5-bis(trifluoromethyl)phenyl]sulfonyl}amino)phenyl, 5-methyl-2-[(thiophen-2-ylsulfonyl)amino]phenyl, 2-fluoro-6-[(thiophen-2-ylsulfonyl)amino]phenyl, 5-cyano-2-[(thiophen-2-ylsulfonyl)amino]phenyl, 5-chloro-2-({[4-chloro-3-(trifluoromethyl)phenyl]sulfonyl}amino)phenyl, methyl 3-4-[(thiophen-2-ylsulfonyl)amino]benzoate, 2-({[4-(trifluoromethyl)phenyl]sulfonyl}amino)phenyl, 2-[(furan-3-ylsulfonyl)amino]phenyl, 2-({[3-(trifluoromethyl)phenyl]sulfonyl}amino)phenyl, 3,5-dichlorophenyl)sulfonyl]amino}phenyl, 3,5-difluorophenyl)sulfonyl]amino}phenyl, 2-{[(3-fluorophenyl)sulfonyl]amino}phenyl, 2-{[(4-methoxyphenyl)sulfonyl]amino}phenyl, 5-chloro-2-{[(3-chlorophenyl)sulfonyl]amino}phenyl, 5-chloro-2-{[(3,4-dichlorophenyl)sulfonyl]amino}phenyl, 4-methoxy-2-[(thiophen-2-ylsulfonyl)amino]phenyl, 4-cyano-2-[(thiophen-2-ylsulfonyl)amino]phenyl, methyl 4-3-[(thiophen-2-ylsulfonyl)amino]benzoate, 5-chloro-2-{[(3,5-dichlorophenyl)sulfonyl]amino}phenyl, 5-chloro-2-{[(3-methoxyphenyl)sulfonyl]amino}phenyl, 5-chloro-2-{[(5-methylthiophen-2-yl)sulfonyl]amino}phenyl, 5-chloro-2-{[(4-methoxyphenyl)sulfonyl]amino}phenyl, 5-chloro-2-{[(3,4-dimethoxyphenyl)sulfonyl]amino}phenyl, 5-(propan-2-yl)-2-[(thiophen-2-ylsulfonyl)amino]phenyl, 4-(propan-2-yl)-2-[(thiophen-2-ylsulfonyl)amino]phenyl, 5-chloro-2-{[(4-methylphenyl)sulfonyl]amino}phenyl, 5-chloro-2-{[(4-hydroxyphenyl)sulfonyl]amino}phenyl, 5-chloro-4-methyl-2-[(thiophen-2-ylsulfonyl)amino]phenyl, 4-chloro-5-methyl-2-[(thiophen-2-ylsulfonyl)amino]phenyl, 5-chloro-2-({[4-(dimethylamino)phenyl]sulfonyl}amino)phenyl, 5-(dimethylamino)-2-[(thiophen-2-ylsulfonyl)amino]phenyl, 4-(dimethylamino)-2-[(thiophen-2-ylsulfonyl)amino]phenyl, 5-chloro-2-({[4-(propan-2-yl)phenyl]sulfonyl}amino)phenyl, 5-chloro-2-[(thiophen-2-ylsulfonyl)amino]phenyl, 5-chloro-2-{[(2-methoxyphenyl)sulfonyl]amino}phenyl, 4-chloro-2phenyl)sulfamoyl]phenyl}acetamide, 4-chloro-2 phenyl)-4-methoxybenzamide, -[5-chloro-2-({[3-(dimethylamino)phenyl]sulfonyl}amino)phenyl, 3-[(thiophen-2-ylsulfonyl)amino]naphthalen-2-yl, 5-ethyl-2-[(thiophen-2-ylsulfonyl)amino]phenyl, 1R,2R)-2-[(thiophen-2-ylsulfonyl)amino]cyclohexyl, 5-{[4-(thiophen-2-ylsulfonyl)-3,4-dihydroquinoxalin-1(2H)-yl]sulfonyl, 5-chloro-2-{[(4-ethoxyphenyl)sulfonyl]amino}phenyl, 5-chloro-2-({[4-(propan-2-yloxy)phenyl]sulfonyl}amino)phenyl, 5-chloro-2-[(thiophen-2-ylmethyl)amino]phenyl, 5-chloro-2-{[(2,4-dimethoxyphenyl)sulfonyl]amino}phenyl, 4,5-dichloro-2-{[(4-methoxyphenyl)sulfonyl]amino}phenyl, 1R,2S)-2-[(thiophen-2-ylsulfonyl)amino]cyclohexyl, 5-dichloro-2-{[(3-methoxyphenyl)sulfonyl]amino}phenyl, 2-chloro-6-[(thiophen-2-ylsulfonyl)amino]phenyl, 4,5-dichloro-2-{[(4,5-dichlorothiophen-2-yl)sulfonyl]amino}phenyl, 4,5-dichloro-2-({[4-chloro-3-(trifluoromethyl)phenyl]sulfonyl}amino)phenyl, 4,5-dichloro-2-{[(5-methylthiophen-2-yl)sulfonyl]amino}phenyl, 3-[(thiophen-2-ylsulfonyl)amino]phenyl, 2-methyl-1-[(thiophen-2-ylsulfonyl)amino]propan-2-yl, 3-methyl-2-[(thiophen-2-ylsulfonyl)amino]phenyl, 3-chloro-2-[(thiophen-2-ylsulfonyl)amino]phenyl, 2-methyl-2-[(thiophen-2-ylsulfonyl)amino]propyl, -{[(thiophen-2-ylsulfonyl)amino]methyl}phenyl, 2-[(thiophen-2-ylsulfonyl)amino]benzyl, N-[(1R,2R)-2-cyclohexyl]thiophene-2-carboxamide, 3-methoxy-2-[(thiophen-2-ylsulfonyl)amino]phenyl, 1-[(1-methyl-3-oxo-1,3-dihydro-sulfonyl]pyrrolidin-3-yl}thiophene-2-sulfonamide, 1-(thiophen-2-ylsulfonyl)pyrrolidin-3-yl]-1,3-dihydro, N-piperidin-3-yl}thiophene-2-sulfonamide, 2,4,5-trichlorophenyl, 3-chlorophenyl, 3-(trifluoromethyl)phenyl, 3,4-dichlorophenyl, 4-chloro-2,5-dimethylphenyl, 4-chloro-2-methoxy-5-methylphenyl, 3-methoxyphenyl, 3-(methylsulfanyl)phenyl, N-[(1R,2R)-2-({[4-chloro-3-(trifluoromethyl)phenyl]sulfonyl}amino)cyclohexyl, N-[(1R,2S)-2-({[4-chloro-3-(trifluoromethyl)phenyl]sulfonyl}amino)cyclohexyl, 3-[(trifluoromethyl)sulfanyl]phenyl, propan-2-yl, 2-hydroxyethyl, 2-methylpropyl, (2-methoxyethyl, 3-methylbutyl, 2-(dimethylamino)ethyl, furan-2-ylmethyl, 5-methyl-1,2-oxazol-3-yl, 2,2,2-trifluoroethyl, cyclohexyl, 4-methylpentan-2-yl, hexyl, benzyl, pyridin-2-ylmethyl, pyridin-4-ylmethyl, cyclohexylmethyl, cycloheptyl, [2-(pyrrolidin-1-yl)ethyl, 3-(propan-2-yloxy)propyl, 1-phenyl-ethyl, 2-phenyl-ethyl, 2-pyridin-2-yl-ethyl, 2-pyridin-3-yl-ethyl, 3-(hydroxymethyl)phenyl, 5-methylpyrazin-2-yl)methyl, 3-(1H-imidazol-1-yl)propyl, piperidine-3-carboxamide, 2-oxoazepan-3-yl, 2-(1-methylpyrrolidin-2-yl)ethyl, 2-(2-oxoimidazolidin-1-yl)ethyl, 2-(morpholin-4-yl)ethyl, (5-methoxy-1,2,4-thiadiazol-3-yl, tert-butylacetate, 2-phenoxyethyl, 3-(2-oxopyrrolidin-1-yl)propyl, 3-(piperidin-1-yl)propyl, 4-phenylbutyl, naphthalen-1-ylmethyl, 2,2-diphenylethyl.

Usually $R^2$ is substituted or unsubstituted $C_{1-6}$ alkyl. Preferred $R^2$ is methyl.

Usually $R^3$ is hydrogen, substituted or unsubstituted $C_{1-6}$ alkyl, halogen, substituted or unsubstituted —$OC_{1-3}$ alkyl, CN, $NO_2$, $C_{2-6}$ alkenyl, $C_{2-6}$ alkynyl, $C(O)R^6$, $NR^7R^8$ or hydroxyl. Preferred $R^3$ is hydrogen.

Usually $R^4$ is hydrogen, substituted or unsubstituted $C_{1-6}$ alkyl, halogen, substituted or unsubstituted —$OC_{1-3}$ alkyl, CN, $NO_2$, $C_{2-6}$ alkenyl, $C_{2-6}$ alkynyl, $C(O)R^6$, $NR^7R^8$ or hydroxyl. Preferred $R^4$ is hydrogen.

Usually $R^5$ is hydrogen, substituted or unsubstituted $C_{1-6}$ alkyl, halogen, substituted or unsubstituted —$OC_{1-3}$ alkyl, CN, $NO_2$, $C_{2-6}$ alkenyl, $C_{2-6}$ alkynyl, $C(O)R^6$, $NR^7R^8$ or hydroxyl. Preferred $R^5$ is hydrogen.

Usually X is O, S or NH. Preferred X is O or NH.

Usually $R^6$ is hydrogen or substituted or unsubstituted $C_{1-6}$ alkyl.

Usually $R^7$ is hydrogen or substituted or unsubstituted $C_{1-6}$ alkyl.

Usually $R^8$ is hydrogen or substituted or unsubstituted $C_{1-6}$ alkyl.

Compounds of the invention are:

N-{5-chloro-2-[(4-oxopiperidin-1-yl)carbonyl]pyridin-3-yl}-1-methyl-3-oxo-1,3-dihydro-2,1-benzisothiazole-5-sulfonamide;

N,N-dimethyl-N-(4-{[(1-methyl-3-oxo-1,3-dihydro-2,1-benzisothiazol-5-yl)carbonyl]amino}benzyl)tetrahydro-2H-pyran-4-aminium;

N-(2,3-dimethoxyphenyl)-1-methyl-3-oxo-1,3-dihydro-2,1-benzisothiazole-5-sulfonamide;

N-(2,3-dihydro-1,4-benzodioxin-5-yl)-1-methyl-3-oxo-1,3-dihydro-2,1-benzisothiazole-5-sulfonamide;

1-isopropyl-3-oxo-N-{2-[(2-thienylsulfonyl)amino]phenyl}-1,3-dihydro-2,1-benzisothiazole-5-sulfonamide;

N-(2,2-difluoro-1,3-benzodioxol-4-yl)-1-methyl-3-oxo-1,3-dihydro-2,1-benzisothiazole-5-sulfonamide;

1-methyl-3-oxo-N-{2-[(2-thienylsulfonyl)amino]pyridin-3-yl}-1,3-dihydro-2,1-benzisothiazole-5-sulfonamide;

N-{5-chloro-2-[(2-thienylsulfonyl)amino]phenyl}-1-methyl-3-oxo-1,3-dihydro-2,1-benzisothiazole-5-sulfonamide;

N-{4-chloro-2-[(2-thienylsulfonyl)amino]phenyl}-1-methyl-3-oxo-1,3-dihydro-2,1-benzisothiazole-5-sulfonamide;

N-1,3-benzodioxol-4-yl-1-methyl-3-oxo-1,3-dihydro-2,1-benzisothiazole-5-sulfonamide;

N-[2-({[4-chloro-3-(trifluoromethyl)phenyl]sulfonyl}amino)phenyl]-1-methyl-3-oxo-1,3-dihydro-2,1-benzisothiazole-5-sulfonamide;

1-isopropyl-3-oxo-N-(2,2,3,3-tetrafluoro-2,3-dihydro-1,4-benzodioxin-5-yl)-1,3-dihydro-2,1-benzisothiazole-5-sulfonamide;

N-{4,5-dichloro-2-[(2-thienylsulfonyl)amino]phenyl}-1-methyl-3-oxo-1,3-dihydro-2,1-benzisothiazole-5-sulfonamide;

N-{5-chloro-2-[(2-thienylsulfonyl)amino]pyridin-3-yl}-1-methyl-3-oxo-1,3-dihydro-2,1-benzisothiazole-5-sulfonamide;

1-methyl-3-oxo-N-[3-(trifluoromethoxy)phenyl]-1,3-dihydro-2,1-benzisothiazole-5-sulfonamide;

N-dibenzo[b,e][1,4]dioxin-1-yl-1-methyl-3-oxo-1,3-dihydro-2,1-benzisothiazole-5-sulfonamide;

N-(7-chloro-2,3-dihydro-1,4-benzodioxin-5-yl)-1-methyl-3-oxo-1,3-dihydro-2,1-benzisothiazole-5-sulfonamide;

N-(2-{[(5-chloro-2-thienyl)sulfonyl]amino}phenyl)-1-methyl-3-oxo-1,3-dihydro-2,1-benzisothiazole-5-sulfonamide;

N-(2-{[(4,5-dichloro-2-thienyl)sulfonyl]amino}phenyl)-1-methyl-3-oxo-1,3-dihydro-2,1-benzisothiazole-5-sulfonamide;

1-methyl-3-oxo-N-{2-[(phenylsulfonyl)amino]phenyl}-1,3-dihydro-2,1-benzisothiazole-5-sulfonamide;

N-(2-{[(4-chlorophenyl)sulfonyl]amino}phenyl)-1-methyl-3-oxo-1,3-dihydro-2,1-benzisothiazole-5-sulfonamide;

N-{2-[(2-furylsulfonyl)amino]phenyl}-1-methyl-3-oxo-1,3-dihydro-2,1-benzisothiazole-5-sulfonamide;

N-{5-bromo-2-[(2-thienylsulfonyl)amino]phenyl}-1-methyl-3-oxo-1,3-dihydro-2,1-benzisothiazole-5-sulfonamide;

1-methyl-3-oxo-N-{2-[(2-thienylsulfonyl)amino]-5-(trifluoromethyl)phenyl}-1,3-dihydro-2,1-benzisothiazole-5-sulfonamide;

1-methyl-N-(2-{[(1-methyl-1H-imidazol-4-yl)sulfonyl]amino}phenyl)-3-oxo-1,3-dihydro-2,1-benzisothiazole-5-sulfonamide;

1-methyl-N-(2-{[(1-methyl-1H-pyrazol-3-yl)sulfonyl]amino}phenyl)-3-oxo-1,3-dihydro-2,1-benzisothiazole-5-sulfonamide;

1-methyl-N-(2-{[(1-methyl-1H-pyrazol-4-yl)sulfonyl]amino}phenyl)-3-oxo-1,3-dihydro-2,1-benzisothiazole-5-sulfonamide;

1-methyl-N-{4-methyl-2-[(2-thienylsulfonyl)amino]phenyl}-3-oxo-1,3-dihydro-2,1-benzisothiazole-5-sulfonamide;

N-{4-chloro-2-[(2-thienylsulfonyl)amino]-5-(trifluoromethyl)phenyl}-1-methyl-3-oxo-1,3-dihydro-2,1-benzisothiazole-5-sulfonamide;

N-{5-methoxy-2-[(2-thienylsulfonyl)amino]phenyl}-1-methyl-3-oxo-1,3-dihydro-2,1-benzisothiazole-5-sulfonamide;

1-methyl-3-oxo-N-{2-[(pyridin-3-ylsulfonyl)amino]phenyl}-1,3-dihydro-2,1-benzisothiazole-5-sulfonamide;

1-methyl-3-oxo-N-{2-[(4H-1,2,4-triazol-3-ylsulfonyl)amino]phenyl}-1,3-dihydro-2,1-benzisothiazole-5-sulfonamide;

N-{2-[(1H-imidazol-4-ylsulfonyl)amino]phenyl}-1-methyl-3-oxo-1,3-dihydro-2,1-benzisothiazole-5-sulfonamide;

N-(2-{[(3,4-dichlorophenyl)sulfonyl]amino}phenyl)-1-methyl-3-oxo-1,3-dihydro-2,1-benzisothiazole-5-sulfonamide;

N-(2-{[(2,5-dichlorophenyl)sulfonyl]amino}phenyl)-1-methyl-3-oxo-1,3-dihydro-2,1-benzisothiazole-5-sulfonamide;

N-(2-{[(2-chlorophenyl)sulfonyl]amino}phenyl)-1-methyl-3-oxo-1,3-dihydro-2,1-benzisothiazole-5-sulfonamide;

N-(2-{[(2-fluorophenyl)sulfonyl]amino}phenyl)-1-methyl-3-oxo-1,3-dihydro-2,1-benzisothiazole-5-sulfonamide;

N-[2-({[3,5-bis(trifluoromethyl)phenyl]sulfonyl}amino)phenyl]-1-methyl-3-oxo-1,3-dihydro-2,1-benzisothiazole-5-sulfonamide;

1-methyl-N-{5-methyl-2-[(2-thienylsulfonyl)amino]phenyl}-3-oxo-1,3-dihydro-2,1-benzisothiazole-5-sulfonamide;

N-{2-fluoro-6-[(2-thienylsulfonyl)amino]phenyl}-1-methyl-3-oxo-1,3-dihydro-2,1-benzisothiazole-5-sulfonamide;

N-{5-cyano-2-[(2-thienylsulfonyl)amino]phenyl}-1-methyl-3-oxo-1,3-dihydro-2,1-benzisothiazole-5-sulfonamide;

N-[5-chloro-2-({[4-chloro-3-(trifluoromethyl)phenyl]sulfonyl}amino)phenyl]-1-methyl-3-oxo-1,3-dihydro-2,1-benzisothiazole-5-sulfonamide;

methyl 3-{[(1-methyl-3-oxo-1,3-dihydro-2,1-benzisothiazol-5-yl)sulfonyl]amino}-4-[(2-thienylsulfonyl)amino]benzoate;

1-methyl-3-oxo-N-[2-({[4-(trifluoromethyl)phenyl]sulfonyl}amino)phenyl]-1,3-dihydro-2,1-benzisothiazole-5-sulfonamide;

N-{2-[(3-furylsulfonyl)amino]phenyl}-1-methyl-3-oxo-1,3-dihydro-2,1-benzisothiazole-5-sulfonamide;

1-methyl-3-oxo-N-[2-({[3-(trifluoromethyl)phenyl]sulfonyl}amino)phenyl]-1,3-dihydro-2,1-benzisothiazole-5-sulfonamide;

N-(2-{[(3,5-dichlorophenyl)sulfonyl]amino}phenyl)-1-methyl-3-oxo-1,3-dihydro-2,1-benzisothiazole-5-sulfonamide;

N-(2-{[(3,5-difluorophenyl)sulfonyl]amino}phenyl)-1-methyl-3-oxo-1,3-dihydro-2,1-benzisothiazole-5-sulfonamide;

N-(2-{[(3-fluorophenyl)sulfonyl]amino}phenyl)-1-methyl-3-oxo-1,3-dihydro-2,1-benzisothiazole-5-sulfonamide;

N-(2-{[(4-methoxyphenyl)sulfonyl]amino}phenyl)-1-methyl-3-oxo-1,3-dihydro-2,1-benzisothiazole-5-sulfonamide;

N-(5-chloro-2-{[(3-chlorophenyl)sulfonyl]amino}phenyl)-1-methyl-3-oxo-1,3-dihydro-2,1-benzisothiazole-5-sulfonamide;

N-(5-chloro-2-{[(3,4-dichlorophenyl)sulfonyl]amino}phenyl)-1-methyl-3-oxo-1,3-dihydro-2,1-benzisothiazole-5-sulfonamide;

N-{4-methoxy-2-[(2-thienylsulfonyl)amino]phenyl}-1-methyl-3-oxo-1,3-dihydro-2,1-benzisothiazole-5-sulfonamide;

N-{4,5-dimethyl-2-[(2-thienylsulfonyl)amino]phenyl}-1-methyl-3-oxo-1,3-dihydro-2,1-benzisothiazole-5-sulfonamide;

N-{4-cyano-2-[(2-thienylsulfonyl)amino]phenyl}-1-methyl-3-oxo-1,3-dihydro-2,1-benzisothiazole-5-sulfonamide;

methyl 4-{[(1-methyl-3-oxo-1,3-dihydro-2,1-benzisothiazol-5-yl)sulfonyl]amino}-3-[(2-thienylsulfonyl)amino]benzoate;

N-(5-chloro-2-{[(3,5-dichlorophenyl)sulfonyl]amino}phenyl)-1-methyl-3-oxo-1,3-dihydro-2,1-benzisothiazole-5-sulfonamide;

N-(5-chloro-2-{[(3-methoxyphenyl)sulfonyl]amino}phenyl)-1-methyl-3-oxo-1,3-dihydro-2,1-benzisothiazole-5-sulfonamide;

N-(5-chloro-2-{[(5-methyl-2-thienyl)sulfonyl]amino}phenyl)-1-methyl-3-oxo-1,3-dihydro-2,1-benzisothiazole-5-sulfonamide;

N-(5-chloro-2-{[(4-methoxyphenyl)sulfonyl]amino}phenyl)-1-methyl-3-oxo-1,3-dihydro-2,1-benzisothiazole-5-sulfonamide;

N-(5-chloro-2-{[(3,4-dimethoxyphenyl)sulfonyl]amino}phenyl)-1-methyl-3-oxo-1,3-dihydro-2,1-benzisothiazole-5-sulfonamide;

N-{5-isopropyl-2-[(2-thienylsulfonyl)amino]phenyl}-1-methyl-3-oxo-1,3-dihydro-2,1-benzisothiazole-5-sulfonamide;

N-{4-isopropyl-2-[(2-thienylsulfonyl)amino]phenyl}-1-methyl-3-oxo-1,3-dihydro-2,1-benzisothiazole-5-sulfonamide;

N-(5-chloro-2-{[(4-methylphenyl)sulfonyl]amino}phenyl)-1-methyl-3-oxo-1,3-dihydro-2,1-benzisothiazole-5-sulfonamide;

N-(5-chloro-2-{[(4-hydroxyphenyl)sulfonyl]amino}phenyl)-1-methyl-3-oxo-1,3-dihydro-2,1-benzisothiazole-5-sulfonamide;

N-{5-chloro-4-methyl-2-[(2-thienylsulfonyl)amino]phenyl}-1-methyl-3-oxo-1,3-dihydro-2,1-benzisothiazole-5-sulfonamide;

N-{4-chloro-5-methyl-2-[(2-thienylsulfonyl)amino]phenyl}-1-methyl-3-oxo-1,3-dihydro-2,1-benzisothiazole-5-sulfonamide;

N-[5-chloro-2-({[4-(dimethylamino)phenyl]sulfonyl}amino)phenyl]-1-methyl-3-oxo-1,3-dihydro-2,1-benzisothiazole-5-sulfonamide;

N-{5-(dimethylamino)-2-[(2-thienylsulfonyl)amino]phenyl}-1-methyl-3-oxo-1,3-dihydro-2,1-benzisothiazole-5-sulfonamide;

N-{4-(dimethylamino)-2-[(2-thienylsulfonyl);amino]phenyl}-1-methyl-3-oxo-1,3-dihydro-2,1-benzisothiazole-5-sulfonamide;

N-(5-chloro-2-{[(4-isopropylphenyl)sulfonyl]amino}phenyl)-1-methyl-3-oxo-1,3-dihydro-2,1-benzisothiazole-5-sulfonamide;

N-{5-chloro-2-[(2-thienylsulfonyl)amino]phenyl}-1-methyl-3-oxo-1,3-dihydro-2,1-benzisothiazole-5-carboxamide;

N-(5-chloro-2-{[(2-methoxyphenyl)sulfonyl]amino}phenyl)-1-methyl-3-oxo-1,3-dihydro-2,1-benzisothiazole-5-sulfonamide;

N-(4-{[(4-chloro-2-{[(1-methyl-3-oxo-1,3-dihydro-2,1-benzisothiazol-5-yl)sulfonyl]amino}phenyl)amino]sulfonyl}phenyl)acetamide;

N-(4-chloro-2-{[(1-methyl-3-oxo-1,3-dihydro-2,1-benzisothiazol-5-yl)sulfonyl]amino}phenyl)-4-methoxybenzamide;

N-[5-chloro-2-({[3-(dimethylamino)phenyl]sulfonyl}amino)phenyl]-1-methyl-3-oxo-1,3-dihydro-2,1-benzisothiazole-5-sulfonamide;

1-methyl-3-oxo-N-{3-[(2-thienylsulfonyl)amino]-2-naphthyl}-1,3-dihydro-2,1-benzisothiazole-5-sulfonamide;

N-{5-ethyl-2-[(2-thienylsulfonyl)amino]phenyl}-1-methyl-3-oxo-1,3-dihydro-2,1-benzisothiazole-5-sulfonamide;

rel-1-methyl-3-oxo-N-{(1R,2R)-2-[(2-thienylsulfonyl)amino]cyclohexyl}-1,3-dihydro-2,1-benzisothiazole-5-sulfonamide 1-methyl-5-{[4-(2-thienylsulfonyl)-3,4-dihydroquinoxalin-1(2H)-yl]sulfonyl}-2,1-benzisothiazol-3(1H)-one;

N-(5-chloro-2-{[(4-ethoxyphenyl)sulfonyl]amino}phenyl)-1-methyl-3-oxo-1,3-dihydro-2,1-benzisothiazole-5-sulfonamide;

N-(5-chloro-2-{[(4-isopropoxyphenyl)sulfonyl]amino}phenyl)-1-methyl-3-oxo-1,3-dihydro-2,1-benzisothiazole-5-sulfonamide;

N-{5-chloro-2-[(2-thienylmethyl)amino]phenyl}-1-methyl-3-oxo-1,3-dihydro-2,1-benzisothiazole-5-sulfonamide;

N-(5-chloro-2-{[(2,4-dimethoxyphenyl)sulfonyl]amino}phenyl)-1-methyl-3-oxo-1,3-dihydro-2,1-benzisothiazole-5-sulfonamide;

N-(4,5-dichloro-2-{[(4-methoxyphenyl)sulfonyl]amino}phenyl)-1-methyl-3-oxo-1,3-dihydro-2,1-benzisothiazole-5-sulfonamide;

rel-1-methyl-3-oxo-N-{(1R,2S)-2-[(2-thienylsulfonyl)amino]cyclohexyl}-1,3-dihydro-2,1-benzisothiazole-5-sulfonamide;

N-(4,5-dichloro-2-{[(3-methoxyphenyl)sulfonyl]amino}phenyl)-1-methyl-3-oxo-1,3-dihydro-2,1-benzisothiazole-5-sulfonamide;

N-{2-chloro-6-[(2-thienylsulfonyl)amino]phenyl}-1-methyl-3-oxo-1,3-dihydro-2,1-benzisothiazole-5-sulfonamide;

N-(4,5-dichloro-2-{[(4,5-dichloro-2-thienyl)sulfonyl]amino}phenyl)-1-methyl-3-oxo-1,3-dihydro-2,1-benzisothiazole-5-sulfonamide;

N-[4,5-dichloro-2-({[4-chloro-3-(trifluoromethyl)phenyl]sulfonyl}amino)phenyl]-1-methyl-3-oxo-1,3-dihydro-2,1-benzisothiazole-5-sulfonamide;

N-(4,5-dichloro-2-{[(5-methyl-2-thienyl)sulfonyl]amino}phenyl)-1-methyl-3-oxo-1,3-dihydro-2,1-benzisothiazole-5-sulfonamide;

1-methyl-3-oxo-N-{3-[(2-thienylsulfonyl)amino]phenyl}-1,3-dihydro-2,1-benzisothiazole-5-sulfonamide;

N-{1,1-dimethyl-2-[(2-thienylsulfonyl)amino]ethyl}-1-methyl-3-oxo-1,3-dihydro-2,1-benzisothiazole-5-sulfonamide;

1-methyl-N-{3-methyl-2-[(2-thienylsulfonyl)amino]phenyl}-3-oxo-1,3-dihydro-2,1-benzisothiazole-5-sulfonamide;

N-{3-chloro-2-[(2-thienylsulfonyl)amino]phenyl}-1-methyl-3-oxo-1,3-dihydro-2,1-benzisothiazole-5-sulfonamide;

1-methyl-N-{2-methyl-2-[(2-thienylsulfonyl)amino]propyl}-3-oxo-1,3-dihydro-2,1-benzisothiazole-5-sulfonamide;

1-methyl-3-oxo-N-(2-{[(2-thienylsulfonyl)amino]methyl}phenyl)-1,3-dihydro-2,1-benzisothiazole-5-sulfonamide;

1-methyl-3-oxo-N-{2-[(2-thienylsulfonyl)amino]benzyl}-1,3-dihydro-2,1-benzisothiazole-5-sulfonamide;

rel-N-[(1R,2R)-2-{[(1-methyl-3-oxo-1,3-dihydro-2,1-benzisothiazol-5-yl)sulfonyl]amino}cyclohexyl]thiophene-2-carboxamide;

N-{3-methoxy-2-[(2-thienylsulfonyl)amino]phenyl}-1-methyl-3-oxo-1,3-dihydro-2,1-benzisothiazole-5-sulfonamide;

N-{1-[(1-methyl-3-oxo-1,3-dihydro-2,1-benzisothiazol-5-yl)sulfonyl]pyrrolidin-3-yl}thiophene-2-sulfonamide;

1-methyl-3-oxo-N-[1-(2-thienylsulfonyl)pyrrolidin-3-yl]-1,3-dihydro-2,1-benzisothiazole-5-sulfonamide;

N-{1-[(1-methyl-3-oxo-1,3-dihydro-2,1-benzisothiazol-5-yl)sulfonyl]piperidin-3-yl}thiophene-2-sulfonamide;

1-methyl-3-oxo-N-[1-(2-thienylsulfonyl)piperidin-3-yl]-1,3-dihydro-2,1-benzisothiazole-5-sulfonamide;

1-methyl-3-oxo-N-(2-{[(2-thienylamino)carbonyl]amino}phenyl)-1,3-dihydro-2,1-benzisothiazole-5-sulfonamide;

1-methyl-3-oxo-N-(2,4,5-trichlorophenyl)-1,3-dihydro-2,1-benzisothiazole-5-sulfonamide;

N-(3-chlorophenyl)-1-methyl-3-oxo-1,3-dihydro-2,1-benzisothiazole-5-sulfonamide;

1-methyl-3-oxo-N-[3-(trifluoromethyl)phenyl]-1,3-dihydro-2,1-benzisothiazole-5-sulfonamide;

N-(3,4-dichlorophenyl)-1-methyl-3-oxo-1,3-dihydro-2,1-benzisothiazole-5-sulfonamide;

N-(4-chloro-2,5-dimethylphenyl)-1-methyl-3-oxo-1,3-dihydro-2,1-benzisothiazole-5-sulfonamide;

N-(4-chloro-2-methoxy-5-methylphenyl)-1-methyl-3-oxo-1,3-dihydro-2,1-benzisothiazole-5-sulfonamide;

N-(3-methoxyphenyl)-1-methyl-3-oxo-1,3-dihydro-2,1-benzisothiazole-5-sulfonamide;

1-methyl-N-[3-(methylthio)phenyl]-3-oxo-1,3-dihydro-2,1-benzisothiazole-5-sulfonamide;

rel-N-[(1R,2R)-2-({[4-chloro-3-(trifluoromethyl)phenyl]sulfonyl}amino)cyclohexyl]-1-methyl-3-oxo-1,3-dihydro-2,1-benzisothiazole-5-sulfonamide;

rel-N-[(1R,2S)-2-({[4-chloro-3-(trifluoromethyl)phenyl]sulfonyl}amino)cyclohexyl]-1-methyl-3-oxo-1,3-dihydro-2,1-benzisothiazole-5-sulfonamide;

1-methyl-3-oxo-N-{3-[(trifluoromethyl)thio]phenyl}-1,3-dihydro-2,1-benzisothiazole-5-sulfonamide.

Some compounds of Formula I and some of their intermediates have at least one stereogenic center in their structure. This stereogenic center may be present in an R or S configuration, said R and S notation is used in correspondence with the rules described in Pure Appli. Chem. (1976), 45, 11-13.

The term "pharmaceutically acceptable salts" refers to salts or complexes that retain the desired biological activity of the above identified compounds and exhibit minimal or no undesired toxicological effects. The "pharmaceutically acceptable salts" according to the invention include therapeutically active, non-toxic base or acid salt forms, which the compounds of Formula I are able to form.

The acid addition salt form of a compound of Formula I that occurs in its free form as a base can be obtained by treating the free base with an appropriate acid such as an inorganic acid, for example, hydrochloric acid, hydrobromic acid, sulfuric acid, phosphoric acid, nitric acid and the like; or an organic acid such as for example, acetic, hydroxyacetic, propanoic, lactic, pyruvic, malonic, fumaric acid, maleic acid, oxalic acid, tartaric acid, succinic acid, malic acid, ascorbic acid, benzoic acid, tannic acid, pamoic acid, citric, methylsulfonic, ethanesulfonic, benzenesulfonic, formic and the like (Handbook of Pharmaceutical Salts, P. Heinrich Stahal & Camille G. Wermuth (Eds), Verlag Helvetica Chemica Acta-Zürich, 2002, 329-345).

The base addition salt form of a compound of Formula I that occurs in its acid form can be obtained by treating the acid with an appropriate base such as an inorganic base, for example, sodium hydroxide, magnesium hydroxide, potassium hydroxide, Calcium hydroxide, ammonia and the like; or an organic base such as for example, L-Arginine, ethanolamine, betaine, benzathine, morpholine and the like. (Handbook of Pharmaceutical Salts, P. Heinrich Stahal & Camille G. Wermuth (Eds), Verlag Helvetica Chemica Acta-Zürich, 2002, 329-345).

Compounds of Formula I and their salts can be in the form of a solvate, which is included within the scope of the present invention. Such solvates include for example hydrates, alcoholates and the like.

With respect to the present invention reference to a compound or compounds, is intended to encompass that compound in each of its possible isomeric forms and mixtures thereof unless the particular isomeric form is referred to specifically.

Compounds according to the present invention may exist in different polymorphic forms. Although not explicitly indicated in the above formula, such forms are intended to be included within the scope of the present invention.

The compounds of the invention are indicated for use in treating or preventing conditions in which there is likely to be a component involving the chemokine receptors.

In another embodiment, there are provided pharmaceutical compositions including at least one compound of the invention in a pharmaceutically acceptable carrier.

In a further embodiment of the invention, there are provided methods for treating disorders associated with modulation of chemokine receptors. Such methods can be performed, for example, by administering to a subject in need thereof a pharmaceutical composition containing a therapeutically effective amount of at least one compound of the invention.

These compounds are useful for the treatment of mammals, including humans, with a range of conditions and diseases that are alleviated by CCR modulation Therapeutic utilities of CCR modulators are skin inflammatory diseases and conditions, including, but are not limited to: rosacea (dilation of the blood vessels just under the skin), sunburn, chronic sun damage, discreet erythemas, psoriasis, atopic dermatitis, menopause-associated hot flashes, hot flashes resulting from orchiectomyatopic dermatitis, photoaging, seborrheic dermatitis, acne, allergic dermatitis, irritant dermatitis, telangiectasia (dilations of previously existing small blood vessels) of the face, rhinophyma (hypertrophy of the nose with follicular dilation), red bulbous nose, acne-like skin eruptions (may ooze or crust), burning or stinging sensation of the face, irritated and bloodshot and watery eyes, cutaneous hyperactivity with dilation of blood vessels of the skin, Lyell's syndrome, Stevens-Johnson syndrome, erythema multiforme minor, erythema multiforme major and other inflammatory skin diseases, actinic keratoses, arsenic keratoses, inflammatory and non-inflammatory acne, ichthyoses and other keratinization and hyperproliferative disorders of the skin, eczema, wound healing.

Therapeutic utilities of CCR modulators are ocular inflammatory diseases including, but not limited to, uveitis, dry eye, Keratitis, allergic eye disease and conditions affecting the posterior part of the eye, such as maculopathies and retinal degeneration including non-exudative age related macular degeneration, exudative age related macular degeneration, choroidal neovascularization, diabetic retinopathy, acute macular neuroretinopathy, central serous chorioretinopathy, cystoid macular edema, and diabetic macular edema; uveitis, retinitis, and choroiditis such as acute multifocal placoid pigment epitheliopathy, Behcet's disease, birdshot retinochoroidopathy, infectious (syphilis, lyme, tuberculosis, toxoplasmosis), intermediate uveitis (pars planitis), multifocal choroiditis, multiple evanescent white dot syndrome (mewds), ocular sarcoidosis, posterior scleritis, serpiginous choroiditis, subretinal fibrosis and uveitis syndrome, Vogt-Koyanagi- and Harada syndrome; vasuclar diseases/exudative diseases such as retinal arterial occlusive disease, central retinal vein occlusion, disseminated intravascular coagulopathy, branch retinal vein occlusion, hypertensive fundus changes, ocular ischemic syndrome, retinal arterial microaneurysms, Coat's disease, parafoveal telangiectasis, hemi-retinal vein occlusion, papillophlebitis, central retinal artery occlusion, branch retinal artery occlusion, carotid artery disease (CAD), frosted branch angiitis, sickle cell retinopathy and other hemoglobinopathies, angioid streaks, familial exudative vitreoretinopathy, and Eales disease; traumatic/surgical conditions such as sympathetic ophthalmia, uveitic retinal disease, retinal detachment, trauma, conditions caused by laser, conditions caused by photodynamic therapy, photocoagulation, hypoperfusion during surgery, radiation retinopathy, and bone marrow transplant retinopathy; proliferative disorders such as proliferative vitreal retinopathy and epiretinal membranes, and proliferative diabetic retinopathy; infectious disorders such as ocular histoplasmosis, ocular toxocariasis, presumed ocular histoplasmosis syndrome (PONS), endophthalmitis, toxoplasmosis, retinal diseases associate with HIV infection, choroidal disease associate with HIV infection, uveitic disease associate with HIV infection, viral retinitis, acute retinal necrosis, progressive outer retinal necrosis, fungal retinal diseases, ocular syphilis, ocular tuberculosis, diffuse unilateral subacute neuroretinitis, and myiasis; genetic disorders such as retinitis pigmentosa, systemic disorders with accosiated retinal dystrophies, congenital stationary night blindness, cone dystrophies, Stargardt's disease and fundus flavimaculatus, Best's disease, pattern dystrophy of the retinal pigmented epithelium, X-linked retinoschisis, Sorsby's fundus dystrophy, benign concentric maculopathy, Bietti's crystalline dystrophy, and pseudoxanthoma elasticum; retinal tears/holes such as retinal detachment, macular hole, and giant retinal tear; tumors such as retinal disease associated with tumors, congenital hypertrophy of the retinal pigmented epithelium, posterior uveal melanoma, choroidal hemangioma, choroidal osteoma, choroidal metastasis, combined hamartoma of the retina and retinal pigmented epithelium, retinoblastoma, vasoproliferative tumors of the ocular fundus, retinal astrocytoma, and intraocular lymphoid tumors; and miscellaneous other diseases affecting the posterior part of the eye such as punctate inner choroidopathy, acute posterior multifocal placoid pigment epitheliopathy, myopic retinal degeneration, and acute retinal pigement epitheliitis.

In still another embodiment of the invention, there are provided methods for treating disorders associated with modulation of chemokine receptors. Such methods can be performed, for example, by administering to a subject in need thereof a therapeutically effective amount of at least one compound of the invention, or any combination thereof, or pharmaceutically acceptable salts, hydrates, solvates, crystal forms and individual isomers, enantiomers, and diastereomers thereof.

The present invention concerns the use of a compound of Formula I or a pharmaceutically acceptable salt thereof, for the manufacture of a medicament for the treatment of ocular inflammatory diseases including, but not limited to, uveitis, dry eye, Keratitis, allergic eye disease and conditions affecting the posterior part of the eye, such as maculopathies and retinal degeneration including non-exudative age related macular degeneration, exudative age related macular degeneration, choroidal neovascularization, diabetic retinopathy, acute macular neuroretinopathy, central serous chorioretinopathy, cystoid macular edema, and diabetic macular edema; uveitis, retinitis, and choroiditis such as acute multifocal placoid pigment epitheliopathy, Behcet's disease, birdshot retinochoroidopathy, infectious (syphilis, lyme, tuberculosis, toxoplasmosis), intermediate uveitis (pars planitis), multifocal choroiditis, multiple evanescent white dot syndrome (mewds), ocular sarcoidosis, posterior scleritis, serpiginous choroiditis, subretinal fibrosis and uveitis syndrome, Vogt-Koyanagi- and Harada syndrome; vasuclar diseases/exudative diseases such as retinal arterial occlusive disease, central retinal vein occlusion, disseminated intravascular coagulopathy, branch retinal vein occlusion, hypertensive fundus changes, ocular ischemic syndrome, retinal arterial microaneurysms, Coat's disease, parafoveal telangiectasis, hemi-retinal vein occlusion, papillophlebitis, central retinal artery occlusion, branch retinal artery occlusion, carotid artery disease (CAD), frosted branch angiitis, sickle cell retinopathy and other hemoglobinopathies, angioid streaks, familial exudative vitreoretinopathy, and Eales disease; traumatic/surgical conditions such as sympathetic ophthalmia, uveitic retinal disease, retinal detachment, trauma, conditions caused by laser, conditions caused by photodynamic therapy, photocoagulation, hypoperfusion during surgery, radiation retinopathy, and bone marrow transplant retinopathy; proliferative disorders such as proliferative vitreal retinopathy and epiretinal membranes, and proliferative diabetic retinopathy; infectious disorders such as ocular histoplasmosis, ocular toxocariasis, presumed ocular histoplasmosis syndrome (PONS), endophthalmitis, toxoplasmosis, retinal diseases associated with HIV infection, choroidal disease associate with HIV infection, uveitic disease associate with HIV infection, viral retinitis, acute retinal necrosis, progressive outer retinal necrosis, fungal retinal diseases, ocular syphilis, ocular tuberculosis, diffuse unilateral subacute neuroretinitis, and myiasis; genetic disorders such as retinitis pigmentosa, systemic disorders with accosiated retinal dystrophies, congenital stationary night blindness, cone dystrophies, Stargardt's disease and fundus flavimaculatus, Best's disease, pattern dystrophy of the retinal pigmented epithelium, X-linked retinoschisis, Sorsby's fundus dystrophy, benign concentric maculopathy, Bietti's crystalline dystrophy, and pseudoxanthoma elasticum; retinal tears/holes such as retinal detachment, macular hole, and giant retinal tear; tumors such as retinal disease associated with tumors, congenital hypertrophy of the retinal pigmented epithelium, posterior uveal melanoma, choroidal hemangioma, choroidal osteoma, choroidal metastasis, combined hamartoma of the retina and retinal pigmented epithelium, retinoblastoma, vasoproliferative tumors of the ocular fundus, retinal astrocytoma, and intraocular lymphoid tumors; and miscellaneous other diseases affecting the posterior part of the eye such as punctate inner choroidopathy, acute posterior multifocal placoid pigment epitheliopathy, myopic retinal degeneration, and acute retinal pigement epitheliitis.

The actual amount of the compound to be administered in any given case will be determined by a physician taking into account the relevant circumstances, such as the severity of the condition, the age and weight of the patient, the patient's general physical condition, the cause of the condition, and the route of administration.

The patient will be administered the compound orally in any acceptable form, such as a tablet, liquid, capsule, powder and the like, or other routes may be desirable or necessary, particularly if the patient suffers from nausea. Such other routes may include, without exception, transdermal, parenteral, subcutaneous, intranasal, via an implant stent, intrathecal, intravitreal, topical to the eye, back to the eye, intramuscular, intravenous, and intrarectal modes of delivery. Additionally, the formulations may be designed to delay release of the active compound over a given period of time, or to carefully control the amount of drug released at a given time during the course of therapy.

In another embodiment of the invention, there are provided pharmaceutical compositions including at least one compound of the invention in a pharmaceutically acceptable carrier thereof. The phrase "pharmaceutically acceptable" means the carrier, diluent or excipient must be compatible with the other ingredients of the formulation and not deleterious to the recipient thereof.

Pharmaceutical compositions of the present invention can be used in the form of a solid, a solution, an emulsion, a dispersion, a patch, a micelle, a liposome, and the like, wherein the resulting composition contains one or more compounds of the present invention, as an active ingredient, in admixture with an organic or inorganic carrier or excipient suitable for enteral or parenteral applications. Invention compounds may be combined, for example, with the usual non-toxic, pharmaceutically acceptable carriers for tablets, pellets, capsules, suppositories, solutions, emulsions, suspensions, and any other form suitable for use. The carriers which can be used include glucose, lactose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition auxiliary, stabilizing, thickening and coloring agents and perfumes may be used. Invention compounds are included in the pharmaceutical composition in an amount sufficient to produce the desired effect upon the process or disease condition.

Pharmaceutical compositions containing invention compounds may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known in the art for the manufacture of pharmaceutical compositions and such compositions may contain one or more agents selected from the group consisting of a sweetening agent such as sucrose, lactose, or saccharin, flavoring agents such as peppermint, oil of wintergreen or cherry, coloring agents and preserving agents in order to provide pharmaceutically elegant and palatable preparations. Tablets containing invention compounds in admixture with non-toxic pharmaceutically acceptable excipients may also be manufactured by known methods. The excipients used may be, for example, (1) inert diluents such as calcium carbonate, lactose, calcium phosphate or sodium phosphate; (2) granulating and disintegrating agents such as corn starch, potato starch or alginic acid; (3) binding agents such as gum tragacanth, corn starch, gelatin or acacia, and (4) lubricating agents such as magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

In some cases, formulations for oral use may be in the form of hard gelatin capsules wherein the invention compounds are mixed with an inert solid diluent, for example, calcium carbonate, calcium phosphate or kaolin. They may also be in the form of soft gelatin capsules wherein the invention compounds are mixed with water or an oil medium, for example, peanut oil, liquid paraffin or olive oil.

The pharmaceutical compositions may be in the form of a sterile injectable suspension. This suspension may be formulated according to known methods using suitable dispersing or wetting agents and suspending agents. The sterile injectable preparation may also be a sterile injectable solution or suspension in a non-toxic parenterally-acceptable diluent or solvent, for example, as a solution in 1,3-butanediol. Sterile, fixed oils are conventionally employed as a solvent or suspending medium. For this purpose any bland fixed oil may be employed including synthetic mono- or diglycerides, fatty acids (including oleic acid), naturally occurring vegetable oils like sesame oil, coconut oil, peanut oil, cottonseed oil, etc., or synthetic fatty vehicles like ethyl oleate or the like. Buffers, preservatives, antioxidants, and the like can be incorporated as required.

Invention compounds may also be administered in the form of suppositories for rectal administration of the drug. These compositions may be prepared by mixing the invention compounds with a suitable non-irritating excipient, such as cocoa butter, synthetic glyceride esters of polyethylene glycols, which are solid at ordinary temperatures, but liquefy and/or dissolve in the rectal cavity to release the drug.

Since individual subjects may present a wide variation in severity of symptoms and each drug has its unique therapeutic characteristics, the precise mode of administration and dosage employed for each subject is left to the discretion of the practitioner.

The compounds and pharmaceutical compositions described herein are useful as medicaments in mammals, including humans, for treatment of diseases and/or alleviations of conditions which are responsive to treatment by agonists or functional antagonists of chemokine receptors. Thus, in further embodiments of the invention, there are provided methods for treating a disorder associated with modulation of chemokine receptors. Such methods can be performed, for example, by administering to a subject in need thereof a pharmaceutical composition containing a therapeutically effective amount of at least one invention compound. As used herein, the term "therapeutically effective amount" means the amount of the pharmaceutical composition that will elicit the biological or medical response of a subject in need thereof that is being sought by the researcher, veterinarian, medical doctor or other clinician. In some embodiments, the subject in need thereof is a mammal. In some embodiments, the mammal is human.

The present invention concerns also processes for preparing the compounds of Formula I. The compounds of formula I according to the invention can be prepared analogously to conventional methods as understood by the person skilled in the art of synthetic organic chemistry. The synthetic schemes set forth below, illustrate how compounds according to the invention can be made. Those skilled in the art will be able to routinely modify and/or adapt Scheme 1 and 2 to synthesize any compounds of the invention covered by Formula I.

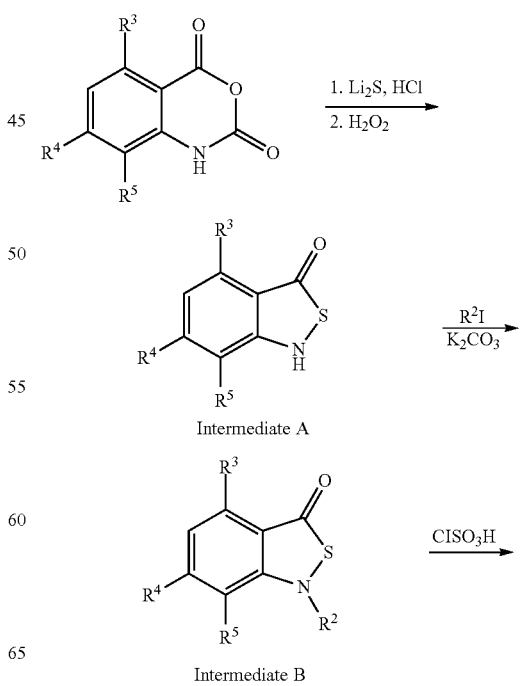

Scheme 1

Intermediate A

To a solution of Li₂S (0.124 mol) in H₂O (1000 ml) cooled to 0° C. in an ice bath was added HCl (0.186 mmol) slowly with stirring. The ice bath was then removed, and an appropriately substituted isatoic anhydride (0.050 mol) was added slowly. The suspension was stirred for 1 h and was filtered. The filtrate was purged with N₂ for 30 min, and H₂O₂ (30%, 7.0 ml) was added, stirred for 45 min. The pH of the reaction mixture was adjusted with 6M HCl to ~5 and the resulting suspension was filtered. The solid was washed with H₂O (×3) and was dried to yield the Intermediate A type as an off-white solid.

Intermediate B

To an Intermediate A type (27.8 mmol) in acetone (100 ml) was added the corresponding iodide derivative (83.4 mmol) and K₂CO₃ (55.6 mmol). The mixture was heated at 60° C. for 2 h, and was filtered and concentrated. The crude product was purified by flash column chromatography on silica gel eluting with 20%‡30% EtOAc-hexane to yield an Intermediate B type as a yellow solid.

Intermediate C

Chlorosulfonic acid (25 ml) was added to an Intermediate B type derivative (26.7 mmol). The resulting solution was stirred at room temperature for 30 min and then at 100° C. for 10 min. The reaction was cooled to room temperature and was added dropwise with caution to ice. The yellow suspension was filtered, washed with H₂O (×3) and was dried to yield Intermediate C as a golden yellow solid.

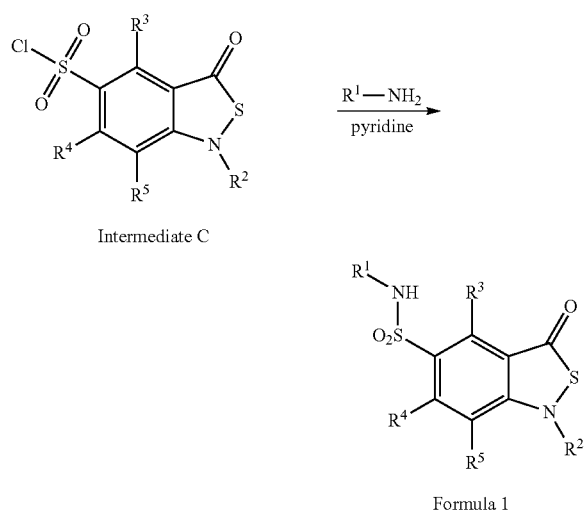

Scheme 2

Compounds of Formula I

One equivalent of the desired amine and one equivalent of Intermediate C in pyridine were stirred at room temperature or at 100° C. and the reaction was monitored by TLC analysis. The reaction was then concentrated and the crude product was purified by flash column chromatography on silica gel to yield the desired compound of Formula I.

Procedures for Synthesizing

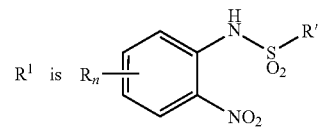

R and R' are Substitutents on the Phenyl Ring of R¹ and n is 0-4

Procedure 1

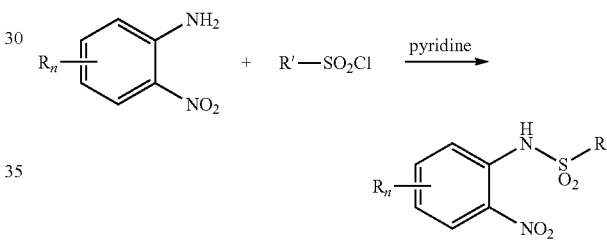

A solution of appropriately substituted 2-nitro-aniline (1 equiv.) and aryl sulfonyl chloride (2.5 equiv.) in pyridine was heated at 100° C. for 4 h, MeOH was then added, followed by 4M NaOH (excess), and the reaction was heated at 100° C. for 1 h, cooled to room temperature, acidified with 6M HCl, and extracted with EtOAc (×2). The combined organic layer was washed with brine, dried over Na₂SO₄, and concentrated. The crude product was purified by flash column chromatography on silica gel to yield the desired product.

Procedure 2

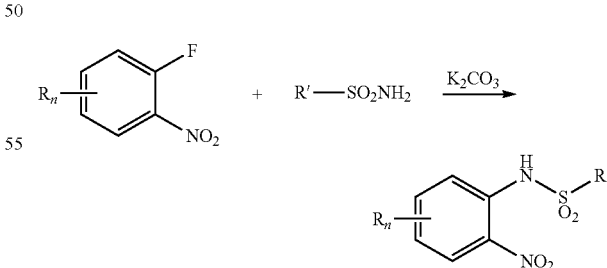

A mixture of appropriately substituted 1-fluoro-2-nitrobenzene (1 equiv.), aryl sulfonamide (1 equiv.), and K₂CO₃ (1 equiv.) in DMSO was stirred at room temperature or heated at 60-80° C. until TLC analysis indicated completion of the reaction. The reaction was then quenched with 1M HCl and was extracted with EtOAc (×2). The combined organic layer was washed with brine, dried over Na$_2$SO$_4$, and concentrated. The crude product was purified by flash column chromatography on silica gel to yield the desired product.

Procedure 3

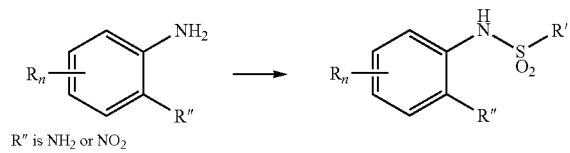

R″ is NH$_2$ or NO$_2$

A solution of appropriately substituted symmetrical phenylene diamine or appropriately substituted 2-nitro-aniline (1 equiv.) and aryl sulfonyl chloride (1 equiv.) in pyridine was heated at 100° C. for 4 h and was concentrated. The crude product was purified by flash column chromatography on silica gel to yield the desired product.

Procedure 4

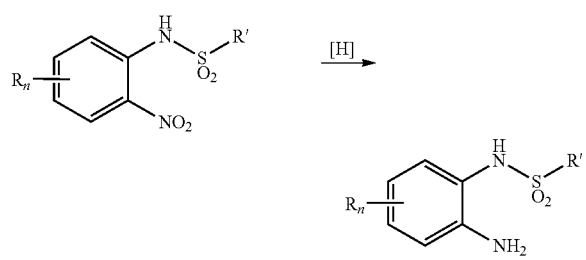

To a stirred solution/suspension of N-(2-nitrophenyl)sulfonamide (1 equiv.) in MeOH and saturated aqueous NH$_4$Cl (2:1) at room temperature was added zinc dust (25 equiv.). The mixture was stirred for 10 min to 1 h, and was filtered. The filtrate was extracted with EtOAc (×2). The combined organic layer was washed with brine, dried over Na$_2$SO$_4$, and concentrated. The crude product was purified by flash column chromatography on silica gel to yield the desired product.

DETAILED DESCRIPTION OF THE INVENTION

It is to be understood that both the foregoing general description and the following detailed description are exemplary and explanatory only and are not restrictive of the invention claimed. As used herein, the use of the singular includes the plural unless specifically stated otherwise.

It will be readily apparent to those skilled in the art that some of the compounds of the invention may contain one or more asymmetric centers, such that the compounds may exist in enantiomeric as well as in diastereomeric forms. Unless it is specifically noted otherwise, the scope of the present invention includes all enantiomers, diastereomers and racemic mixtures. Some of the compounds of the invention may form salts with pharmaceutically acceptable acids or bases, and such pharmaceutically acceptable salts of the compounds described herein are also within the scope of the invention.

The present invention includes all pharmaceutically acceptable isotopically enriched compounds. Any compound of the invention may contain one or more isotopic atoms enriched or different than the natural ratio such as deuterium $^2$H (or D) in place of protium $^1$H (or H) or use of $^{13}$C enriched material in place of $^{12}$C and the like. Similar substitutions can be employed for N, O and S. The use of isotopes may assist in analytical as well as therapeutic aspects of the invention. For example, use of deuterium may increase the in vivo half-life by altering the metabolism (rate) of the compounds of the invention. These compounds can be prepared in accord with the preparations described by use of isotopically enriched reagents.

As will be evident to those skilled in the art, individual isomeric forms can be obtained by separation of mixtures thereof in conventional manner. For example, in the case of diastereoisomeric isomers, chromatographic separation may be employed.

Compound names were generated with ACD version 8 and some intermediates' and reagents' names used in the examples were generated with software such as Chem Bio Draw Ultra version 12.0 or Auto Nom 2000 from MDL ISIS Draw 2.5 SP1. In general, characterization of the compounds is performed according to the following methods:

NMR spectra are recorded on Varian 600 or Varian 300, in the indicated solvent at ambient temperature; chemical shifts in [ppm], coupling constants in [Hz]. All the reagents, solvents, catalysts for which the synthesis is not described are purchased from chemical vendors such as Sigma Aldrich, Fluka, Bio-Blocks, Combi-blocks, TCI, VWR, Lancaster, Oakwood, Trans World Chemical, Alfa, Fisher, Maybridge, Frontier, Matrix, Ukrorgsynth, Toronto, Ryan Scientific, Sili-Cycle, Anaspec, Syn Chem, Chem-Impex, MIC-scientific, Ltd; however some known intermediates, were prepared according to published procedures. Solvents were purchased from commercial sources in appropriate quality and used as received. Air and/or moisture-sensitive reactions were run under an Ar— or N$_2$— atmosphere.

Usually the compounds of the invention were purified by chromatography: CombiFlash Companion and RediSep Rf silica gel 60 (0.04-0.063 mm); Preparative thin layer chromatography (PTLC): Analtech (silica gel 60 F$_{254}$, 500 or 1000 μm).

The following abbreviations are used in the examples:

| | |
|---|---|
| s, m, h, d | second, minute, hour, day |
| NH$_3$ | ammonia |
| CH$_3$CN | acetonitrile |
| CH$_2$Cl$_2$ | dichloromethane |
| DMF | N,N-dimethylformamide |
| NaOH | sodium hydroxide |
| MeOH | methanol |
| CD$_3$OD | deuterated methanol |
| HCl | hydrochloric acid |
| Na$_2$SO$_4$ | sodium sulfate |
| HBTU | 2-(1H-Benzotriazole-1-yl)-1,1,3,3-tetramethyluronium hexafluorophosphate) |
| DIPEA | N,N-Diisopropylethylamine |
| CuI | copper iodide |
| Cs$_2$CO$_3$ | cesium carbonate |
| DMEDA | dimethylethylenediamine |
| MgSO$_4$ | magnesium sulfate |
| EtOAc | ethyl acetate |
| CDCl$_3$ | deuterated chloroform |
| DMSO-d$_6$ | deuterated dimethyl sulfoxide |
| Auto-column | automated flash liquid chromatography |
| TFA | trifluoroacetic acid |
| THF | tetrahydrofuran |
| K$_2$CO$_3$ | potassium carbonate |
| mCPBA | meta-Chloroperoxybenzoic acid |

The following examples are for illustrative purposes only and are not intended, nor should they be construed as limiting the invention in any manner. Those skilled in the art will appreciate that variations and modifications of the following examples can be made without exceeding the spirit or scope of the invention.

Example 1

Intermediate 1

1-Isopropylbenzo[c]isothiazol-3(1H)-one

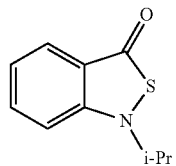

To a solution of Benzo[c]isothiazol-3(1H)-one (CAS 40352-87-2) (151 mg, 1.0 mmol) in acetone (10 ml) was added i-PrI (0.5 ml, 5.0 mmol) and $K_2CO_3$ (414 mg, 3.0 mmol). The mixture was heated to 60° C. for 3 h, and was filtered and concentrated. The crude product was purified by flash column chromatography on silica gel eluting with 0%→30% EtOAc-hexane to yield Intermediate 1 as brown syrup.

$^1$H NMR (300 MHz, CDCl$_3$) δ ppm 7.79 (d, 1H), 7.47-7.57 (m, 1H), 7.21 (d, J=8.50 Hz, 1H), 7.01 (t, J=7.47 Hz, 1H), 4.55-4.73 (m, 1H), 1.37 (d, J=6.45 Hz, 6H).

Example 2

Intermediate 2

1-Methyl-3-oxo-1,3-dihydrobenzo[c]isothiazole-5-sulfonyl chloride

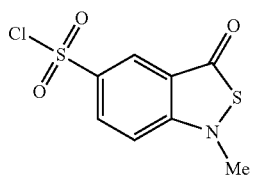 [SMILES: Cn1sc(=O)c2cc(S(=O)(=O)Cl)ccc21]

Chlorosulfonic acid (25 ml) was added to 1-Methylbenzo[c]isothiazol-3(1H)-one (CAS 23310-36-3) (4.4 g, 26.7 mmol). The resulting solution was stirred at room temperature for 30 min and then at 100° C. for 10 min. The reaction was cooled to room temperature and was added dropwise with caution to ice. The yellow suspension was filtered, washed with $H_2O$ (×3) and was dried to yield Intermediate 2 as a golden yellow solid.

$^1$H NMR (300 MHz, CHLOROFORM-d) δ ppm 8.53 (d, J=2.05 Hz, 1H), 8.12 (dd, J=2.20, 9.23 Hz, 1H), 7.24-7.34 (m, 1H), 3.62 (s, 3H).

Example 3

Intermediate 3

1-Isopropyl-3-oxo-1,3-dihydrobenzo[c]isothiazole-5-sulfonyl chloride

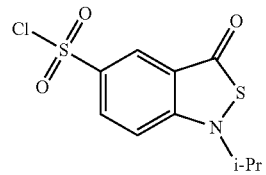 [SMILES: CC(C)n1sc(=O)c2cc(S(=O)(=O)Cl)ccc21]

Chlorosulfonic acid (1.0 ml) was added to Intermediate 1 (74 mg, 0.38 mmol). The resulting solution was stirred at room temperature for 30 min and then at 100° C. for 10 min. The reaction was cooled to room temperature and was added dropwise with caution to ice. The yellow suspension was filtered, washed with $H_2O$ (×3) and the solid was taken in THF, dried over $Na_2SO_4$ and concentrated to yield Intermediate 3 as a brown solid. The crude product was used without further purification and characterization.

Example 4

Intermediate 4

1-Nitrodibenzo[b,e][1,4]dioxine

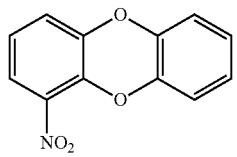 [SMILES: O=[N+]([O-])c1cccc2c1Oc1ccccc1O2]

After a solution of catchol (1 equiv.), $K_2CO_3$, 18-crown-6 (2 equiv.) in dried acetone was refluxed under $N_2$ for 45 min., a solution of 2-chloro-1,3-dinitrobenzene (1 equiv.) in dried acetone was then added. The reaction mixture was refluxed under $N_2$ for 16 hours. After cooling, the reaction mixture was poured onto ice, and the yellow precipitate was collected and dried. The crude product was purified by flash column chromatography on silica gel to yield Intermediate 4 as a yellow solid.

$^1$H NMR (300 MHz, CDCl$_3$): δ ppm 7.53 (dd, J=8.4, 1.6 Hz, 1H), 7.09 (dd, J=8.2, 1.8 Hz, 1H), 6.94-7.03 (m, 4H), 6.84-6.93 ppm (m, 1H).

Example 5

Intermediate 5

Dibenzo[b,e][1,4]dioxin-1-amine

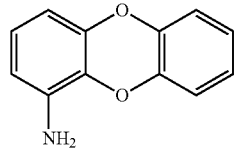

A mixture of Intermediate 4 (1 equiv.) and 10% wt Pd—C (0.1 equiv.) in EtOAc under H$_2$ balloon was stirred overnight. The catalyst was filtered. The crude product was purified by flash column chromatography on silica gel to yield Intermediate 5 as a white solid.

$^1$H NMR (300 MHz, CDCl$_3$): δ ppm 6.79-6.95 (m, 6H), 6.67 ppm (dd, J=7.5, 2.2 Hz, 1H).

Example 6

Intermediate 6

N-(5-isopropyl-2-nitrophenyl)acetamide

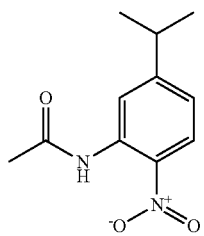

N-(3-isopropylphenyl)acetamide (CAS 7766-63-4), 2.2 g, crude) was added drop-wise to fuming HNO$_3$ at 0° C. The reaction was stirred at room temperature for 3 h, quenched with ice, extracted with EtOAc (×2). The combined organic layer was washed with brine, dried over Na$_2$SO$_4$, and concentrated. The crude product was purified by flash chromatography on silica gel eluting with 0%→50% EtOAc-hexanes to yield Intermediate 6 as a yellowish brown solid.

$^1$H NMR (300 MHz, CDCl$_3$) δ ppm 10.43 (br. s., 1H), 8.68 (d, J=1.76 Hz, 1H), 8.15 (d, J=8.50 Hz, 1H), 7.03 (dd, J=1.90, 8.64 Hz, 1H), 2.90-3.08 (m, J=6.74, 6.92, 6.92, 6.92, 6.92, 6.92 Hz, 1H), 2.29 (s, 3H), 1.28 (d, J=7.03 Hz, 6H).

Example 7

Intermediate 7

N-(4-chloro-2-nitrophenyl)-4-(dimethylamino)benzenesulfonamide

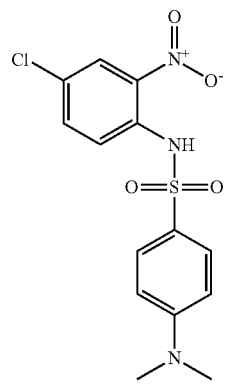 [SMILES: CN(C)c1ccc(S(=O)(=O)Nc2ccc(Cl)cc2[N+](=O)[O-])cc1]

A solution of 4-(dimethylamino)benzenesulfonamide (CAS 6162-21-6) (1 equiv.) in DMF was cannulated into NaH in DMF at room temperature. After stirring for 10 min, 4-chloro-1-fluoro-2-nitrobenzene (1 equiv) in DMF was added into the above solution and stirred for another 30 min. The reaction was quenched with water and extracted with EtOAc (×2). The combined organic layer was washed with brine, dried over Na$_2$SO$_4$, and concentrated. The crude product was purified by flash column chromatography on silica gel to yield Intermediate 7 as an orange solid (45% yield).

$^1$H NMR (300 MHz, CD$_3$OD) δ ppm 8.20 (d, J=1.47 Hz, 1H), 7.77 (d, J=9.08 Hz, 2H), 7.54 (d, J=2.93 Hz, 2H), 7.46 (d, 2H), 2.65-2.74 (m, 6H).

Example 8

Intermediate 8

N-(4-chloro-2-nitrophenyl)-3-(dimethylamino)benzenesulfonamide

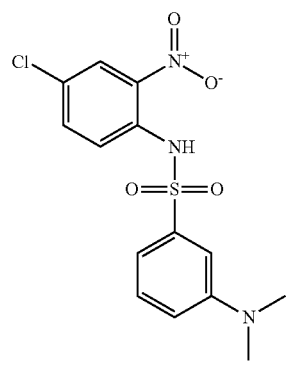 [SMILES: CN(C)c1cccc(S(=O)(=O)Nc2ccc(Cl)cc2[N+](=O)[O-])c1]

Intermediate 8 was prepared from 3-(dimethylamino)benzenesulfonamide (CAS 63935-19-3) according to the procedure described for Intermediate 7.

¹H NMR (300 MHz, CD₃OD) δ ppm 8.20 (d, J=2.34 Hz, 1H), 7.67-7.71 (m, 1H), 7.56-7.67 (m, 3H), 7.49 (dd, J=2.49, 9.23 Hz, 1H), 7.29 (d, J=9.08 Hz, 1H), 2.72 (s, 6H).

Example 9

Intermediate 9

Methyl 1-methyl-3-oxo-1,3-dihydrobenzo[c]isothiazole-5-carboxylate

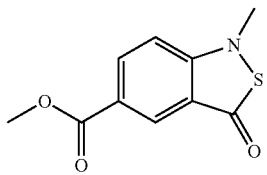

To a solution of Li₂S (5.7 g, 0.124 mol) in H₂O (1000 ml) cooled to 0° C. in an ice bath was added HCl (1M, 186 ml, 0.186 mmol) slowly with stirring. The ice bath was then removed, and 2,4-dioxo-2,4-dihydro-1H-benzo[d][1,3]oxazine-6-carboxylic acid (8.1 g, 0.050 mol) was added slowly. The suspension was stirred for 1 h and was filtered. The filtrate was purged with N₂ for 30 min, and H₂O₂ (30%, 7.0 ml) was added, stirred for 45 min. The pH of the reaction mixture was adjusted with 6M HCl to ~5 and the resulting suspension was filtered. The solid was washed with H₂O (×3) and was dried to yield 3-oxo-1,3-dihydrobenzo[c]isothiazole-5-carboxylic acid as an off-white solid. To a solution of 3-oxo-1,3-dihydrobenzo[c]isothiazole-5-carboxylic acid 4.2 g, 27.8 mmol) in acetone (100 ml) was added MeI (5.2 ml, 83.4 mmol) and K₂CO₃ (7.7 g, 55.6 mmol). The mixture was heated to 60° C. for 2 h, and was filtered and concentrated. The crude product was purified by flash column chromatography on silica gel eluting with 20%→30% EtOAc-hexane to yield Intermediate 9 as a yellow solid.

¹H NMR (300 MHz, CD₃OD) δ ppm 8.39 (d, 1H), 8.20 (dd, J=1.76, 9.08 Hz, 1H), 7.47 (d, J=9.08 Hz, 1H), 3.92 (s, 3H), 3.61 (s, 3H).

Example 10

Intermediate 10

1-Methyl-3-oxo-1,3-dihydrobenzo[c]isothiazole-5-carboxylic acid

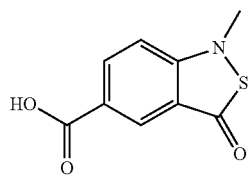

BBr₃ (1M in CH₂Cl₂, 7.0 ml, 7.0 mmol) was added to a solution of Intermediate 9 (157 mg, 0.70 mmol) in CH₂Cl₂ (20 ml), and the reaction was stirred at room temperature for 16 h, quenched with H₂O, extracted with EtOAc (×2). The combined organic layer was washed with brine, dried over Na₂SO₄, and concentrated. The crude product was purified by chromatography on silica gel to yield Intermediate 10.

¹H NMR (300 MHz, CD₃OD) δ ppm 8.41 (s, 1H), 8.22 (d, J=8.79 Hz, 1H), 7.45 (d, J=9.08 Hz, 1H), 3.60 (s, 3H).

Example 11

Intermediate 11

N-(2-amino-4-chlorophenyl)thiophene-2-sulfonamide

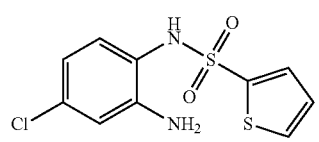 [SMILES: Nc1cc(Cl)ccc1NS(=O)(=O)c1cccs1]

A solution of 4-chloro-2-nitroaniline (1 equiv.) and 2-thiophene sulfonyl chloride (2.5 equiv.) in pyridine was heated at 100° C. for 4 h, MeOH was then added, followed by 4M NaOH (excess), and the reaction was heated at 100° C. for 1 h, cooled to room temperature, acidified with 6M HCl, and extracted with EtOAc (×2). The combined organic layer was washed with brine, dried over Na₂SO₄, and concentrated. The crude product was purified by flash column chromatography on silica gel to yield Intermediate 11.

¹H NMR (300 MHz, acetone) δ ppm 7.87 (dd, 1H), 7.44-7.53 (m, 1H), 7.16 (dd, J=3.81, 4.98 Hz, 1H), 6.82 (d, J=2.34 Hz, 1H), 6.69 (d, J=8.50 Hz, 1H), 6.47 (dd, J=2.34, 8.50 Hz, 1H), 5.00 (br. s., 1H), 2.81 (s, 2H).

The following compounds were prepared following the general procedures described above, in each case the starting materials and the NMR data are specified.

Example 12

Compound 1

1-Methyl-3-oxo-N-(2,2,3,3-tetrafluoro-2,3-dihydrobenzo[b][1,4]dioxin-5-yl)-1,3-dihydrobenzo[c]isothiazole-5-sulfonamide Compound 1 was prepared from 2,2,3,3-tetrafluoro-2,3-dihydrobenzo[b][1,4]dioxin-5-amine and Intermediate 2.

¹H NMR (300 MHz, CD₃OD) δ ppm 8.03 (d, J=2.05 Hz, 1H), 7.88 (dd, J=2.05, 9.08 Hz, 1H), 7.46 (d, J=9.08 Hz, 1H), 7.38 (dd, J=1.47, 8.20 Hz, 1H), 7.23 (t, J=8.35 Hz, 1H), 7.08 (dd, J=1.47, 8.50 Hz, 1H), 3.57 (s, 3H).

Example 13

Compound 2

N-(2,3-dimethoxyphenyl)-1-methyl-3-oxo-1,3-dihydro-2,1-benzisothiazolesulfonamide

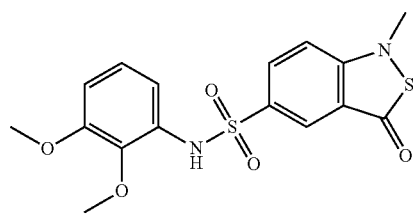

Compound 2 was prepared from 2,3-dimethoxyaniline and Intermediate 2.

$^1$H NMR (300 MHz, CD$_3$OD): δ ppm 8.13 (d, J=2.1 Hz, 1H), 7.93 (dd, J=9.1, 2.1 Hz, 1H), 7.44 (d, J=9.1 Hz, 1H), 7.13 (dd, J=8.5, 1.5 Hz, 1H), 6.96 (t, J=8.4 Hz, 1H), 6.75 (dd, J=8.2, 1.5 Hz, 1H), 3.76 (s, 3H), 3.56 (s, 3H), 3.51 ppm (s, 3H).

Example 14

Compound 3

N-(2,3-dihydro-1,4-benzodioxin-5-yl)-1-methyl-3-oxo-1,3-dihydro-2,1-benzisothiazole-5-sulfonamide

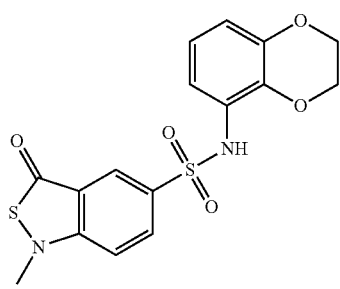 [SMILES: Cn1sc(=O)c2cc(S(=O)(=O)Nc3cccc4c3OCCO4)ccc21]

Compound 3 was prepared from 2,3-dihydrobenzo[b][1,4]dioxin-5-amine and Intermediate 2.

$^1$H NMR (300 MHz, acetone-d$_6$): δ ppm 8.21 (s, 1H), 8.12 (d, J=2.1 Hz, 1H), 7.94 (dd, J=9.1, 2.1 Hz, 1H), 7.54 (d, J=8.8 Hz, 1H), 7.03 (dd, J=7.9, 1.5 Hz, 1H), 6.76 (t, J=8.2 Hz, 1H), 6.60 (dd, J=8.2, 1.5 Hz, 1H), 3.98-4.16 (m, 4H), 3.64 ppm (s, 3H).

Example 15

Compound 4

1-isopropyl-3-oxo-N-{2-[(2-thienylsulfonyl)amino]phenyl}-1,3-dihydro-2,1-benzisothiazole-5-sulfonamide

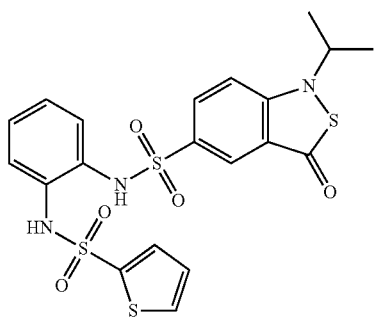 [SMILES: CC(C)n1sc(=O)c2cc(S(=O)(=O)Nc3ccccc3NS(=O)(=O)c3cccs3)ccc21]

Compound 4 was prepared from benzene-1,2-diamine, thiophene-2-sulfonyl chloride, and Intermediate 3.

$^1$H NMR (300 MHz, CHLOROFORM-d) δ ppm 8.16 (d, J=2.05 Hz, 1H), 7.84 (dd, J=2.05, 9.08 Hz, 1H), 7.59 (d, J=4.10 Hz, 1H), 7.42 (dd, J=1.47, 3.81 Hz, 1H), 7.21 (d, J=9.38 Hz, 1H), 7.00-7.15 (m, 7H), 4.67 (dt, J=6.48, 13.11 Hz, 1H), 4.12 (q, J=7.13 Hz, 1H), 1.43 (d, J=6.74 Hz, 6H).

Example 16

Compound 5

N-(2,2-difluoro-1,3-benzodioxol-4-yl)-1-methyl-3-oxo-1,3-dihydro-2,1-benzisothiazole-5-sulfonamide

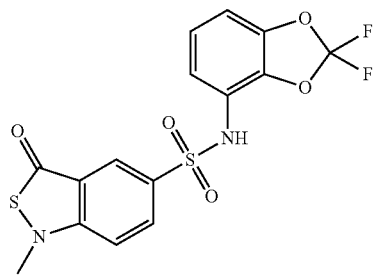 [SMILES: Cn1sc(=O)c2cc(S(=O)(=O)Nc3cccc4c3OC(F)(F)O4)ccc21]

Compound 5 was prepared from 2,2-difluorobenzo[d][1,3]dioxol-4-amine and Intermediate 2.

¹H NMR (300 MHz, CD₃OD): δ ppm=8.09 (d, J=2.1 Hz, 1H), 7.90 (dd, J=9.1, 2.1 Hz, 1H), 7.49 (d, J=9.1 Hz, 1H), 7.10-7.13 (m, 1H), 7.08 (s, 1H), 6.98 (dd, J=7.6, 1.8 Hz, 1H), 3.58 ppm (s, 3H).

Example 17

Compound 6

1-methyl-3-oxo-N-{2-[(2-thienylsulfonyl)amino]pyridin-3-yl}-1,3-dihydro-2,1-benzisothiazole-5-sulfonamide

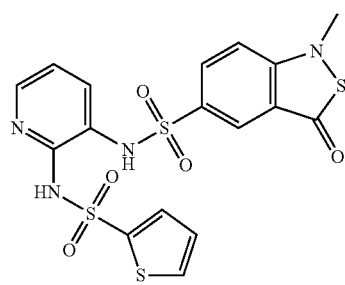 [SMILES: Cn1sc(=O)c2cc(S(=O)(=O)Nc3cccnc3NS(=O)(=O)c3cccs3)ccc21]

Compound 6 was prepared from 2-chloro-3-nitropyridine, thiophene-2-sulfonamide, and Intermediate 2.

¹H NMR (300 MHz, DMSO-d₆) δ ppm 9.27-9.56 (m, 1H), 7.42-8.11 (m, 8H), 6.68-7.15 (m, 2H), 3.58 (s, 3H).

Example 18

Compound 7

N-{5-chloro-2-[(2-thienylsulfonyl)amino]phenyl}-1-methyl-3-oxo-1,3-dihydro-2,1-benzisothiazole-5-sulfonamide

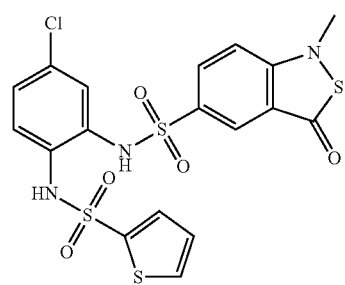 [SMILES: Cn1sc(=O)c2cc(S(=O)(=O)Nc3cc(Cl)ccc3NS(=O)(=O)c3cccs3)ccc21]

Compound 7 was prepared from 4-chloro-2-nitroaniline, thiophene-2-sulfonyl chloride, and Intermediate 2.

¹H NMR (300 MHz, CD₃OD) δ ppm 8.02 (d, 1H), 7.87 (dd, J=1.76, 9.08 Hz, 1H), 7.77 (dd, J=1.17, 4.98 Hz, 1H), 7.49 (d, J=9.08 Hz, 1H), 7.38-7.43 (m, 1H), 7.18 (d, J=2.34 Hz, 1H), 7.00-7.11 (m, 2H), 6.87 (d, J=8.50 Hz, 1H), 3.59 (s, 3H).

Example 19

Compound 8

N-{4-chloro-2-[(2-thienylsulfonyl)amino]phenyl}-1-methyl-3-oxo-1,3-dihydro-2,1-benzisothiazole-5-sulfonamide

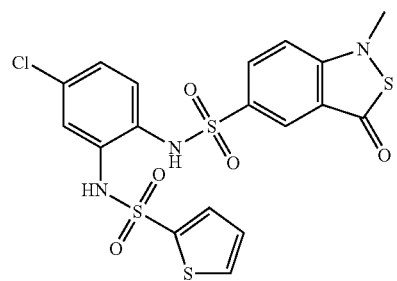 [SMILES: Cn1sc(=O)c2cc(S(=O)(=O)Nc3ccc(Cl)cc3NS(=O)(=O)c3cccs3)ccc21]

Compound 8 was prepared from 5-chloro-2-nitroaniline, thiophene-2-sulfonyl chloride, and Intermediate 2.

¹H NMR (300 MHz, CD₃OD) δ ppm 7.99 (d, 1H), 7.74-7.84 (m, 2H), 7.46 (dd, J=3.66, 4.83 Hz, 2H), 6.99-7.13 (m, 4H), 3.58 (s, 3H).

Example 20

Compound 9

N-1,3-benzodioxol-4-yl-1-methyl-3-oxo-1,3-dihydro-2,1-benzisothiazole-5-sulfonamide

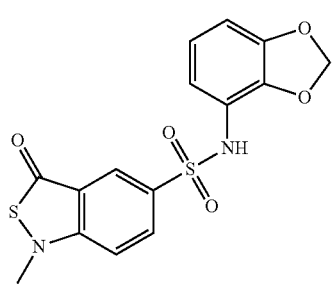 [SMILES: Cn1sc(=O)c2cc(S(=O)(=O)Nc3cccc4c3OCO4)ccc21]

Compound 9 was prepared from benzo[d][1,3]dioxol-4-amine and Intermediate 2.

¹H NMR (300 MHz, CDCl₃): δ ppm=8.34 (d, J=2.1 Hz, 1H), 7.90 (dd, J=8.9, 1.9 Hz, 1H), 7.16 (d, J=9.1 Hz, 1H), 6.99

(d, J=8.5 Hz, 1H), 6.72-6.82 (m, 1H), 6.61 (d, J=8.8 Hz, 1H), 5.83 (br. s., 2H), 3.54 ppm (s, 3H).

Example 21

Compound 10

N-[2-({[4-chloro-3-(trifluoromethyl)phenyl]sulfonyl}amino)phenyl]-1-methyl-3-oxo-1,3-dihydro-2,1-benzisothiazole-5-sulfonamide

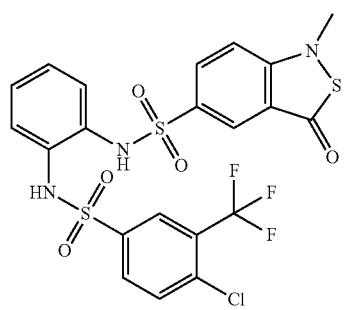 [SMILES: Cn1sc(=O)c2cc(S(=O)(=O)Nc3ccccc3NS(=O)(=O)c3ccc(Cl)c(C(F)(F)F)c3)ccc21]

Compound 10 was prepared from benzene-1,2-diamine, 4-chloro-3-(trifluoromethyl)benzene-1-sulfonyl chloride, and Intermediate 2.

$^1$H NMR (300 MHz, CDCl$_3$): δ ppm=8.31 (s, 1H), 8.04 (d, J=1.8 Hz, 1H), 7.88-7.96 (m, 2H), 7.76 (dd, J=8.4, 2.2 Hz, 1H), 7.63 (dd, J=8.9, 1.9 Hz, 1H), 7.51 (d, J=8.2 Hz, 1H), 6.89-7.17 (m, 4H), 6.79 (dd, J=7.9, 1.5 Hz, 1H), 3.47 ppm (s, 3H).

Example 22

Compound 11

1-isopropyl-3-oxo-N-(2,2,3,3-tetrafluoro-2,3-dihydro-1,4-benzodioxin-5-yl)-1,3-dihydro-2,1-benzisothiazole-5-sulfonamide

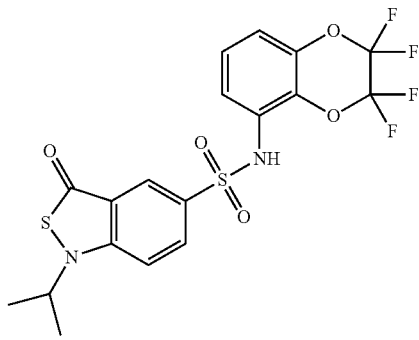 [SMILES: CC(C)n1sc(=O)c2cc(S(=O)(=O)Nc3cccc4c3OC(F)(F)C(F)(F)O4)ccc21]

Compound 11 was prepared from 2,2,3,3-tetrafluoro-2,3-dihydrobenzo[b][1,4]dioxin-5-amine and Intermediate 3.

$^1$H NMR (300 MHz, CDCl$_3$) δ ppm 8.22 (d, J=1.47 Hz, 1H), 7.86 (dd, J=2.05, 9.08 Hz, 1H), 7.45 (dd, J=1.47, 8.20 Hz, 1H), 7.12-7.25 (m, 2H), 6.92 (dd, J=1.47, 8.50 Hz, 1H), 6.80 (s, 1H), 4.65 (d, J=6.45 Hz, 1H), 1.43 (d, J=6.45 Hz, 6H).

Example 23

Compound 12

N-{4,5-dichloro-2-[(2-thienylsulfonyl)amino]phenyl}-1-methyl-3-oxo-1,3-dihydro-2,1-benzisothiazole-5-sulfonamide

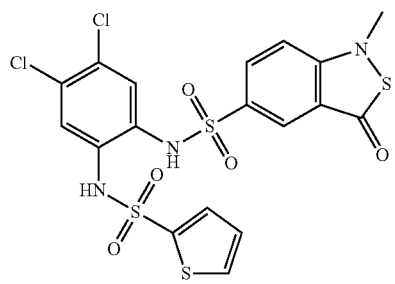

Compound 12 was prepared from 4,5-dichlorobenzene-1,2-diamine, thiophene-2-sulfonamide, and Intermediate 2.

$^1$H NMR (300 MHz, DMSO-d$_6$) δ ppm 9.36-10.08 (m, 1H), 7.93-8.04 (m, 1H), 7.84 (dd, J=2.05, 9.08 Hz, 1H), 7.63 (d, J=9.08 Hz, 1H), 7.54 (dd, J=1.17, 3.81 Hz, 1H), 7.33 (s, 1H), 7.10-7.21 (m, 2H), 3.60 (s, 3H).

Example 24

Compound 13

N-{5-chloro-2-[(2-thienylsulfonyl)amino]pyridin-3-yl}-1-methyl-3-oxo-1,3-dihydro-2,1-benzisothiazole-5-sulfonamide

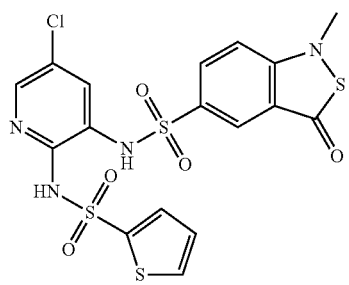 [SMILES: Cn1sc(=O)c2cc(S(=O)(=O)Nc3cc(Cl)cnc3NS(=O)(=O)c3cccs3)ccc21]

Compound 13 was prepared from 2-bromo-5-chloro-3-nitropyridine, thiophene-2-sulfonamide, and Intermediate 2.

$^1$H NMR (300 MHz, DMSO-d$_6$) δ ppm 8.07-8.15 (m, 1H), 7.94 (s, 1H), 7.87-7.92 (m, 1H), 7.76-7.82 (m, 1H), 7.68-7.73

(m, 1H), 7.64-7.68 (m, 1H), 7.61-7.64 (m, 1H), 7.60 (s, 1H), 7.57 (s, 1H), 7.08 (dd, J=3.81, 4.98 Hz, 2H), 3.59 (s, 3H).

Example 25

Compound 14

1-methyl-3-oxo-N-[3-(trifluoromethoxy)phenyl]-1,3-dihydro-2,1-benzisothiazole-5-sulfonamide

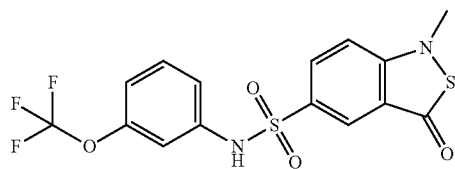 [SMILES: Cn1sc(=O)c2cc(S(=O)(=O)Nc3cccc(OC(F)(F)F)c3)ccc21]

Compound 14 was prepared from 3-(trifluoromethoxy)aniline and Intermediate 2.

¹H NMR (300 MHz, CD₃OD): δ ppm=8.14 (d, J=2.1 Hz, 1H), 7.90 (dd, J=9.1, 2.1 Hz, 1H), 7.47 (d, J=9.1 Hz, 1H), 7.24-7.36 (m, 1H), 7.06 (s, 2H), 6.88-6.98 (m, 1H), 3.56 ppm (s, 4H).

Example 26

Compound 15

N-dibenzo[b,e][1,4]dioxin-1-yl-1-methyl-3-oxo-1,3-dihydro-2,1-benzisothiazole-5-sulfonamide

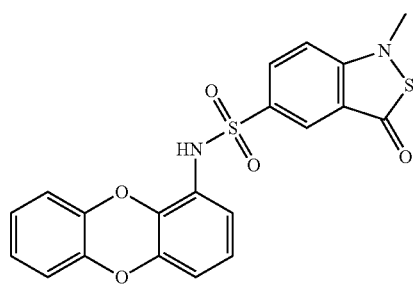 [SMILES: Cn1sc(=O)c2cc(S(=O)(=O)Nc3cccc4c3Oc3ccccc3O4)ccc21]

Compound 15 was prepared from Intermediate 5 and Intermediate 2.

¹H NMR (300 MHz, CD₃OD): δ ppm=8.15 (d, J=2.1 Hz, 1H), 7.80 (dd, J=9.1, 2.1 Hz, 1H), 7.28 (d, J=9.1 Hz, 0H), 7.08 (dd, J=8.2, 1.5 Hz, 0H), 6.66-6.94 (m, 5H), 6.57 (dd, J=8.1, 1.6 Hz, 0H), 3.41 ppm (s, 3H).

Example 27

Compound 16

N-(7-chloro-2,3-dihydro-1,4-benzodioxin-5-yl)-1-methyl-3-oxo-1,3-dihydro-2,1-benzisothiazole-5-sulfonamide

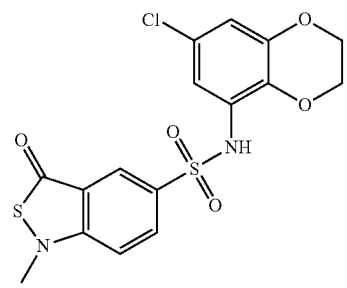 [SMILES: Cn1sc(=O)c2cc(S(=O)(=O)Nc3cc(Cl)cc4c3OCCO4)ccc21]

7-chloro-2,3-dihydrobenzo[b][1,4]dioxin-5-amine (CAS 698985-25-0, 12 mg, 0.066 mmol) and Intermediate 2 (17 mg, 0.066 mmol) in pyridine was heated at 100° C. for 3 hours and yielded Compound 16 as a light yellow solid (7 mg, 25%).

¹H NMR (300 MHz, CDCl₃): δ ppm=8.34 (d, J=2.1 Hz, 1H), 7.93 (dd, J=9.1, 2.1 Hz, 1H), 7.18 (d, J=8.8 Hz, 1H), 7.10 (d, J=2.3 Hz, 1H), 6.95 (s, 1H), 6.61 (d, J=2.3 Hz, 1H), 4.04-4.24 (m, 4H), 3.54 ppm (s, 3H).

Example 28

Compound 17

N-(2-{[(5-chloro-2-thienyl)sulfonyl]amino}phenyl)-1-methyl-3-oxo-1,3-dihydro-2,1-benzisothiazole-5-sulfonamide

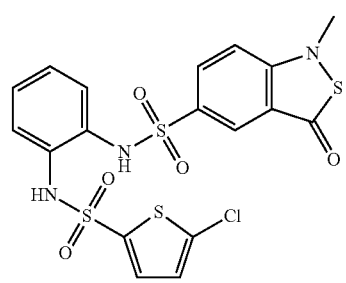 [SMILES: Cn1sc(=O)c2cc(S(=O)(=O)Nc3ccccc3NS(=O)(=O)c3ccc(Cl)s3)ccc21]

Compound 17 was prepared from benzene-1,2-diamine, 5-chlorothiophene-2-sulfonyl chloride, and Intermediate 2.

¹H NMR (300 MHz, DMSO-d₆) δ ppm 9.56-9.65 (m, 1H), 9.28-9.38 (m, 1H), 7.95 (d, J=1.47 Hz, 1H), 7.84 (dd, J=2.05, 9.08 Hz, 1H), 7.62 (d, J=8.79 Hz, 1H), 7.39 (d, J=4.10 Hz, 1H), 7.21 (d, J=4.10 Hz, 1H), 7.04-7.15 (m, 4H), 3.59 (s, 3H).

Example 29

Compound 18

N-(2-{[(4,5-dichloro-2-thienyl)sulfonyl]amino}phenyl)-1-methyl-3-oxo-1,3-dihydro-2,1-benzisothiazole-5-sulfonamide

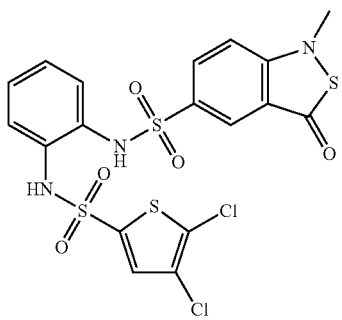 [SMILES: Cn1sc(=O)c2cc(S(=O)(=O)Nc3ccccc3NS(=O)(=O)c3cc(Cl)c(Cl)s3)ccc21]

Compound 18 was prepared from benzene-1,2-diamine, 4,5-dichlorothiophene-2-sulfonyl chloride, and Intermediate 2.

$^1$H NMR (300 MHz, DMSO-$d_6$) δ ppm 9.66-9.84 (m, 1H), 9.38 (d, J=1.47 Hz, 1H), 7.96 (d, J=2.05 Hz, 1H), 7.86 (dd, J=2.05, 8.79 Hz, 1H), 7.62 (d, J=10.26 Hz, 2H), 7.08-7.18 (m, 3H), 7.03 (dd, J=3.96, 6.89 Hz, 1H), 3.59 (s, 3H).

Example 30

Compound 19

1-methyl-3-oxo-N-{2-[(phenylsulfonyl)amino]phenyl}-1,3-dihydro-2,1-benzisothiazole-5-sulfonamide

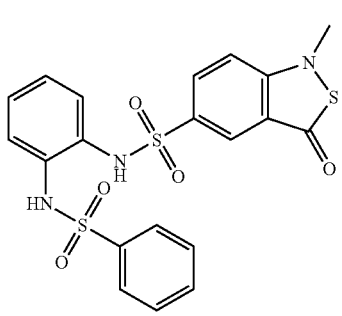 [SMILES: Cn1sc(=O)c2cc(S(=O)(=O)Nc3ccccc3NS(=O)(=O)c3ccccc3)ccc21]

Compound 19 was prepared from benzene-1,2-diamine, benzenesulfonyl chloride, and Intermediate 2.

$^1$H NMR (300 MHz, CDCl$_3$): δ ppm=8.15 (d, J=1.5 Hz, 1H), 7.84 (dd, J=9.1, 2.1 Hz, 1H), 7.63-7.75 (m, 2H), 7.35-7.62 (m, 3H), 7.20 (d, J=8.8 Hz, 1H), 6.81-7.12 (m, 4H), 3.53 ppm (s, 3H).

Example 31

Compound 20

N-(2-{[(4-chlorophenyl)sulfonyl]amino}phenyl)-1-methyl-3-oxo-1,3-dihydro-2,1-benzisothiazole-5-sulfonamide

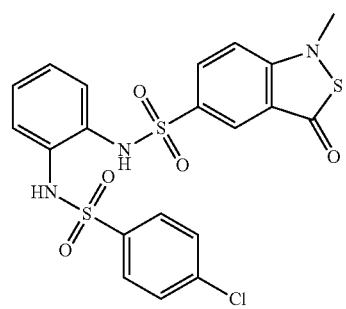 [SMILES: Cn1sc(=O)c2cc(S(=O)(=O)Nc3ccccc3NS(=O)(=O)c3ccc(Cl)cc3)ccc21]

Compound 20 was prepared from benzene-1,2-diamine, 4-chlorobenzene-1-sulfonyl chloride, and Intermediate 2.

$^1$H NMR (300 MHz, CD$_3$OD): δ ppm=7.96 (d, J=2.1 Hz, 1H), 7.82 (dd, J=9.1, 1.8 Hz, 1H), 7.58-7.69 (m, 2H), 7.41-7.54 (m, 3H), 7.02-7.13 (m, 3H), 6.91-7.02 (m, 2H), 3.58 ppm (s, 3H).

Example 32

Compound 21

N-{2-[(2-furylsulfonyl)amino]phenyl}-1-methyl-3-oxo-1,3-dihydro-2,1-benzisothiazole-5-sulfonamide

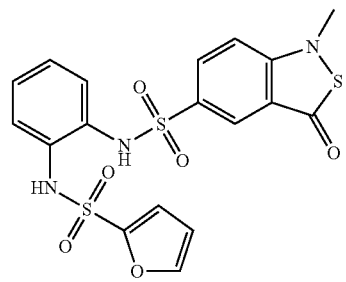 [SMILES: Cn1sc(=O)c2cc(S(=O)(=O)Nc3ccccc3NS(=O)(=O)c3ccco3)ccc21]

Compound 21 was prepared from benzene-1,2-diamine, furan-2-sulfonyl chloride, and Intermediate 2.

$^1$H NMR (300 MHz, CDCl$_3$): δ ppm=8.20 (d, J=2.1 Hz, 1H), 7.87 (dd, J=9.1, 1.8 Hz, 1H), 7.61 (br. s., 1H), 7.21 (d, J=8.8 Hz, 1H), 7.02-7.16 (m, 4H), 6.91 (d, J=3.5 Hz, 1H), 6.45 (dd, J=3.5, 2.1 Hz, 1H), 3.55 ppm (s, 3H).

Example 33

Compound 22

N-{5-bromo-2-[(2-thienylsulfonyl)amino]phenyl}-1-methyl-3-oxo-1,3-dihydro-2,1-benzisothiazole-5-sulfonamide

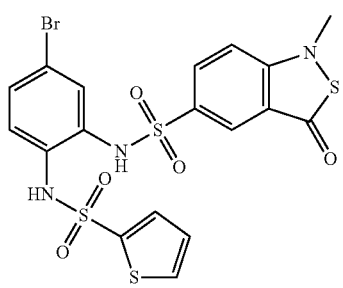 [SMILES: Cn1sc(=O)c2cc(S(=O)(=O)Nc3cc(Br)ccc3NS(=O)(=O)c3cccs3)ccc21]

Compound 22 was prepared from 4-bromo-2-nitroaniline, thiophene-2-sulfonyl chloride, and Intermediate 2.

$^1$H NMR (300 MHz, METHANOL-$d_4$) δ ppm 8.01 (d, J=1.76 Hz, 1H), 7.83-7.89 (m, 1H), 7.75-7.80 (m, 1H), 7.45-7.52 (m, 1H), 7.40-7.45 (m, 1H), 7.29 (d, J=2.05 Hz, 1H), 7.17-7.23 (m, 1H), 7.06-7.11 (m, 1H), 6.84 (d, J=8.50 Hz, 1H), 3.58 (s, 3H).

Example 34

Compound 23

1-methyl-3-oxo-N-{2-[(2-thienylsulfonyl)amino]-5-(trifluoromethyl)phenyl}-1,3-dihydro-2,1-benzisothiazole-5-sulfonamide

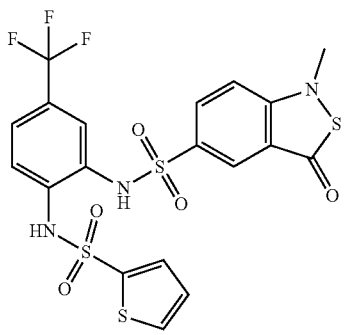 [SMILES: Cn1sc(=O)c2cc(S(=O)(=O)Nc3cc(C(F)(F)F)ccc3NS(=O)(=O)c3cccs3)ccc21]

Compound 23 was prepared from 2-nitro-4-(trifluoromethyl)aniline, thiophene-2-sulfonyl chloride, and Intermediate 2.

$^1$H NMR (300 MHz, CD$_3$OD) δ ppm 7.95 (d, J=2.05 Hz, 1H), 7.77-7.85 (m, 2H), 7.53 (dd, J=1.17, 3.81 Hz, 1H), 7.48 (d, J=9.08 Hz, 1H), 7.36-7.43 (m, 1H), 7.29-7.33 (m, 1H), 7.23 (d, J=2.05 Hz, 1H), 7.10 (dd, J=3.81, 4.98 Hz, 1H), 3.59 (s, 3H).

Example 35

Compound 24

1-methyl-N-(2-{[(1-methyl-1H-imidazol-4-yl)sulfonyl]amino}phenyl)-3-oxo-1,3-dihydro-2,1-benzisothiazole-5-sulfonamide

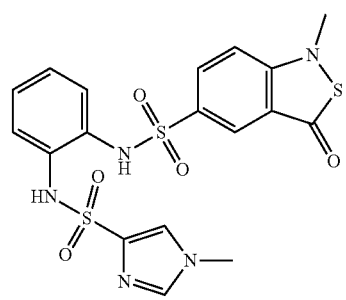 [SMILES: Cn1cnc(S(=O)(=O)Nc2ccccc2NS(=O)(=O)c2ccc3c(c2)c(=O)sn3C)c1]

Compound 24 was prepared from benzene-1,2-diamine, 1-methyl-1H-imidazole-4-sulfonyl chloride, and Intermediate 2.

$^1$H NMR (300 MHz, DMSO-$d_6$) δ ppm 9.57 (br. s., 1H), 9.32 (br. s., 1H), 7.91-7.95 (m, 1H), 7.84-7.89 (m, 1H), 7.81-7.84 (m, 1H), 7.75-7.79 (m, 1H), 7.53-7.65 (m, 1H), 6.95-7.23 (m, 4H), 3.67 (s, 3H), 3.57 (s, 3H).

Example 36

Compound 25

1-methyl-N-(2-{[(1-methyl-1H-pyrazol-3-yl)sulfonyl]amino}phenyl)-3-oxo-1,3-dihydro-2,1-benzisothiazole-5-sulfonamide

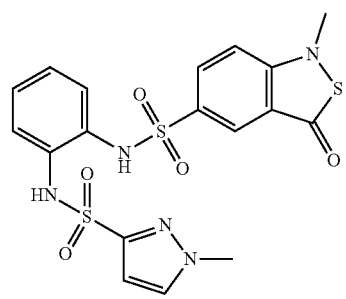 [SMILES: Cn1ccc(S(=O)(=O)Nc2ccccc2NS(=O)(=O)c2ccc3c(c2)c(=O)sn3C)n1]

Compound 25 was prepared from benzene-1,2-diamine, 1-methyl-1H-pyrazole-3-sulfonyl chloride, and Intermediate 2.

$^1$H NMR (300 MHz, CD$_3$OD): δ ppm=7.98 (d, J=2.1 Hz, 1H), 7.82 (dd, J=9.1, 1.5 Hz, 1H), 7.67 (d, J=2.3 Hz, 1H), 7.43

(d, J=9.1 Hz, 1H), 7.00-7.23 (m, 4H), 6.54 (d, J=2.3 Hz, 1H), 3.97 (s, 3H), 3.56 ppm (s, 3H).

Example 37

Compound 26

1-methyl-N-(2-{[(1-methyl-1H-pyrazol-4-yl)sulfonyl]amino}phenyl)-3-oxo-1,3-dihydro-2,1-benzisothiazole-5-sulfonamide

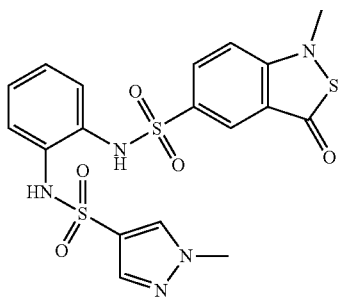 [SMILES: Cn1cc(S(=O)(=O)Nc2ccccc2NS(=O)(=O)c2ccc3c(c2)c(=O)sn3C)cn1]

Compound 26 was prepared from benzene-1,2-diamine, 1-methyl-1H-pyrazole-4-sulfonyl chloride, and Intermediate 2.

$^1$H NMR (300 MHz, DMSO-d$_6$) δ ppm 9.31 (br. s., 1H), 9.06 (br. s., 1H), 8.20 (s, 1H), 7.90 (d, J=1.76 Hz, 1H), 7.81 (dd, J=2.05, 9.08 Hz, 1H), 7.59-7.65 (m, 2H), 6.98-7.15 (m, 4H), 3.82 (s, 3H), 3.59 (s, 3H).

Example 38

Compound 27

1-methyl-N-{4-methyl-2-[(2-thienylsulfonyl)amino]phenyl}-3-oxo-1,3-dihydro-2,1-benzisothiazole-5-sulfonamide

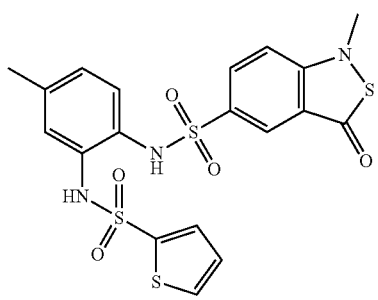 [SMILES: Cc1ccc(NS(=O)(=O)c2ccc3c(c2)c(=O)sn3C)c(NS(=O)(=O)c2cccs2)c1]

Compound 27 was prepared from 2-fluoro-4-methyl-1-nitrobenzene, thiophene-2-sulfonamide, and Intermediate 2.

$^1$H NMR (300 MHz, DMSO-d$_6$) δ ppm=9.29 (br. s., 1H), 9.16 (br. s., 1H), 7.98-7.88 (m, 2H), 7.78 (dd, J=1.8, 9.1 Hz, 1H), 7.61 (d, J=9.1 Hz, 1H), 7.50 (d, J=2.9 Hz, 1H), 7.13 (t, J=4.4 Hz, 1H), 6.97-6.83 (m, 3H), 3.31 (s, 3H), 2.13 (s, 3H).

Example 39

Compound 28

N-{4-chloro-2-[(2-thienylsulfonyl)amino]-5-(trifluoromethyl)phenyl}-1-methyl-3-oxo-1,3-dihydro-2,1-benzisothiazole-5-sulfonamide

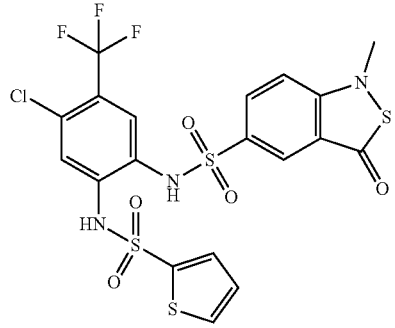 [SMILES: Cn1sc(=O)c2cc(S(=O)(=O)Nc3cc(C(F)(F)F)c(Cl)cc3NS(=O)(=O)c3cccs3)ccc21]

Compound 28 was prepared from 1,5-dichloro-2-nitro-4-(trifluoromethyl)benzene, thiophene-2-sulfonamide, and Intermediate 2.

$^1$H NMR (300 MHz, DMSO-d$_6$) δ ppm=7.96 (d, J=5.0 Hz, 1H), 7.93 (d, J=1.8 Hz, 1H), 7.77 (dd, J=2.1, 9.1 Hz, 1H), 7.66-7.59 (m, 2H), 7.41 (d, J=4.4 Hz, 2H), 7.18-7.12 (m, 1H), 3.36 (br. s., 2H).

Example 40

Compound 29

N-{5-methoxy-2-[(2-thienylsulfonyl)amino]phenyl}-1-methyl-3-oxo-1,3-dihydro-2,1-benzisothiazole-5-sulfonamide

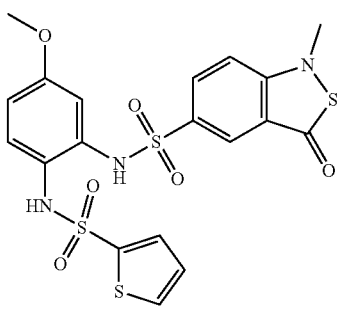 [SMILES: COc1ccc(NS(=O)(=O)c2cccs2)c(NS(=O)(=O)c2ccc3c(c2)c(=O)sn3C)c1]

Compound 29 was prepared from 4-methoxy-2-nitroaniline, thiophene-2-sulfonyl chloride, and Intermediate 2.

$^1$H NMR (300 MHz, DMSO-d$_6$) δ ppm=8.02 (d, 1H), 7.97-7.92 (m, 1H), 7.89 (dd, J=1.8, 9.1 Hz, 1H), 7.63 (d, J=9.1 Hz, 1H), 7.41 (dd, J=1.3, 3.7 Hz, 1H), 7.16-7.11 (m, 1H), 6.79

(d, J=8.8 Hz, 1H), 6.71 (d, J=2.6 Hz, 1H), 6.58 (dd, J=2.6, 8.8 Hz, 1H), 3.62 (s, 3H), 3.59 (s, 3H).

Example 41

Compound 30

1-methyl-3-oxo-N-{2-[(pyridin-3-ylsulfonyl)amino]phenyl}-1,3-dihydro-2,1-benzisothiazole-5-sulfonamide

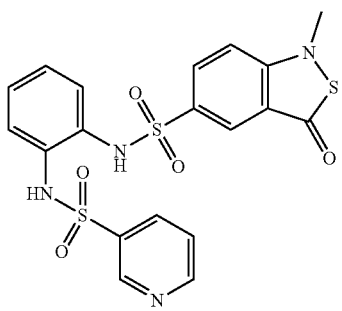 [SMILES: Cn1sc(=O)c2cc(S(=O)(=O)Nc3ccccc3NS(=O)(=O)c3cccnc3)ccc21]

Compound 30 was prepared from benzene-1,2-diamine, pyridine-3-sulfonyl chloride, and Intermediate 2

$^1$H NMR (300 MHz, CD$_3$OD): δ ppm=8.65-8.82 (m, 2H), 8.08 (dddd, 1H), 7.93 (d, J=2.1 Hz, 1H), 7.79 (dd, J=9.1, 2.1 Hz, 1H), 7.54 (dd, J=8.2, 5.0 Hz, 1H), 7.45 (d, J=9.1 Hz, 1H), 7.00-7.16 (m, 4H), 6.84-7.00 (m, 1H), 3.58 ppm (s, 3H).

Example 42

Compound 31

1-methyl-3-oxo-N-{2-[(4H-1,2,4-triazol-3-ylsulfonyl)amino]phenyl}-1,3-dihydro-2,1-benzisothiazole-5-sulfonamide

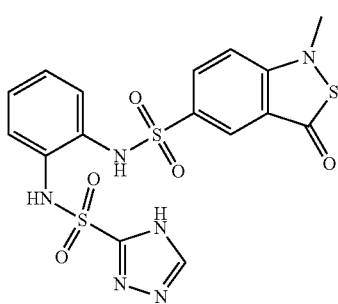 [SMILES: Cn1sc(=O)c2cc(S(=O)(=O)Nc3ccccc3NS(=O)(=O)c3nnc[nH]3)ccc21]

Compound 31 was prepared from benzene-1,2-diamine, 4H-1,2,4-triazole-3-sulfonyl chloride, and Intermediate 2.

$^1$H NMR (300 MHz, CD$_3$OD): δ ppm=8.52 (s, 1H), 7.89 (d, J=1.8 Hz, 1H), 7.66 (dd, J=9.1, 2.1 Hz, 1H), 7.36-7.55 (m, 5H), 3.60 ppm (s, 3H).

Example 43

Compound 32

N-{2-[(1H-imidazol-4-ylsulfonyl)amino]phenyl}-1-methyl-3-oxo-1,3-dihydro-2,1-benzisothiazole-5-sulfonamide

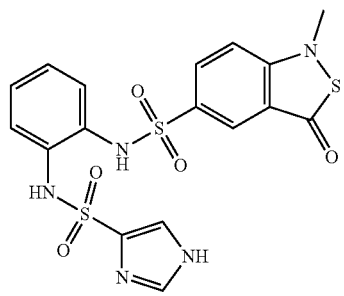 [SMILES: Cn1sc(=O)c2cc(S(=O)(=O)Nc3ccccc3NS(=O)(=O)c3c[nH]cn3)ccc21]

Compound 32 was prepared from benzene-1,2-diamine, 1H-imidazole-5-sulfonyl chloride, and Intermediate 2.

$^1$H NMR (300 MHz, CD$_3$OD): δ ppm=8.00 (d, J=1.8 Hz, 1H), 7.87 (dd, J=9.1, 2.1 Hz, 1H), 7.81 (d, J=1.2 Hz, 1H), 7.53 (d, J=1.2 Hz, 1H), 7.45 (d, J=9.1 Hz, 1H), 7.19 (d, J=7.6 Hz, 1H), 6.99-7.13 (m, 3H), 3.57 ppm (s, 3H).

Example 44

Compound 33

N-(2-{[(3,4-dichlorophenyl)sulfonyl]amino}phenyl)-1-methyl-3-oxo-1,3-dihydro-2,1-benzisothiazole-5-sulfonamide

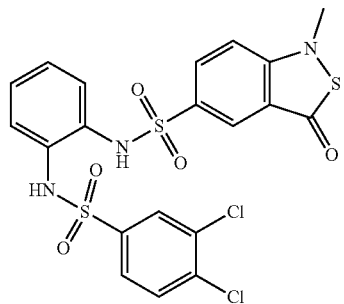 [SMILES: Cn1sc(=O)c2cc(S(=O)(=O)Nc3ccccc3NS(=O)(=O)c3ccc(Cl)c(Cl)c3)ccc21]

Compound 33 was prepared from benzene-1,2-diamine, 3,4-dichlorobenzene-1-sulfonyl chloride, and Intermediate 2.

¹H NMR (300 MHz, DMSO-d6): δ ppm=9.51 (br. s., 1H), 9.32 (br. s., 1H), 7.94 (d, J=1.8 Hz, 1H), 7.80-7.89 (m, 3H), 7.56-7.70 (m, 2H), 6.90-7.13 (m, 4H), 3.59 ppm (s, 3H).

Example 45

Compound 34

N-(2-{[(2,5-dichlorophenyl)sulfonyl]amino}phenyl)-1-methyl-3-oxo-1,3-dihydro-2,1-benzisothiazole-5-sulfonamide

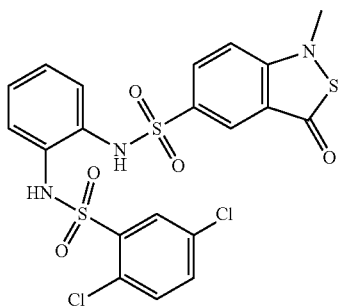 [SMILES: Cn1sc(=O)c2cc(S(=O)(=O)Nc3ccccc3NS(=O)(=O)c3cc(Cl)ccc3Cl)ccc21]

Compound 34 was prepared from benzene-1,2-diamine, 2,5-dichlorobenzene-1-sulfonyl chloride, and Intermediate 2.

¹H NMR (300 MHz, CD₃OD): δ ppm=8.01 (d, J=1.8 Hz, 1H), 7.83 (dd, J=9.1, 2.1 Hz, 1H), 7.71 (d, J=2.3 Hz, 1H), 7.53-7.64 (m, 2H), 7.46 (d, J=9.4 Hz, 1H), 7.12-7.21 (m, 1H), 6.99-7.12 (m, 2H), 6.90 (dd, J=7.5, 1.9 Hz, 1H), 3.58 ppm (s, 3H).

Example 46

Compound 35

N-(2-{[(2-chlorophenyl)sulfonyl]amino}phenyl)-1-methyl-3-oxo-1,3-dihydro-2,1-benzisothiazole-5-sulfonamide

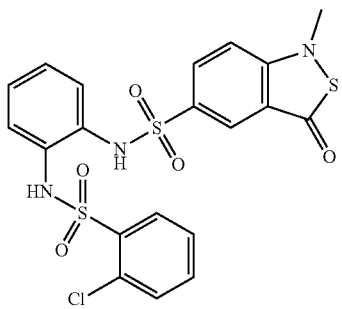 [SMILES: Cn1sc(=O)c2cc(S(=O)(=O)Nc3ccccc3NS(=O)(=O)c3ccccc3Cl)ccc21]

Compound 35 was prepared from benzene-1,2-diamine, 2-chlorobenzene-1-sulfonyl chloride, and Intermediate 2.

¹H NMR (600 MHz, DMSO-d₆): δ ppm=9.46 (br. s., 1H), 9.43 (br. s., 1H), 7.93 (d, J=1.8 Hz, 1H), 7.88 (dd, J=7.8, 1.3 Hz, 1H), 7.81 (dd, J=9.1, 1.8 Hz, 1H), 7.63-7.72 (m, 2H), 7.61 (d, J=9.4 Hz, 1H), 7.45-7.52 (m, 1H), 6.93-7.07 (m, 4H), 3.59 ppm (s, 3H).

Example 47

Compound 36

N-(2-{[(2-fluorophenyl)sulfonyl]amino}phenyl)-1-methyl-3-oxo-1,3-dihydro-2,1-benzisothiazole-5-sulfonamide

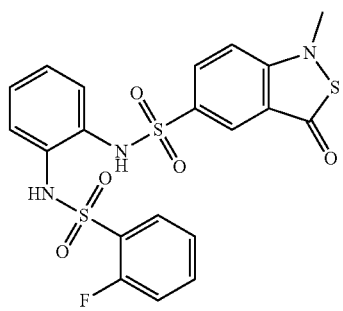 [SMILES: Cn1sc(=O)c2cc(S(=O)(=O)Nc3ccccc3NS(=O)(=O)c3ccccc3F)ccc21]

Compound 36 was prepared from benzene-1,2-diamine, 2-fluorobenzene-1-sulfonyl chloride, and Intermediate 2.

¹H NMR (300 MHz, DMSO-d₆): δ ppm=9.53 (br. s., 1H), 9.36 (br. s., 1H), 7.92 (d, J=1.8 Hz, 1H), 7.81 (dd, J=9.1, 2.1 Hz, 1H), 7.65-7.77 (m, 2H), 7.61 (d, J=9.1 Hz, 1H), 7.38-7.50 (m, 1H), 7.26-7.37 (m, 1H), 7.03 (s, 4H), 3.59 ppm (s, 3H).

Example 48

Compound 37

N-[2-({[3,5-bis(trifluoromethyl)phenyl]sulfonyl}amino)phenyl]-1-methyl-3-oxo-1,3-dihydro-2,1-benzisothiazole-5-sulfonamide

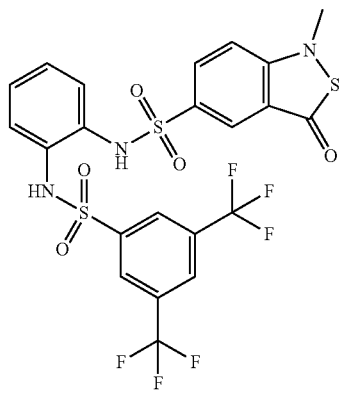 [SMILES: Cn1sc(=O)c2cc(S(=O)(=O)Nc3ccccc3NS(=O)(=O)c3cc(C(F)(F)F)cc(C(F)(F)F)c3)ccc21]

Compound 37 was prepared from benzene-1,2-diamine, 3,5-bis(trifluoromethyl)benzene-1-sulfonyl chloride, and Intermediate 2.

¹H NMR (300 MHz, CDCl₃): δ ppm=8.20 (s, 1H), 8.14 (d, J=2.1 Hz, 1H), 8.07 (s, 1H), 7.68 (dd, J=9.1, 2.1 Hz, 1H), 7.11-7.34 (m, 4H), 6.98-7.11 (m, 1H), 6.73 (dd, J=8.1, 1.3 Hz, 1H), 3.56 ppm (s, 3H).

Example 49

Compound 38

1-methyl-N-{5-methyl-2-[(2-thienylsulfonyl)amino]phenyl}-3-oxo-1,3-dihydro-2,1-benzisothiazole-5-sulfonamide

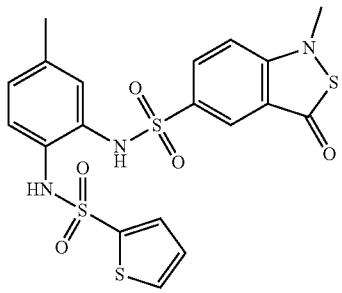 [SMILES: Cc1ccc(NS(=O)(=O)c2cccs2)c(NS(=O)(=O)c2ccc3c(c2)c(=O)sn3C)c1]

Compound 38 was prepared from 1-fluoro-4-methyl-2-nitrobenzene, thiophene-2-sulfonamide, and Intermediate 2.

¹H NMR (300 MHz, DMSO-d₆) δ ppm=9.34 (br. s., 1H), 9.10 (br. s., 1H), 7.97-7.90 (m, 2H), 7.83 (dd, J=2.1, 9.1 Hz, 1H), 7.61 (d, J=9.1 Hz, 1H), 7.44 (d, J=2.3 Hz, 1H), 7.15-7.08 (m, 1H), 6.97 (s, 1H), 6.85 (s, 2H), 3.59 (s, 3H), 2.14 (s, 3H).

Example 50

Compound 39

N-{2-fluoro-6-[(2-thienylsulfonyl)amino]phenyl}-1-methyl-3-oxo-1,3-dihydro-2,1-benzisothiazole-5-sulfonamide

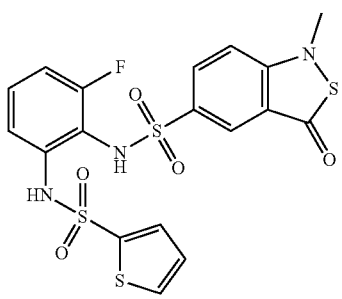 [SMILES: Cn1sc(=O)c2cc(S(=O)(=O)Nc3c(F)cccc3NS(=O)(=O)c3cccs3)ccc21]

Compound 39 was prepared from 1,3-difluoro-2-nitrobenzene, thiophene-2-sulfonamide, and Intermediate 2.

¹H NMR (300 MHz, acetone-d₆) δ ppm=8.68 (br. s., 2H), 7.94 (d, J=2.1 Hz, 1H), 7.88 (dd, J=1.2, 5.0 Hz, 1H), 7.79 (dd, J=1.8, 9.1 Hz, 1H), 7.64 (dd, J=1.2, 3.8 Hz, 1H), 7.54 (d, J=9.1 Hz, 1H), 7.47-7.40 (m, 1H), 7.33 (td, J=6.0, 8.3 Hz, 1H), 7.15 (dd, J=3.8, 5.0 Hz, 1H), 6.90-6.80 (m, 1H), 3.67 (s, 3H).

Example 51

Compound 40

N-{5-cyano-2-[(2-thienylsulfonyl)amino]phenyl}-1-methyl-3-oxo-1,3-dihydro-2,1-benzisothiazole-5-sulfonamide

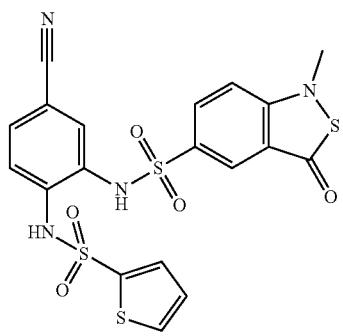 [SMILES: Cn1sc(=O)c2cc(S(=O)(=O)Nc3cc(C#N)ccc3NS(=O)(=O)c3cccs3)ccc21]

Compound 40 was prepared from 4-fluoro-3-nitrobenzonitrile, thiophene-2-sulfonamide, and Intermediate 2.

¹H NMR (300 MHz, acetone-d₆) δ ppm=8.90 (br. s., 2H), 8.03 (d, J=1.8 Hz, 1H), 7.92 (dd, J=1.2, 5.0 Hz, 1H), 7.85 (dd, J=1.9, 8.9 Hz, 1H), 7.68-7.51 (m, 4H), 7.41 (d, J=1.8 Hz, 1H), 7.19-7.13 (m, 1H), 3.67 (s, 3H).

Example 52

Compound 41

N-[5-chloro-2-({[4-chloro-3-(trifluoromethyl)phenyl]sulfonyl}amino)phenyl]-1-methyl-3-oxo-1,3-dihydro-2,1-benzisothiazole-5-sulfonamide

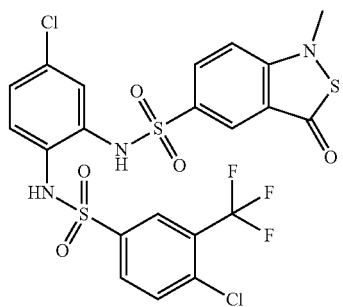 [SMILES: Cn1sc(=O)c2cc(S(=O)(=O)Nc3cc(Cl)ccc3NS(=O)(=O)c3ccc(Cl)c(C(F)(F)F)c3)ccc21]

Compound 41 was prepared from 4-chloro-2-nitroaniline, 4-chloro-3-(trifluoromethyl)benzene-1-sulfonyl chloride, and Intermediate 2.

¹H NMR (300 MHz, acetone-d₆) δ ppm=8.71 (br. s., 2H), 8.06 (dd, J=1.8, 10.3 Hz, 2H), 7.98-7.92 (m, 1H), 7.91-7.83 (m, 2H), 7.58 (d, J=9.1 Hz, 1H), 7.20-7.10 (m, 3H), 3.67 (s, 3H).

Example 53

Compound 42 methyl 3-{[(1-methyl-3-oxo-1,3-dihydro-2,1-benzisothiazol-5-yl)sulfonyl]amino}-4-[(2-thienylsulfonyl)amino]benzoate

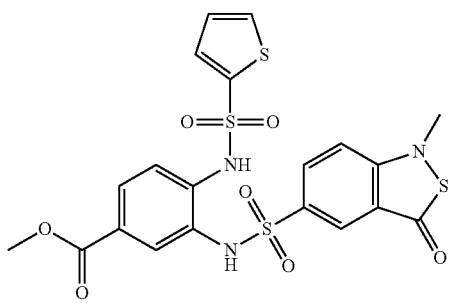 [SMILES: COC(=O)c1ccc(NS(=O)(=O)c2cccs2)c(NS(=O)(=O)c2ccc3c(c2)c(=O)sn3C)c1]

Compound 42 was prepared from methyl 4-fluoro-3-nitrobenzoate, thiophene-2-sulfonamide, and Intermediate 2.

¹H NMR (300 MHz, acetone-d₆) δ ppm 8.73 (br. s., 1H), 8.00 (d, J=1.76 Hz, 1H), 7.90 (dd, J=1.17, 4.98 Hz, 1H), 7.84 (dd, J=2.05, 9.08 Hz, 1H), 7.78 (dd, J=2.05, 8.50 Hz, 1H), 7.59-7.65 (m, 2H), 7.56 (d, J=9.08 Hz, 1H), 7.44 (d, J=8.50 Hz, 1H), 7.12-7.17 (m, 1H), 3.79 (s, 3H), 3.67 (s, 3H).

Example 54

Compound 43

1-methyl-3-oxo-N-[2-({[4-(trifluoromethyl)phenyl]sulfonyl}amino)phenyl]-1,3-dihydro-2,1-benzisothiazole-5-sulfonamide

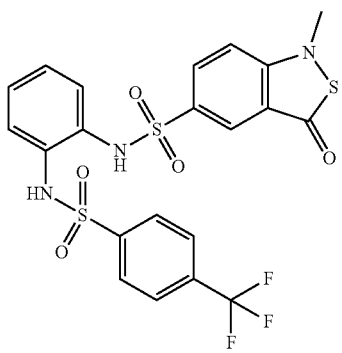 [SMILES: Cn1sc(=O)c2cc(S(=O)(=O)Nc3ccccc3NS(=O)(=O)c3ccc(C(F)(F)F)cc3)ccc21]

Compound 43 was prepared from benzene-1,2-diamine, 4-trifluoromethylbenzene-1-sulfonyl chloride, and Intermediate 2.

¹H NMR (300 MHz, DMSO-d₆): δ ppm=7.17 (d, 1H), 6.96-7.11 (m, 5H), 6.67 (d, J=8.8 Hz, 1H), 6.10-6.34 (m, 4H), 2.78 ppm (s, 3H).

Example 55

Compound 44

N-{2-[(3-furylsulfonyl)amino]phenyl}-1-methyl-3-oxo-1,3-dihydro-2,1-benzisothiazole-5-sulfonamide

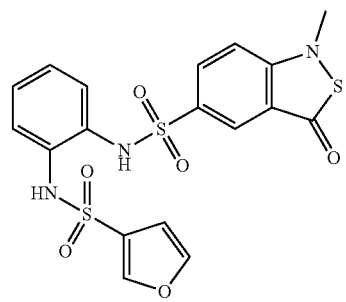 [SMILES: Cn1sc(=O)c2cc(S(=O)(=O)Nc3ccccc3NS(=O)(=O)c3ccoc3)ccc21]

Compound 44 was prepared from benzene-1,2-diamine, furan-3-sulfonyl chloride, and Intermediate 2.

¹H NMR (300 MHz, CD₃OD): δ ppm=7.98 (d, J=1.5 Hz, 1H), 7.84 (dd, J=9.1, 2.1 Hz, 1H), 7.57-7.65 (m, 1H), 7.46 (d, J=9.1 Hz, 1H), 6.95-7.18 (m, 5H), 6.57 (d, J=2.6 Hz, 1H), 3.59 ppm (s, 3H).

Example 56

Compound 45

1-methyl-3-oxo-N-[2-({[3-(trifluoromethyl)phenyl]sulfonyl}amino)phenyl]-1,3-dihydro-2,1-benzisothiazole-5-sulfonamide

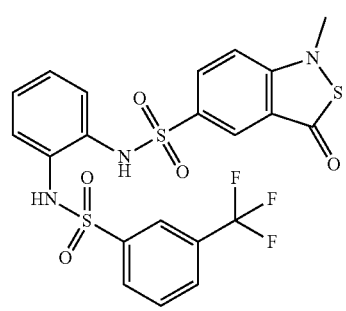 [SMILES: Cn1sc(=O)c2cc(S(=O)(=O)Nc3ccccc3NS(=O)(=O)c3cccc(C(F)(F)F)c3)ccc21]

Compound 45 was prepared from benzene-1,2-diamine, 3-trifluoromethylbenzene-1-sulfonyl chloride, and Intermediate 2.

¹H NMR (300 MHz, CD₃OD): δ ppm=7.84-7.98 (m, 4H), 7.81 (dd, J=9.1, 2.1 Hz, 1H), 7.64-7.76 (m, 1H), 7.45 (d, J=9.1 Hz, 1H), 6.89-7.16 (m, 4H), 3.58 ppm (s, 3H).

Example 57

Compound 46

N-(2-{[(3,5-dichlorophenyl)sulfonyl]amino}phenyl)-1-methyl-3-oxo-1,3-dihydro-2,1-benzisothiazole-5-sulfonamide

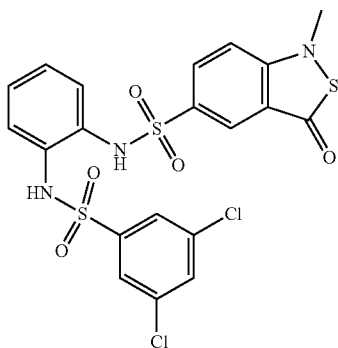 [SMILES: Cn1sc(=O)c2cc(S(=O)(=O)Nc3ccccc3NS(=O)(=O)c3cc(Cl)cc(Cl)c3)ccc21]

Compound 46 was prepared from benzene-1,2-diamine, 3,5-dichlorobenzene-1-sulfonyl chloride, and Intermediate 2.

¹H NMR (300 MHz, CDCl₃): δ ppm=8.94 (br. s., 1H), 8.74 (br. s., 1H), 8.17 (d, J=1.8 Hz, 1H), 7.69 (dd, J=9.1, 2.1 Hz, 1H), 7.53 (d, J=1.8 Hz, 2H), 7.42 (d, J=1.8 Hz, 1H), 7.09 (d, J=9.1 Hz, 1H), 6.91-7.07 (m, 4H), 3.46 ppm (s, 3H).

Example 58

Compound 47

N-(2-{[(3,5-difluorophenyl)sulfonyl]amino}phenyl)-1-methyl-3-oxo-1,3-dihydro-2,1-benzisothiazole-5-sulfonamide

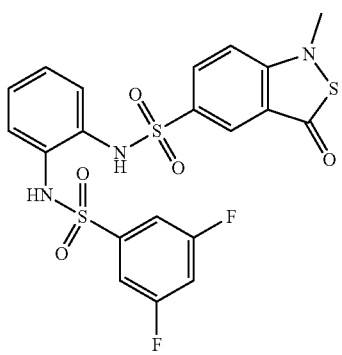 [SMILES: Cn1sc(=O)c2cc(S(=O)(=O)Nc3ccccc3NS(=O)(=O)c3cc(F)cc(F)c3)ccc21]

Compound 47 was prepared from benzene-1,2-diamine, 3,5-difluorobenzene-1-sulfonyl chloride, and Intermediate 2.

¹H NMR (300 MHz, DMSO-d₆): δ ppm=9.58 (br. s., 1H), 9.34 (br. s., 1H), 7.94 (d, J=1.8 Hz, 1H), 7.85 (dd, J=9.1, 2.1 Hz, 1H), 7.63 (d, J=9.1 Hz, 2H), 7.35-7.44 (m, 2H), 6.92-7.13 (m, 4H), 3.59 ppm (s, 3H).

Example 59

Compound 48

N-(2-{[(3-fluorophenyl)sulfonyl]amino}phenyl)-1-methyl-3-oxo-1,3-dihydro-2,1-benzisothiazole-5-sulfonamide

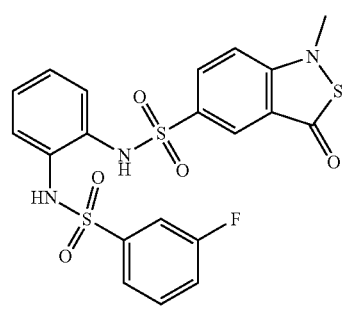 [SMILES: Cn1sc(=O)c2cc(S(=O)(=O)Nc3ccccc3NS(=O)(=O)c3cccc(F)c3)ccc21]

Compound 48 was prepared from benzene-1,2-diamine, 3-fluorobenzene-1-sulfonyl chloride, and Intermediate 2.

¹H NMR (300 MHz, DMSO-d₆): δ ppm=9.46 (br. s., 1H), 9.30 (br. s., 1H), 7.93 (d, J=2.1 Hz, 1H), 7.83 (dd, J=9.1, 2.1 Hz, 1H), 7.43-7.68 (m, 5H), 6.89-7.12 (m, 4H), 3.59 ppm (s, 3H).

Example 60

Compound 49

N-(2-{[(4-methoxyphenyl)sulfonyl]amino}phenyl)-1-methyl-3-oxo-1,3-dihydro-2,1-benzisothiazole-5-sulfonamide

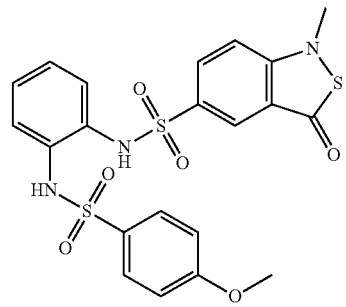 [SMILES: COc1ccc(S(=O)(=O)Nc2ccccc2NS(=O)(=O)c2ccc3c(c2)c(=O)sn3C)cc1]

Compound 49 was prepared from benzene-1,2-diamine, 4-methoxybenzene-1-sulfonyl chloride, and Intermediate 2.

¹H NMR (300 MHz, CD₃OD): δ ppm=7.96 (d, 1H), 7.84 (dd, J=9.1, 2.1 Hz, 1H), 7.57 (d, J=9.1 Hz, 2H), 7.45 (d, J=9.1 Hz, 1H), 6.82-7.09 (m, 6H), 3.83 (s, 3H), 3.58 ppm (s, 3H).

Example 61

Compound 50

N-(5-chloro-2-{[(3-chlorophenyl)sulfonyl]amino}phenyl)-1-methyl-3-oxo-1,3-dihydro-2,1-benzisothiazole-5-sulfonamide

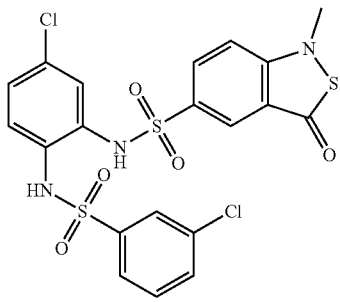 [SMILES: Cn1sc(=O)c2cc(S(=O)(=O)Nc3cc(Cl)ccc3NS(=O)(=O)c3cccc(Cl)c3)ccc21]

Compound 50 was prepared from 4-chloro-2-nitroaniline, 3-chlorobenzene-1-sulfonyl chloride, and Intermediate 2.

¹H NMR (300 MHz, CD₃OD): δ ppm=8.02 (d, 1H), 7.87 (dd, J=9.1, 2.1 Hz, 1H), 7.44-7.67 (m, 6H), 7.12 (d, J=2.6 Hz, 1H), 7.06 (dd, J=8.8, 2.4 Hz, 1H), 6.83 (d, J=8.5 Hz, 1H), 3.59 ppm (s, 3H).

Example 62

Compound 51

N-(5-chloro-2-{[(3,4-dichlorophenyl)sulfonyl]amino}phenyl)-1-methyl-3-oxo-1,3-dihydro-2,1-benzisothiazole-5-sulfonamide

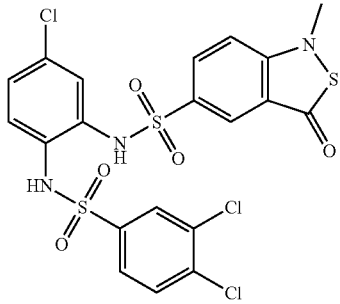 [SMILES: Cn1sc(=O)c2cc(S(=O)(=O)Nc3cc(Cl)ccc3NS(=O)(=O)c3ccc(Cl)c(Cl)c3)ccc21]

Compound 51 was prepared from 4-chloro-2-nitroaniline, 3,4-dichlorobenzene-1-sulfonyl chloride, and Intermediate 2.

¹H NMR (300 MHz, CD₃OD): δ ppm=8.02 (d, J=1.8 Hz, 1H), 7.85 (dd, J=9.1, 2.1 Hz, 1H), 7.77 (d, J=2.1 Hz, 1H), 7.69 (d, J=8.5 Hz, 1H), 7.45-7.58 (m, 2H), 7.00-7.14 (m, 2H), 6.94 (d, J=8.5 Hz, 1H), 3.59 ppm (s, 3H).

Example 63

Compound 52

N-{4-methoxy-2-[(2-thienylsulfonyl)amino]phenyl}-1-methyl-3-oxo-1,3-dihydro-2,1-benzisothiazole-5-sulfonamide

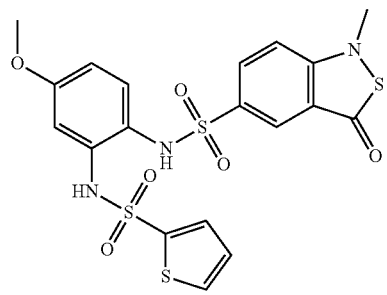 [SMILES: COc1ccc(NS(=O)(=O)c2ccc3c(c2)c(=O)sn3C)c(NS(=O)(=O)c2cccs2)c1]

Compound 52 was prepared from 2-fluoro-4-methoxy-1-nitrobenzene, thiophene-2-sulfonamide, and Intermediate 2.

¹H NMR (300 MHz, DMSO-d₆) δ ppm 9.30 (br. s, 1H), 9.15 (br. s., 1H), 7.95 (d, J=4.40 Hz, 1H), 7.84 (s, 1H), 7.69-7.78 (m, 1H), 7.50-7.66 (m, 2H), 7.14 (t, J=4.25 Hz, 1H), 6.85 (d, J=8.50 Hz, 1H), 6.55-6.71 (m, 2H), 3.62 (s, 3H), 3.60 (s, 3H).

Example 64

Compound 53

N-{4,5-dimethyl-2-[(2-thienylsulfonyl)amino]phenyl}-1-methyl-3-oxo-1,3-dihydro-2,1-benzisothiazole-5-sulfonamide

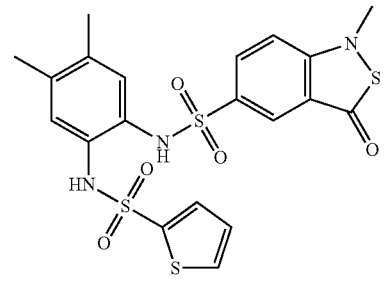 [SMILES: Cc1cc(NS(=O)(=O)c2ccc3c(c2)c(=O)sn3C)c(NS(=O)(=O)c2cccs2)cc1C]

Compound 53 was prepared from 4,5-dimethylbenzene-1,2-diamine, thiophene-2-sulfonyl chloride, and Intermediate 2.

¹H NMR (300 MHz, DMSO-d₆) δ ppm 9.24 (br. s., 1H), 9.02 (br. s., 1H), 7.89-7.96 (m, 2H), 7.80 (dd, J=2.05, 9.08 Hz, 1H), 7.61 (d, J=9.08 Hz, 1H), 7.44-7.48 (m, 1H), 7.09-7.15 (m, 1H), 6.87 (s, 1H), 6.78 (s, 1H), 3.59 (s, 3H), 1.97-2.11 (m, 6H).

Example 65

Compound 54

N-{4-cyano-2-[(2-thienylsulfonyl)amino]phenyl}-1-methyl-3-oxo-1,3-dihydro-2,1-benzisothiazole-5-sulfonamide

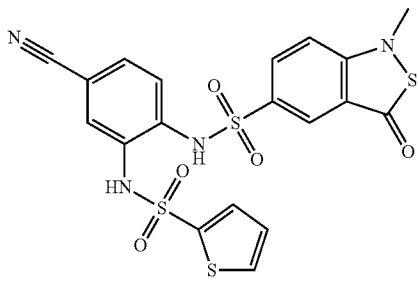 [SMILES: Cn1sc(=O)c2cc(S(=O)(=O)Nc3ccc(C#N)cc3NS(=O)(=O)c3cccs3)ccc21]

Compound 54 was prepared from 3-fluoro-4-nitrobenzonitrile, thiophene-2-sulfonamide, and Intermediate 2.

$^1$H NMR (300 MHz, acetone-$d_6$) δ ppm 8.60-8.66 (m, 1H), 8.36 (s, 1H), 7.99 (d, J=2.64 Hz, 1H), 7.55 (d, J=4.10 Hz, 1H), 7.35 (d, J=1.47 Hz, 1H), 7.27 (d, J=9.08 Hz, 1H), 7.08 (d, J=8.20 Hz, 1H), 6.90-6.96 (m, 1H), 6.77 (dd, J=1.76, 8.20 Hz, 1H), 3.57 (s, 3H).

Example 66

Compound 55 methyl 4-{[(1-methyl-3-oxo-1,3-dihydro-2,1-benzisothiazol-5-yl)sulfonyl]amino}-3-[(2-thienylsulfonyl)amino]benzoate

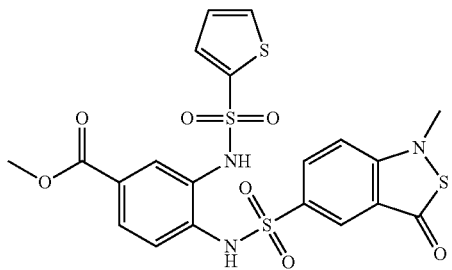 [SMILES: COC(=O)c1ccc(NS(=O)(=O)c2ccc3c(c2)c(=O)sn3C)c(NS(=O)(=O)c2cccs2)c1]

Compound 55 was prepared from methyl 3-fluoro-4-nitrobenzoate, thiophene-2-sulfonamide, and Intermediate 2.

$^1$H NMR (300 MHz, acetone-$d_6$) δ ppm 8.85 (br. s., 2H), 7.98 (d, J=1.76 Hz, 1H), 7.91 (dd, J=1.17, 4.98 Hz, 1H), 7.83 (dd, J=2.05, 9.08 Hz, 1H), 7.70-7.77 (m, 1H), 7.67 (dd, J=1.47, 3.81 Hz, 1H), 7.59-7.65 (m, 1H), 7.57 (d, J=9.08 Hz, 1H), 7.45 (d, J=2.05 Hz, 1H), 7.16 (dd, J=3.81, 4.98 Hz, 1H), 3.66 (s, 3H), 2.94 (s, 3H).

Example 67

Compound 56

N-(5-chloro-2-{[(3,5-dichlorophenyl)sulfonyl]amino}phenyl)-1-methyl-3-oxo-1,3-dihydro-2,1-benzisothiazole-5-sulfonamide

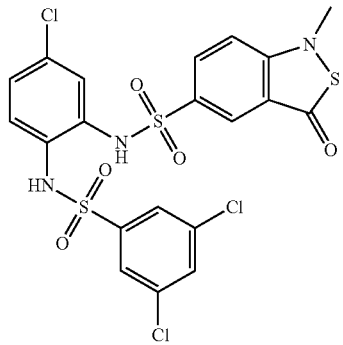 [SMILES: Cn1sc(=O)c2cc(S(=O)(=O)Nc3cc(Cl)ccc3NS(=O)(=O)c3cc(Cl)cc(Cl)c3)ccc21]

Compound 56 was prepared from 4-chloro-2-nitroaniline, 3,5-dichlorobenzene-1-sulfonyl chloride, and Intermediate 2.

$^1$H NMR (300 MHz, CD$_3$OD): δ ppm=8.03 (d, J=2.1 Hz, 1H), 7.86 (dd, J=9.2, 1.9 Hz, 1H), 7.72 (t, J=1.8 Hz, 1H), 7.56 (d, J=2.1 Hz, 2H), 7.50 (d, J=9.1 Hz, 1H), 7.05-7.14 (m, 2H), 6.93 (d, J=8.5 Hz, 1H), 3.60 ppm (s, 3H).

Example 68

Compound 57

N-(5-chloro-2-{[(3-methoxyphenyl)sulfonyl]amino}phenyl)-1-methyl-3-oxo-1,3-dihydro-2,1-benzisothiazole-5-sulfonamide

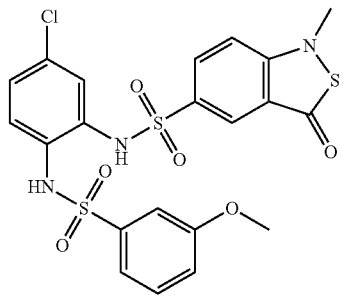 [SMILES: COc1cccc(S(=O)(=O)Nc2ccc(Cl)cc2NS(=O)(=O)c2ccc3c(c2)c(=O)sn3C)c1]

Compound 57 was prepared from 4-chloro-2-nitroaniline, 3-methoxybenzene-1-sulfonyl chloride, and Intermediate 2.

¹H NMR (300 MHz, DMSO-d₆): δ ppm=9.49 (br. s., 1H), 8.00 (d, 1H), 7.84 (dd, 1H), 7.64 (d, 1H), 7.37-7.52 (m, 1H), 7.14-7.29 (m, 3H), 7.02-7.17 (m, 2H), 6.92 (d, 1H), 3.78 (s, 3H), 3.61 ppm (s, 3H).

Example 69

Compound 58

N-(5-chloro-2-{[(5-methyl-2-thienyl)sulfonyl]amino}phenyl)-1-methyl-3-oxo-1,3-dihydro-2,1-benzisothiazole-5-sulfonamide

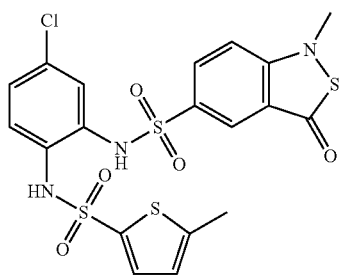 [SMILES: Cc1ccc(S(=O)(=O)Nc2ccc(Cl)cc2NS(=O)(=O)c2ccc3c(c2)c(=O)sn3C)s1]

Compound 58 was prepared from 4-chloro-2-nitroaniline, 5-methylthiophene-2-sulfonyl chloride, and Intermediate 2.

¹H NMR (300 MHz, CD₃OD): δ ppm=8.02 (dd, J=2.1, 0.6 Hz, 1H), 7.88 (dd, J=9.1, 1.8 Hz, 1H), 7.49 (d, J=8.5 Hz, 1H), 7.19 (dd, J=7.5, 3.1 Hz, 2H), 7.04 (dd, J=8.5, 2.3 Hz, 1H), 6.91 (d, J=8.5 Hz, 1H), 6.77 (dd, J=3.8, 1.2 Hz, 1H), 3.59 (s, 3H), 2.48 ppm (d, J=1.2 Hz, 3H).

Example 70

Compound 59

N-(5-chloro-2-{[(4-methoxyphenyl)sulfonyl]amino}phenyl)-1-methyl-3-oxo-1,3-dihydro-2,1-benzisothiazole-5-sulfonamide

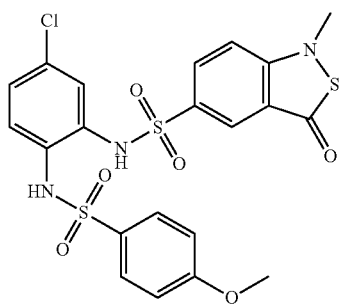 [SMILES: COc1ccc(S(=O)(=O)Nc2ccc(Cl)cc2NS(=O)(=O)c2ccc3c(c2)c(=O)sn3C)cc1]

Compound 59 was prepared from 4-chloro-2-nitroaniline, 4-methoxybenzene-1-sulfonyl chloride, and Intermediate 2.

¹H NMR (300 MHz, CD₃OD): δ ppm=8.01 (d, J=1.5 Hz, 1H), 7.87 (dd, J=9.1, 2.1 Hz, 1H), 7.52-7.64 (m, 2H), 7.48 (d, J=9.1 Hz, 1H), 7.14 (d, J=2.6 Hz, 1H), 6.91-7.05 (m, 3H), 6.77 (d, J=8.8 Hz, 1H), 3.83 (s, 3H), 3.59 ppm (s, 3H).

Example 71

Compound 60

N-(5-chloro-2-{[(3,4-dimethoxyphenyl)sulfonyl]amino}phenyl)-1-methyl-3-oxo-1,3-dihydro-2,1-benzisothiazole-5-sulfonamide

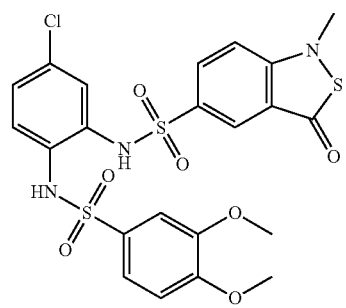 [SMILES: COc1ccc(S(=O)(=O)Nc2ccc(Cl)cc2NS(=O)(=O)c2ccc3c(c2)c(=O)sn3C)cc1OC]

Compound 60 was prepared from 4-chloro-2-nitroaniline, 3,4-dimethoxybenzene-1-sulfonyl chloride, and Intermediate 2.

¹H NMR (300 MHz, CD₃OD): δ ppm=8.01 (d, J=1.8 Hz, 1H), 7.85 (dd, J=9.2, 1.9 Hz, 1H), 7.48 (d, J=9.1 Hz, 1H), 7.21 (dd, J=8.4, 2.2 Hz, 1H), 7.15 (d, J=2.1 Hz, 1H), 7.00-7.11 (m, 2H), 6.97 (d, J=8.5 Hz, 1H), 6.86 (d, J=8.8 Hz, 1H), 3.86 (s, 3H), 3.77 (s, 3H), 3.59 ppm (s, 3H).

Example 72

Compound 61

N-{5-isopropyl-2-[(2-thienylsulfonyl)amino]phenyl}-1-methyl-3-oxo-1,3-dihydro-2,1-benzisothiazole-5-sulfonamide

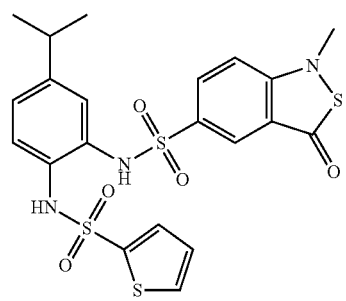 [SMILES: CC(C)c1ccc(NS(=O)(=O)c2cccs2)c(NS(=O)(=O)c2ccc3c(c2)c(=O)sn3C)c1]

Compound 61 was prepared from 4-isopropyl-2-nitroaniline (CAS 63649-64-9), thiophene-2-sulfonyl chloride, and Intermediate 2.

¹H NMR (300 MHz, acetone-d₆) δ ppm 8.41 (br. s., 2H), 7.95 (d, J=1.76 Hz, 1H), 7.82-7.88 (m, 2H), 7.55 (d, J=9.08 Hz, 1H), 7.46 (dd, J=1.17, 3.81 Hz, 1H), 7.12 (dd, 1H), 7.05

(d, J=8.21 Hz, 1H), 6.97-7.02 (m, 1H), 6.94 (d, J=1.76 Hz, 1H), 3.64 (s, 3H), 2.66-2.79 (m, 1H), 1.03 (d, J=7.03 Hz, 6H).

Example 73

Compound 62

N-{4-isopropyl-2-[(2-thienylsulfonyl)amino]phenyl}-1-methyl-3-oxo-1,3-dihydro-2,1-benzisothiazole-5-sulfonamide

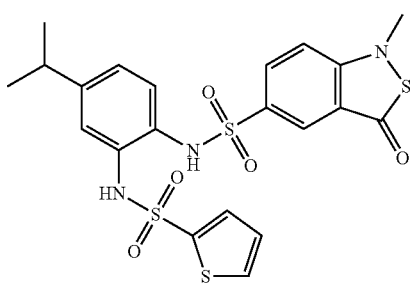 [SMILES: CC(C)c1ccc(NS(=O)(=O)c2ccc3c(c2)c(=O)sn3C)c(NS(=O)(=O)c2cccs2)c1]

Compound 62 was prepared from 5-isopropyl-2-nitroaniline (CAS 261712-00-9), thiophene-2-sulfonyl chloride, and Intermediate 2.

$^1$H NMR (300 MHz, acetone-$d_6$) δ ppm 8.41 (br. s., 1H), 7.83-7.99 (m, 3H), 7.54 (d, J=9.08 Hz, 1H), 7.45 (d, J=3.81 Hz, 1H), 6.89-7.17 (m, 4H), 3.65 (s, 3H), 2.62-2.75 (m, 1H), 1.07 (d, J=7.03 Hz, 6H).

Example 74

Compound 63

N-(5-chloro-2-{[(4-methylphenyl)sulfonyl]amino}phenyl)-1-methyl-3-oxo-1,3-dihydro-2,1-benzisothiazole-5-sulfonamide

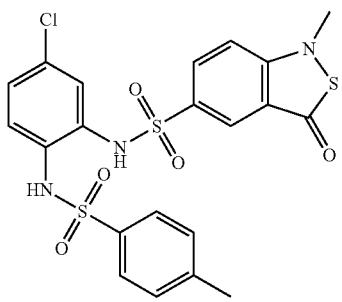 [SMILES: Cc1ccc(S(=O)(=O)Nc2ccc(Cl)cc2NS(=O)(=O)c2ccc3c(c2)c(=O)sn3C)cc1]

Compound 63 was prepared from 4-chloro-2-nitroaniline, p-tolyl-1-sulfonyl chloride, and Intermediate 2.

$^1$H NMR (300 MHz, CD$_3$OD): δ ppm=8.01 (d, J=1.5 Hz, 1H), 7.87 (dd, J=9.1, 2.1 Hz, 1H), 7.43-7.56 (m, 3H), 7.29 (d, J=8.2 Hz, 2H), 7.14 (d, J=2.3 Hz, 1H), 6.98 (dd, J=8.6, 2.5 Hz, 1H), 6.74 (d, J=8.8 Hz, 1H), 3.58 (s, 3H), 2.38 ppm (s, 3H).

Example 75

Compound 64

N-(5-chloro-2-{[(4-hydroxyphenyl)sulfonyl]amino}phenyl)-1-methyl-3-oxo-1,3-dihydro-2,1-benzisothiazole-5-sulfonamide

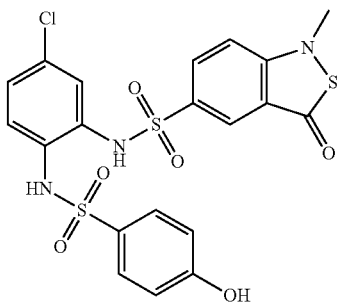 [SMILES: Cn1sc(=O)c2cc(S(=O)(=O)Nc3cc(Cl)ccc3NS(=O)(=O)c3ccc(O)cc3)ccc21]

To a solution of Compound 59 (1 equiv.) in CH$_2$Cl$_2$ was added BBr$_3$ (2 equiv.) at room temperature and the mixture was stirred overnight. The reaction was quenched with water and extracted with CH$_2$Cl$_2$ (×2). The combined organic layer was washed with brine, dried over Na$_2$SO$_4$, and concentrated. The crude product was purified by flash column chromatography on silica gel to yield Compound 64 as a brown solid.

$^1$H NMR (300 MHz, acetone-$d_6$): δ ppm=7.92 (dd, 1H), 7.53 (d, J=8.8 Hz, 5H), 7.26 (s, 2H), 6.94 (s, 2H), 6.91 (d, J=8.8 Hz, 4H), 4.05 (d, J=7.3 Hz, 3H), 3.67 (s, 6H), 2.83 (s, 9H), 2.03-2.08 (m, 9H), 1.96 (s, 4H), 1.20 ppm (t, J=7.2 Hz, 4H).

Example 76

Compound 65

N-{5-chloro-4-methyl-2-[(2-thienylsulfonyl)amino]phenyl}-1-methyl-3-oxo-1,3-dihydro-2,1-benzisothiazole-5-sulfonamide

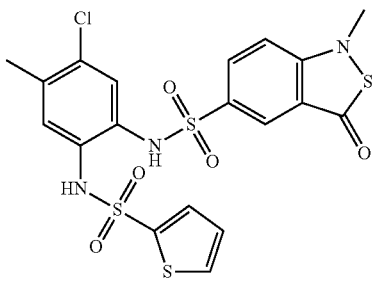

Compound 65 was prepared from 5-chloro-4-methyl-2-nitroaniline, Intermediate 2, and thiophene-2-sulfonyl chloride.

$^1$H NMR (300 MHz, acetone-$d_6$) δ ppm 8.55 (br. s., 2H), 8.02 (d, J=2.05 Hz, 1H), 7.84-7.92 (m, 2H), 7.57 (d, J=9.08

Hz, 1H), 7.50 (dd, J=1.17, 3.81 Hz, 1H), 7.11-7.18 (m, 2H), 7.06 (s, 1H), 3.67 (s, 3H), 2.20 (s, 3H).

$^1$H NMR (300 MHz, DMSO-d$_6$) δ ppm 9.61 (s, 1H), 7.91 (s, 1H), 7.73 (d, J=2.05 Hz, 1H), 7.64 (d, J=11.14 Hz, 1H), 7.15-7.40 (m, 5H), 6.55 (d, J=8.79 Hz, 2H), 3.38 (s, 3H), 2.52 (s, 6H).

Example 77

Compound 66

N-{4-chloro-5-methyl-2-[(2-thienylsulfonyl)amino]phenyl}-1-methyl-3-oxo-1,3-dihydro-2,1-benzisothiazole-5-sulfonamide

Example 79

Compound 68

N-{4-(dimethylamino)-2-[(2-thienylsulfonyl)amino]phenyl}-1-methyl-3-oxo-1,3-dihydro-2,1-benzisothiazole-5-sulfonamide

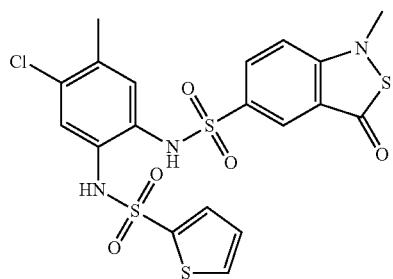 [SMILES: Cc1cc(NS(=O)(=O)c2ccc3c(c2)c(=O)sn3C)c(NS(=O)(=O)c2cccs2)cc1Cl]

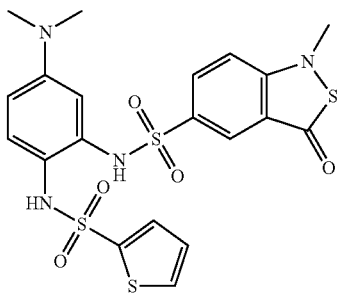

Compound 66 was prepared from 5-chloro-4-methyl-2-nitroaniline, thiophene-2-sulfonyl chloride, and Intermediate 2.

$^1$H NMR (300 MHz, acetone-d$_6$) δ ppm 8.59 (br. s., 2H), 8.02 (d, J=2.05 Hz, 1H), 7.82-7.92 (m, 2H), 7.49-7.57 (m, 2H), 7.12-7.18 (m, 2H), 7.08 (s, 1H), 3.65 (s, 3H), 2.20 (s, 3H).

Compound 68 was prepared from N1,N1-dimethyl-3-nitrobenzene-1,4-diamine, thiophene-2-sulfonyl chloride, and Intermediate 2.

$^1$H NMR (300 MHz, acetone-d$_6$) δ ppm 8.32 (s, 1H), 8.12 (s, 1H), 7.94 (d, J=1.76 Hz, 1H), 7.85 (dd, J=1.32, 5.13 Hz, 1H), 7.79 (dd, J=1.76, 9.08 Hz, 1H), 7.47-7.58 (m, 2H), 7.13 (dd, J=3.81, 4.98 Hz, 1H), 6.68 (d, J=9.08 Hz, 1H), 6.61 (d, J=2.93 Hz, 1H), 6.35 (dd, J=2.93, 8.79 Hz, 1H), 3.65 (s, 3H), 2.83 (s, 6H).

Example 78

Compound 67

N-[5-chloro-2-({[4-(dimethylamino)phenyl]sulfonyl}amino)phenyl]-1-methyl-3-oxo-1,3-dihydro-2,1-benzisothiazole-5-sulfonamide

Example 80

Compound 69

N-{4-(dimethylamino)-2-[(2-thienylsulfonyl)amino]phenyl}-1-methyl-3-oxo-1,3-dihydro-2,1-benzisothiazole-5-sulfonamide

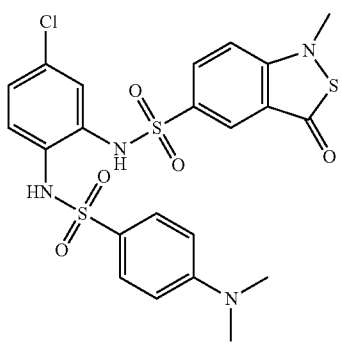 [SMILES: CN(C)c1ccc(S(=O)(=O)Nc2ccc(Cl)cc2NS(=O)(=O)c2ccc3c(c2)c(=O)sn3C)cc1]

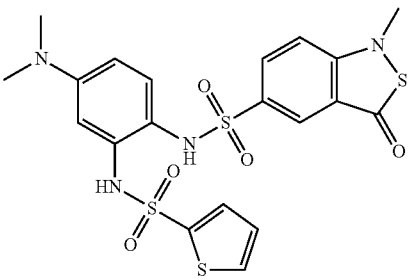 [SMILES: CN(C)c1ccc(NS(=O)(=O)c2ccc3c(c2)c(=O)sn3C)c(NS(=O)(=O)c2cccs2)c1]

Compound 67 was prepared from Intermediate 7 and Intermediate 2.

Compound 69 was prepared from N1,N1-dimethyl-4-nitrobenzene-1,3-diamine, thiophene-2-sulfonyl chloride, and Intermediate 2.

$^1$H NMR (300 MHz, acetone-d$_6$) δ ppm 8.22 (br. s., 2H), 8.10 (d, J=1.76 Hz, 1H), 7.96 (dd, J=1.76, 9.08 Hz, 1H), 7.85 (dd, J=1.47, 4.98 Hz, 1H), 7.55 (d, J=9.08 Hz, 1H), 7.37 (dd, J=1.32, 3.66 Hz, 1H), 7.11 (dd, J=3.81, 4.98 Hz, 1H), 6.60-6.65 (m, 2H), 6.33 (dd, J=2.93, 9.08 Hz, 1H), 3.65 (s, 3H), 2.84 (s, 6H).

Example 81

Compound 70

N-(5-chloro-2-{[(4-isopropylphenyl)sulfonyl]amino}phenyl)-1-methyl-3-oxo-1,3-dihydro-2,1-benzisothiazole-5-sulfonamide

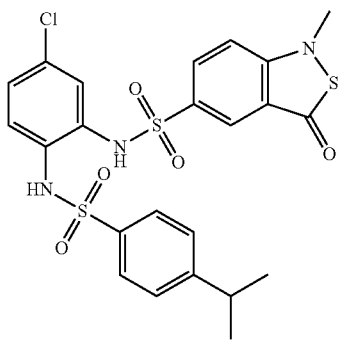 [SMILES: CC(C)c1ccc(S(=O)(=O)Nc2ccc(Cl)cc2NS(=O)(=O)c2ccc3c(c2)c(=O)sn3C)cc1]

Compound 70 was prepared from 4-chloro-2-nitroaniline, 4-isopropylbenzene-1-sulfonyl chloride, and Intermediate 2.

$^1$H NMR (300 MHz, CD$_3$OD) δ ppm 8.02 (d, J=1.76 Hz, 1H), 7.88 (dd, J=1.76, 9.08 Hz, 1H), 7.52-7.63 (m, 2H), 7.49 (d, J=9.08 Hz, 1H), 7.30-7.41 (m, 2H), 7.16 (d, J=2.64 Hz, 1H), 6.98 (dd, J=2.34, 8.50 Hz, 1H), 6.73 (d, J=8.50 Hz, 1H), 3.59 (s, 3H), 2.83-3.11 (m, 1H), 1.24 (d, J=6.74 Hz, 6H).

Example 82

Compound 71

N-[5-chloro-2-({[3-(dimethylamino)phenyl]sulfonyl}amino)phenyl]-1-methyl-3-oxo-1,3-dihydro-2,1-benzisothiazole-5-sulfonamide

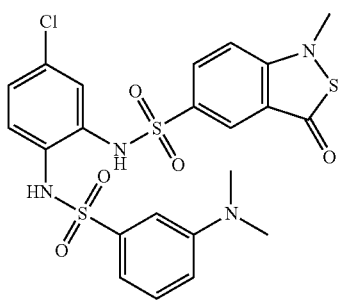 [SMILES: CN(C)c1cccc(S(=O)(=O)Nc2ccc(Cl)cc2NS(=O)(=O)c2ccc3c(c2)c(=O)sn3C)c1]

Compound 71 was prepared from Intermediate 8 and Intermediate 2.

$^1$H NMR (300 MHz, DMSO-d$_6$) δ ppm 7.79 (d, J=1.76 Hz, 1H), 7.63 (dd, J=2.05, 9.08 Hz, 1H), 7.36 (d, J=2.64 Hz, 1H), 7.13-7.30 (m, 4H), 6.99 (d, J=6.74 Hz, 1H), 6.63-6.76 (m, 2H), 3.42 (s, 3H), 2.58 (s, 6H).

Example 83

Compound 72

N-{5-chloro-2-[(2-thienylsulfonyl)amino]phenyl}-1-methyl-3-oxo-1,3-dihydro-2,1-benzisothiazole-5-carboxamide

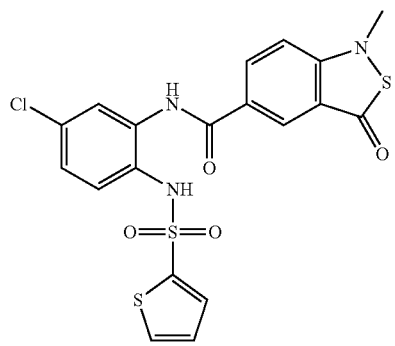 [SMILES: Cn1sc(=O)c2cc(C(=O)Nc3cc(Cl)ccc3NS(=O)(=O)c3cccs3)ccc21]

To a solution of Intermediate 10 (69 mg, 0.33 mmol) and Et$_3$N (230 μl, 1.65 mmol) in THF (5 ml) at room temperature was added ClCO$_2$Et (31 μl, 0.33 mmol). The mixture was stirred for 1 h and Intermediate 11 (143 mg, 0.50 mmol) was added. The reaction was stirred for 22 h, quenched with H$_2$O, extracted with EtOAc (×2). The combined organic layer was washed with brine, dried over Na$_2$SO$_4$, and concentrated. The crude product was purified by chromatography on silica gel to yield Compound 72.

$^1$H NMR (300 MHz, acetone-d$_6$) δ ppm 9.53 (br. s., 1H), 8.85 (s, 1H), 8.14-8.25 (m, 2H), 7.94 (d, J=1.47 Hz, 1H), 7.81 (dd, J=1.17, 4.98 Hz, 1H), 7.59 (d, J=8.79 Hz, 1H), 7.40 (dd, J=1.17, 3.52 Hz, 1H), 7.21-7.30 (m, 2H), 7.09 (dd, J=3.81, 4.98 Hz, 1H), 3.68 (s, 3H).

Example 84

Compound 73

N-(5-chloro-2-{[(2-methoxyphenyl)sulfonyl]amino}phenyl)-1-methyl-3-oxo-1,3-dihydro-2,1-benzisothiazole-5-sulfonamide

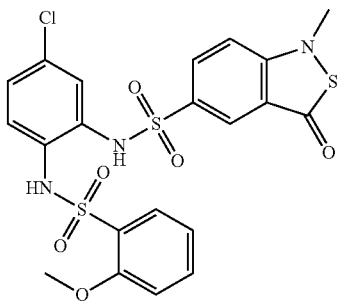 [SMILES: COc1ccccc1S(=O)(=O)Nc1ccc(Cl)cc1NS(=O)(=O)c1ccc2c(c1)c(=O)sn2C]

Compound 73 was prepared from 4-chloro-2-nitroaniline, 2-methoxybenzene-1-sulfonyl chloride, and Intermediate 2.

¹H NMR (300 MHz, CD₃OD) δ ppm 8.01 (d, J=1.47 Hz, 1H), 7.80 (dd, J=2.05, 9.08 Hz, 1H), 7.52-7.63 (m, 2H), 7.47 (d, J=8.79 Hz, 1H), 7.21 (d, J=8.20 Hz, 1H), 7.17 (d, J=8.50 Hz, 1H), 7.04 (dd, J=2.49, 8.64 Hz, 1H), 6.95 (t, J=7.62 Hz, 1H), 6.80 (d, J=2.34 Hz, 1H), 4.05 (s, 3H), 3.59 (s, 3H).

Example 85

Compound 74

N-(4-{[(4-chloro-2-{[(1-methyl-3-oxo-1,3-dihydro-2,1-benzisothiazol-5-yl)sulfonyl]amino}phenyl)amino]sulfonyl}phenyl)acetamide

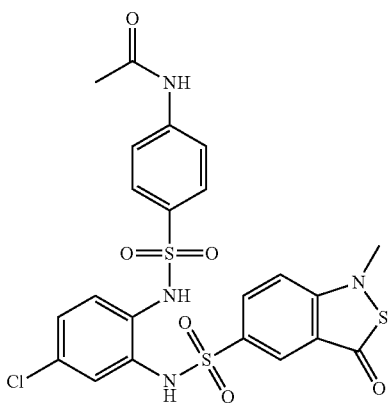 [SMILES: CC(=O)Nc1ccc(S(=O)(=O)Nc2ccc(Cl)cc2NS(=O)(=O)c2ccc3c(c2)c(=O)sn3C)cc1]

Compound 74 was prepared from 4-chloro-2-nitroaniline, 4-acetamidobenzene-1-sulfonyl chloride, and Intermediate 2.

¹H NMR (300 MHz, CD₃OD) δ ppm 8.02 (d, J=1.47 Hz, 1H), 7.85 (dd, J=2.05, 9.08 Hz, 1H), 7.63-7.70 (m, 2H), 7.52-7.59 (m, 2H), 7.48 (d, J=8.79 Hz, 1H), 7.14 (d, J=2.64 Hz, 1H), 7.00 (dd, J=2.49, 8.64 Hz, 1H), 6.78 (d, J=8.79 Hz, 1H), 3.59 (s, 3H), 2.13 (s, 3H).

Example 86

Compound 75

N-(4-chloro-2-{[(1-methyl-3-oxo-1,3-dihydro-2,1-benzisothiazol-5-yl)sulfonyl]amino}phenyl)-4-methoxybenzamide

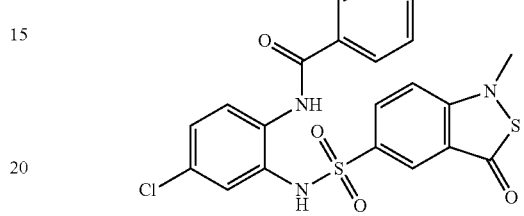

Compound 75 was prepared from 4-chloro-2-nitroaniline, 4-methoxybenzoyl chloride, and Intermediate 2.

¹H NMR (300 MHz, CDCl₃) δ ppm 8.05 (d, J=2.05 Hz, 1H), 7.78 (d, J=8.79 Hz, 1H), 7.64-7.72 (m, 2H), 7.55 (dd, J=2.05, 9.08 Hz, 1H), 7.12 (dd, J=2.34, 8.79 Hz, 1H), 7.02 (d, J=9.08 Hz, 1H), 6.75-6.89 (m, 3H), 3.76 (s, 3H), 3.41 (s, 3H).

Biological Data

HEK-Gqi5 cells stably expressing CCR2 were cultured in (DMEM high glucose, 10% FBS, 1% PSA, 400 μg/ml geneticin and 50 μg/ml hygromycin. Appropriate positive control chemokines (MCP-1, MIP1A or RANTES) was used as the positive control agonist for screening compound-induced calcium activity assayed on the FLIPR$^{Tetra}$. The drug plates were prepared in 384-well microplates using the EP3 and the MultiPROBE robotic liquid handling systems. Compounds were synthesized and tested for CCR2 activity.

TABLE 1 shows activity for CCR2 receptor (IC₅₀) nM

| Name | CCR2 IC50 (nM) | CCR2 % ANTAG |
|---|---|---|
| N-{5-chloro-2-[(4-oxopiperidin-1-yl)carbonyl]pyridin-3-yl}-1-methyl-3-oxo-1,3-dihydro-2,1-benzisothiazole-5-sulfonamide | nd | 58 |
| N,N-dimethyl-N-(4-{[(1-methyl-3-oxo-1,3-dihydro-2,1-benzisothiazol-5-yl)carbonyl]amino}benzyl)tetrahydro-2H-pyran-4-aminium | 1186 | 85 |
| N-(2,3-dimethoxyphenyl)-1-methyl-3-oxo-1,3-dihydro-2,1-benzisothiazole-5-sulfonamide | 3831 | 55 |
| N-(2,3-dihydro-1,4-benzodioxin-5-yl)-1-methyl-3-oxo-1,3-dihydro-2,1-benzisothiazole-5-sulfonamide | 1453 | 76 |
| 1-isopropyl-3-oxo-N-{2-[(2-thienylsulfonyl)amino]phenyl}-1,3-dihydro-2,1-benzisothiazole-5-sulfonamide | 4324 | 90 |
| N-(2,2-difluoro-1,3-benzodioxol-4-yl)-1-methyl-3-oxo-1,3-dihydro-2,1-benzisothiazole-5-sulfonamide | 1001 | 80 |
| 1-methyl-3-oxo-N-{2-[(2-thienylsulfonyl)amino]pyridin-3-yl}-1,3-dihydro-2,1-benzisothiazole-5-sulfonamide | 1914 | 83 |
| N-{5-chloro-2-[(2-thienylsulfonyl)amino]phenyl}-1-methyl-3-oxo-1,3-dihydro-2,1-benzisothiazole-5-sulfonamide | 234 | 98 |
| N-{4-chloro-2-[(2-thienylsulfonyl)amino]phenyl}-1-methyl-3-oxo-1,3-dihydro-2,1-benzisothiazole-5-sulfonamide | 393 | 102 |
| N-1,3-benzodioxo1-4-yl-1-methyl-3-oxo-1,3-dihydro-2,1-benzisothiazole-5-sulfonamide | 1942 | 73 |
| N-[2-({[4-chloro-3-(trifluoromethyl)phenyl]sulfonyl}amino)phenyl]-1-methyl-3-oxo-1,3-dihydro-2,1-benzisothiazole-5-sulfonamide | 412 | 100 |

TABLE 1-continued shows activity for CCR2 receptor (IC$_{50}$) nM

| Name | CCR2 IC50 (nM) | CCR2 % ANTAG |
|---|---|---|
| 1-isopropyl-3-oxo-N-(2,2,3,3-tetrafluoro-2,3-dihydro-1,4-benzodioxin-5-yl)-1,3-dihydro-2,1-benzisothiazole-5-sulfonamide | 559 | 68 |
| N-{4,5-dichloro-2-[(2-thienylsulfonyl)amino]phenyl}-1-methyl-3-oxo-1,3-dihydro-2,1-benzisothiazole-5-sulfonamide | 361 | 99 |
| N-{5-chloro-2-[(2-thienylsulfonyl)amino]pyridin-3-yl}-1-methyl-3-oxo-1,3-dihydro-2,1-benzisothiazole-5-sulfonamide | 1009 | 48 |
| 1-methyl-3-oxo-N-[3-(trifluoromethoxy)phenyl]-1,3-dihydro-2,1-benzisothiazole-5-sulfonamide | 920 | 92 |
| N-dibenzo[b,e][1,4]dioxin-1-yl-1-methyl-3-oxo-1,3-dihydro-2,1-benzisothiazole-5-sulfonamide | 1456 | 67 |
| N-(7-chloro-2,3-dihydro-1,4-benzodioxin-5-yl)-1-methyl-3-oxo-1,3-dihydro-2,1-benzisothiazole-5-sulfonamide | 1672 | 63 |
| N-(2-{[(5-chloro-2-thienyl)sulfonyl]amino}phenyl)-1-methyl-3-oxo-1,3-dihydro-2,1-benzisothiazole-5-sulfonamide | 513 | 104 |
| N-(2-{[(4,5-dichloro-2-thienyl)sulfonyl]amino}phenyl)-1-methyl-3-oxo-1,3-dihydro-2,1-benzisothiazole-5-sulfonamide | 359 | 89 |
| 1-methyl-3-oxo-N-{2-[(phenylsulfonyl)amino]phenyl}-1,3-dihydro-2,1-benzisothiazole-5-sulfonamide | 887 | 97 |
| N-(2-{[(4-chlorophenyl)sulfonyl]amino}phenyl)-1-methyl-3-oxo-1,3-dihydro-2,1-benzisothiazole-5-sulfonamide | 1079 | 99 |
| N-{2-[(2-furylsulfonyl)amino]phenyl}-1-methyl-3-oxo-1,3-dihydro-2,1-benzisothiazole-5-sulfonamide | 744 | 104 |
| N-{5-bromo-2-[(2-thienylsulfonyl)amino]phenyl}-1-methyl-3-oxo-1,3-dihydro-2,1-benzisothiazole-5-sulfonamide | 537 | 100 |
| 1-methyl-3-oxo-N-{2-[(2-thienylsulfonyl)amino]-5-(trifluoromethyl)phenyl}-1,3-dihydro-2,1-benzisothiazole-5-sulfonamide | 701 | 103 |
| 1-methyl-N-(2-{[(1-methyl-1H-imidazol-4-yl)sulfonyl]amino}phenyl)-3-oxo-1,3-dihydro-2,1-benzisothiazole-5-sulfonamide | 963 | 99 |
| 1-methyl-N-(2-{[(1-methyl-1H-pyrazol-3-yl)sulfonyl]amino}phenyl)3-oxo-1,3-dihydro-2,1-benzisothiazole-5-sulfonamide | 1683 | 53 |
| 1-methyl-N-(2-{[(1-methyl-1H-pyrazol-4-yl)sulfonyl]amino}phenyl)3-oxo-1,3-dihydro-2,1-benzisothiazole-5-sulfonamide | 2476 | 60 |
| 1-methyl-N-{4-methyl-2-[(2-thienylsulfonyl)amino]phenyl}-3-oxo-1,3-dihydro-2,1-benzisothiazole-5-sulfonamide | 563 | 99 |
| N-{4-chloro-2-[(2-thienylsulfonyl)amino]-5-(trifluoromethyl)phenyl}-1-methyl-3-oxo-1,3-dihydro-2,1-benzisothiazole-5-sulfonamide | 522 | 87 |
| N-{5-methoxy-2-[(2-thienylsulfonyl)amino]phenyl}-1-methyl-3-oxo-1,3-dihydro-2,1-benzisothiazole-5-sulfonamide | 1408 | 104 |
| 1-methyl-3-oxo-N-{2-[(pyridin-3-ylsulfonyl)amino]phenyl}-1,3-dihydro-2,1-benzisothiazole-5-sulfonamide | nd | 77 |
| 1-methyl-3-oxo-N-{2-[(4H-1,2,4-triazol-3-ylsulfonyl)amino]phenyl}1,3-dihydro-2,1-benzisothiazole-5-sulfonamide | 1102 | 90 |
| N-{2-[(1H-imidazol-4-ylsulfonyl)amino]phenyl}-1-methyl-3-oxo-1,3-dihydro-2,1-benzisothiazole-5-sulfonamide | >8300.00 | 0 |
| N-(2-{[(3,4-dichlorophenyl)sulfonyl]amino}phenyl)-1-methyl-3-oxo-1,3-dihydro-2,1-benzisothiazole-5-sulfonamide | 522 | 92 |
| N-(2-{[(2,5-dichlorophenyl)sulfonyl]amino}phenyl)-1-methyl-3-oxo-1,3-dihydro-2,1-benzisothiazole-5-sulfonamide | 1814 | 99 |
| N-(2-{[(2-chlorophenyl)sulfonyl]amino}phenyl)-1-methyl-3-oxo-1,3-dihydro-2,1-benzisothiazole-5-sulfonamide | 1348 | 84 |
| N-(2-{[(2-fluorophenyl)sulfonyl]amino}phenyl)-1-methyl-3-oxo-1,3-dihydro-2,1-benzisothiazole-5-sulfonamide | 360 | 103 |
| N-[2-({[3,5-bis(trifluoromethyl)phenyl]sulfonyl}amino)phenyl]-1-methyl-3-oxo-1,3-dihydro-2,1-benzisothiazole-5-sulfonamide | 2072 | 94 |
| 1-methyl-N-{5-methyl-2-[(2-thienylsulfonyl)amino]phenyl}-3-oxo-1,3-dihydro-2,1-benzisothiazole-5-sulfonamide | 377 | 102 |
| N-{2-fluoro-6-[(2-thienylsulfonyl)amino]phenyl}-1-methyl-3-oxo-1,3-dihydro-2,1-benzisothiazole-5-sulfonamide | 471 | 105 |
| N-{5-cyano-2-[(2-thienylsulfonyl)amino]phenyl}-1-methyl-3-oxo-1,3-dihydro-2,1-benzisothiazole-5-sulfonamide | 2718 | 59 |
| N-[5-chloro-2-({[4-chloro-3-(trifluoromethyl)phenyl]sulfonyl]amino)phenyl]-1-methyl-3-oxo-1,3-dihydro-2,1-benzisothiazole-5-sulfonamide | 240 | 88 |
| methyl 3-{[(1-methyl-3-oxo-1,3-dihydro-2,1-benzisothiazol-5-yl)sulfonyl]amino}-4-[(2-thienylsulfonyl)amino]benzoate | 2409 | 76 |
| 1-methyl-3-oxo-N-[2-({[4-(trifluoromethyl)phenyl]sulfonyl}amino)phenyl]-1,3-dihydro-2,1-benzisothiazole-5-sulfonamide | 606 | 24 |
| N-{2-[(3-furylsulfonyl)amino]phenyl}-1-methyl-3-oxo-1,3-dihydro-2,1-benzisothiazole-5-sulfonamide | nd | 73 |
| 1-methyl-3-oxo-N-[2-({[3- | | |

TABLE 1-continued shows activity for CCR2 receptor (IC$_{50}$) nM

| Name | CCR2 IC50 (nM) | CCR2 % ANTAG |
|---|---|---|
| (trifluoromethyl)phenyl]sulfonyl}amino)phenyl]-1,3-dihydro-2,1-benzisothiazole-5-sulfonamide | 2215 | 94 |
| N-(2-{[(3,5-dichlorophenyl)sulfonyl]amino}phenyl)-1-methyl-3-oxo-1,3-dihydro-2,1-benzisothiazole-5-sulfonamide | 2567 | 95 |
| N-(2-{[(3,5-difluorophenyl)sulfonyl]amino}phenyl)-1-methyl-3-oxo-1,3-dihydro-2,1-benzisothiazole-5-sulfonamide | 438 | 96 |
| N-(2-{[(3-fluorophenyl)sulfonyl]amino}phenyl)-1-methyl-3-oxo-1,3-dihydro-2,1-benzisothiazole-5-sulfonamide | 2419 | 100 |
| N-(2-{[(4-methoxyphenyl)sulfonyl]amino}phenyl)-1-methyl-3-oxo-1,3-dihydro-2,1-benzisothiazole-5-sulfonamide | 2453 | 67 |
| N-(5-chloro-2-{[(3-chlorophenyl)sulfonyl]amino}phenyl)-1-methyl-3-oxo-1,3-dihydro-2,1-benzisothiazole-5-sulfonamide | 493 | 91 |
| N-(5-chloro-2-{[(3,4-dichlorophenyl)sulfonyl]amino}phenyl)-1-methyl-3-oxo-1,3-dihydro-2,1-benzisothiazole-5-sulfonamide | 1286 | 97 |
| N-{4-methoxy-2-[(2-thienylsulfonyl)amino]phenyl}-1-methyl-3-oxo-1,3-dihydro-2,1-benzisothiazole-5-sulfonamide | 1296 | 60 |
| N-{4,5-dimethyl-2-[(2-thienylsulfonyl)amino]phenyl}-1-methyl-3-oxo-1,3-dihydro-2,1-benzisothiazole-5-sulfonamide | 2191 | 91 |
| N-{4-cyano-2-[(2-thienylsulfonyl)amino]phenyl}-1-methyl-3-oxo-1,3-dihydro-2,1-benzisothiazole-5-sulfonamide | nd | 31 |
| methyl 4-{[(1-methyl-3-oxo-1,3-dihydro-2,1-benzisothiazol-5-yl)sulfonyl]amino}-3-[(2-thienylsulfonyl)amino]benzoate | >8300 | 0 |
| N-(5-chloro-2-{[(3,5-dichlorophenyl)sulfonyl]amino}phenyl)-1-methyl-3-oxo-1,3-dihydro-2,1-benzisothiazole-5-sulfonamide | 2602 | 94 |
| N-(5-chloro-2-{[(3-methoxyphenyl)sulfonyl]amino}phenyl)-1-methyl-3-oxo-1,3-dihydro-2,1-benzisothiazole-5-sulfonamide | 402 | 83 |
| N-(5-chloro-2-{[(5-methyl-2-thienyl)sulfonyl]amino}phenyl)-1-methyl-3-oxo-1,3-dihydro-2,1-benzisothiazole-5-sulfonamide | 497 | 95 |
| N-(5-chloro-2-{[(4-methoxyphenyl)sulfonyl]amino}phenyl)-1-methyl-3-oxo-1,3-dihydro-2,1-benzisothiazole-5-sulfonamide | 210 | 78 |
| N-(5-chloro-2-{[(3,4-dimethoxyphenyl)sulfonyl]amino}phenyl)-1-methyl-3-oxo-1,3-dihydro-2,1-benzisothiazole-5-sulfonamide | 1023 | 93 |
| N-{5-isopropyl-2-[(2-thienylsulfonyl)amino]phenyl}1-methyl-3-oxo-1,3-dihydro-2,1-benzisothiazole-5-sulfonamide | 425 | 85 |
| N-{4-isopropyl-2-[(2-thienylsulfonyl)amino]phenyl}-1-methyl-3-oxo-1,3-dihydro-2,1-benzisothiazole-5-sulfonamide | 886 | 87 |
| N-(5-chloro-2-{[(4-methylphenyl)sulfonyl]amino}phenyl)-1-methyl-3-oxo-1,3-dihydro-2,1-benzisothiazole-5-sulfonamide | 680 | 95 |
| N-(5-chloro-2-{[(4-hydroxyphenyl)sulfonyl]amino}phenyl)-1-methyl-3-oxo-1,3-dihydro-2,1-benzisothiazole-5-sulfonamide | 491 | 95 |
| N-{5-chloro-4-methyl-2-[(2-thienylsulfonyl)amino]phenyl}-1-methyl-3-oxo-1,3-dihydro-2,1-benzisothiazole-5-sulfonamide | 531 | 91 |
| N-{4-chloro-5-methyl-2-[(2-thienylsulfonyl)amino]phenyl}-1-methyl-3-oxo-1,3-dihydro-2,1-benzisothiazole-5-sulfonamide | 311 | 75 |
| N-[5-chloro-2-({[4-(dimethylamino)phenyl]sulfonyl}amino)phenyl]-1-methyl-3-oxo-1,3-dihydro-2,1-benzisothiazole-5-sulfonamide | 1653 | 64 |
| N-{5-(dimethylamino)-2-[(2-thienylsulfonyl)amino]phenyl}-1-methyl-3-oxo-1,3-dihydro-2,1-benzisothiazole-5-sulfonamide | 551 | 35 |
| N-{4-(dimethylamino)-2-[(2-thienylsulfonyl)amino]phenyl}-1-methyl-3-oxo-1,3-dihydro-2,1-benzisothiazole-5-sulfonamide | 1231 | 78 |
| N-(5-chloro-2-{[(4-isopropylphenyl)sulfonyl]amino}phenyl)-1-methyl-3-oxo-1,3-dihydro-2,1-benzisothiazole-5-sulfonamide | 985 | 94 |
| N-{5-chloro-2-[(2-thienylsulfonyl)amino]phenyl}-1-methyl-3-oxo-1,3-dihydro-2,1-benzisothiazole-5-carboxamide | nd | 99 |
| N-(5-chloro-2-{[(2-methoxyphenyl)sulfonyl]amino}phenyl)-1-methyl-3-oxo-1,3-dihydro-2,1-benzisothiazole-5-sulfonamide | 397 | 91 |
| N-(4-{[(4-chloro-2-{[(1-methyl-3-oxo-1,3-dihydro-2,1-benzisothiazol-5-yl)sulfonyl]amino}phenyl)amino]sulfonyl}phenyl)acetamide | 2230 | 80 |
| N-(4-chloro-2-{[(1-methyl-3-oxo-1,3-dihydro-2,1-benzisothiazol-5-yl)sulfonyl]amino}phenyl)-4-methoxybenzamide | nd | 56 |
| N-[5-chloro-2-({[3-(dimethylamino)phenyl]sulfonyl}amino)phenyl]-1-methyl-3-oxo-1,3-dihydro-2,1-benzisothiazole-5-sulfonamide | 678 | 69 |
| 1-methyl-3-oxo-N-{3-[(2-thienylsulfonyl)amino]-2-naphthyl}-1,3-dihydro-2,1-benzisothiazole-5-sulfonamide | 2178 | 96 |
| N-{5-ethyl-2-[(2-thienylsulfonyl)amino]phenyl}-1-methyl-3-oxo-1,3-dihydro-2,1-benzisothiazole-5-sulfonamide | 1936 | 94 |
| rel-1-methyl-3-oxo-N-{(1R,2R)-2-[(2-thienylsulfonyl)amino]cyclohexyl}-1,3-dihydro-2,1-benzisothiazole-5-sulfonamide | 2368 | 79 |
| 1-methyl-5-{[4-(2-thienylsulfonyl)-3,4-dihydroquinoxalin-1(2H)-yl+sulfonyl}-2,1-benzisothiazol-3(1H)-one | 2082 | 65 |
| N-(5-chloro-2-{[(4-ethoxyphenyl)sulfonyl]amino}phenyl)-1-methyl-3-oxo-1,3-dihydro-2,1-benzisothiazole-5-sulfonamide | 2787 | 84 |

TABLE 1-continued shows activity for CCR2 receptor (IC$_{50}$) nM

| Name | CCR2 IC50 (nM) | CCR2 % ANTAG |
|---|---|---|
| N-(5-chloro-2-{[(4-isopropoxyphenyl)sulfonyl]amino}phenyl)-1-methyl-3-oxo-1,3-dihydro-2,1-benzisothiazole-5-sulfonamide | nd | 72 |
| N-{5-chloro-2-[(2-thienylmethyl)amino]phenyl}-1-methyl-3-oxo-1,3-dihydro-2,1-benzisothiazole-5-sulfonamide | 1084 | 83 |
| N-(5-chloro-2-{[(2,4-dimethoxyphenyl)sulfonyl]amino}phenyl)-1-methyl-3-oxo-1,3-dihydro-2,1-benzisothiazole-5-sulfonamide | 1684 | 95 |
| N-(4,5-dichloro-2-{[(4-methoxyphenyl)sulfonyl]amino}phenyl)-1-methyl-3-oxo-1,3-dihydro-2,1-benzisothiazole-5-sulfonamide | 1013 | 86 |
| rel-1-methyl-3-oxo-N-{(1R,2S)-2-[(2-thienylsulfonyl)amino]cyclohexyl}-1,3-dihydro-2,1-benzisothiazole-5-sulfonamide | 2184 | 65 |
| N-(4,5-dichloro-2-{[(3-methoxyphenyl)sulfonyl]amino}phenyl)-1-methyl-3-oxo-1,3-dihydro-2,1-benzisothiazole-5-sulfonamide | 651 | 92 |
| N-{2-chloro-6-[(2-thienylsulfonyl)amino]phenyl}-1-methyl-3-oxo-1,3-dihydro-2,1-benzisothiazole-5-sulfonamide | 468 | 106 |
| N-(4,5-dichloro-2-{[(4,5-dichloro-2-thienyl)sulfonyl]amino}phenyl)-1-methyl-3-oxo-1,3-dihydro-2,1-benzisothiazole-5-sulfonamide | 2337 | 103 |
| N-[4,5-dichloro-2-({[4-chloro-3-(trifluoromethyl)phenyl]sulfonyl}amino)phenyl]-1-methyl-3-oxo-1,3-dihydro-2,1-benzisothiazole-5-sulfonamide | 529 | 84 |
| N-(4,5-dichloro-2-{[(5-methyl-2-thienyl)sulfonyl]amino}phenyl)-1-methyl-3-oxo-1,3-dihydro-2,1-benzisothiazole-5-sulfonamide | 851 | 95 |
| 1-methyl-3-oxo-N-{3-[(2-thienylsulfonyl)amino]phenyl}-1,3-dihydro-2,1-benzisothiazole-5-sulfonamide | 2870 | 23 |
| N-{1,1-dimethyl-2-[(2-thienylsulfonyl)amino]ethyl}-1-methyl-3-oxo-1,3-dihydro-2,1-benzisothiazole-5-sulfonamide | 2491 | 20 |
| 1-methyl-N-{3-methyl-2-[(2-thienylsulfonyl)amino]phenyl}-3-oxo-1,3-dihydro-2,1-benzisothiazole-5-sulfonamide | nd | 86 |
| N-{3-chloro-2-[(2-thienylsulfonyl)amino]phenyl}-1-methyl-3-oxo-1,3-dihydro-2,1-benzisothiazole-5-sulfonamide | 823 | 100 |
| 1-methyl-N-{2-methyl-2-[(2-thienylsulfonyl)amino]propyl}-3-oxo-1,3-dihydro-2,1-benzisothiazole-5-sulfonamide | nd | 30 |
| 1-methyl-3-oxo-N-(2-{[(2-thienylsulfonyl)amino]methyl}phenyl)-1,3-dihydro-2,1-benzisothiazole-5-sulfonamide | nd | 61 |
| 1-methyl-3-oxo-N-{2-[(2-thienylsulfonyl)amino]benzyl}-1,3-dihydro-2,1-benzisothiazole-5-sulfonamide | 2183 | 56 |
| rel-N-[(1R,2R)-2-{[(1-methyl-3-oxo-1,3-dihydro-2,1-benzisothiazol-5-yl)sulfonyl]amino}cyclohexyl]thiophene-2-carboxamide | nd | 46 |
| N-{3-methoxy-2-[(2-thienylsulfonyl)amino]phenyl}-1-methyl-3-oxo-1,3-dihydro-2,1-benzisothiazole-5-sulfonamide | nd | 52 |
| N-{1-[(1-methyl-3-oxo-1,3-dihydro-2,1-benzisothiazol-5-yl)sulfonyl]pyrrolidin-3-yl}thiophene-2-sulfonamide | 2764 | 44 |
| 1-methyl-3-oxo-N-[1-(2-thienylsulfonyl)pyrrolidin-3-yl]-1,3-dihydro 2,1-benzisothiazole-5-sulfonamide | nd | 22 |
| N-{1-[(1-methyl-3-oxo-1,3-dihydro-2,1-benzisothiazol-5-yl)sulfonyl]piperidin-3-yl}thiophene-2-sulfonamide | nd | 54 |
| 1-methyl-3-oxo-N-[1-(2-thienylsulfonyl)piperidin-3-yl]-1,3-dihydro-2,1-benzisothiazole-5-sulfonamide | nd | 39 |
| 1-methyl-3-oxo-N-(2-{[(2-thienylamino)carbonyl]amino}phenyl)-1,3-dihydro-2,1-benzisothiazole-5-sulfonamide | 2526 | 58 |
| 1-methyl-3-oxo-N-(2,4,5-trichlorophenyl)-1,3-dihydro-2,1-benzisothiazole-5-sulfonamide | 1661 | 79 |
| N-(3-chlorophenyl)-1-methyl-3-oxo-1,3-dihydro-2,1-benzisothiazole-5-sulfonamide | nd | 84 |
| 1-methyl-3-oxo-N-[3-(trifluoromethyl)phenyl]-1,3-dihydro-2,1-benzisothiazole-5-sulfonamide | nd | 84 |
| N-(3,4-dichlorophenyl)-1-methyl-3-oxo-1,3-dihydro-2,1-benzisothiazole-5-sulfonamide | 1180.63 | 94.08 |
| N-(4-chloro-2,5-dimethylphenyl)-1-methyl-3-oxo-1,3-dihydro-2,1-benzisothiazole-5-sulfonamide | 1851 | 80 |
| N-(4-chloro-2-methoxy-5-methylphenyl)-1-methyl-3-oxo-1,3-dihydro-2,1-benzisothiazole-5-sulfonamide | >8300 | 0 |
| N-(3-methoxyphenyl)-1-methyl-3-oxo-1,3-dihydro-2,1-benzisothiazole-5-sulfonamide | 2451 | 84 |
| 1-methyl-N-[3-(methylthio)phenyl]-3-oxo-1,3-dihydro-2,1-benzisothiazole-5-sulfonamide | 1188 | 86 |
| rel-N-[(1R,2R)-2-({[4-chloro-3-(trifluoromethyl)phenyl]sulfonyl}amino)cyclohexyl]-1-methyl-3-oxo-1,3-dihydro-2,1-benzisothiazole-5-sulfonamide | 543 | 96 |
| rel-N-[(1R,2S)-2-({[4-chloro-3-(trifluoromethyl)phenyl]sulfonyl}amino)cyclohexyl]-1-methyl-3-oxo-1,3-dihydro-2,1-benzisothiazole-5-sulfonamide | 1236 | 93 |

TABLE 1-continued shows activity for CCR2 receptor (IC$_{50}$) nM

| Name | CCR2 IC50 (nM) | CCR2 % ANTAG |
|---|---|---|
| 1-methyl-3-oxo-N-{3-[(trifluoromethyl)thio]phenyl}-1,3-dihydro-2,1 benzisothiazole-5-sulfonamide | nd | 85 |

What is claimed is:

1. A compound represented by Formula I, its enantiomers, diastereoisomers or a pharmaceutically acceptable salt thereof,

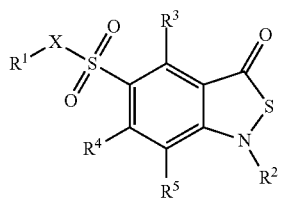

Formula I wherein:

R$^1$ is substituted or unsubstituted C$_{1-10}$ alkyl, substituted or unsubstituted heterocycle, substituted or unsubstituted C$_{3-10}$ cycloalkyl, substituted or unsubstituted C$_{3-10}$ cycloalkenyl or substituted or unsubstituted C$_{6-10}$ aryl;

R$^2$ is substituted or unsubstituted C$_{1-6}$ alkyl;

R$^3$ is H, substituted or unsubstituted C$_{1-6}$ alkyl, halogen, substituted or unsubstituted —OC$_{1-3}$ alkyl, CN, NO$_2$, C$_{2-6}$ alkenyl, C$_{2-6}$ alkynyl, C(O)R$^6$, NR$^7$R$^8$ or hydroxyl;

R$^4$ is H, substituted or unsubstituted C$_{1-6}$ alkyl, halogen, substituted or unsubstituted —OC$_{1-3}$ alkyl, CN, NO$_2$, C$_{2-6}$ alkenyl, C$_{2-6}$ alkynyl, C(O)R$^6$, NR$^7$R$^8$ or hydroxyl;

R$^5$ is H, substituted or unsubstituted C$_{1-6}$ alkyl, halogen, substituted or unsubstituted —OC$_{1-3}$ alkyl, CN, NO$_2$, C$_{2-6}$ alkenyl, C$_{2-6}$ alkynyl, C(O)R$^6$, NR$^7$R$^8$ or hydroxyl;

X is O, S or NH;

R$^6$ is H or substituted or unsubstituted C$_{1-6}$ alkyl;

R$^7$ is H or substituted or unsubstituted C$_{1-6}$ alkyl;

R$^8$ is H or substituted or unsubstituted C$_{1-6}$ alkyl;

with the proviso that the compound of Formula I does not have one of the following structures:

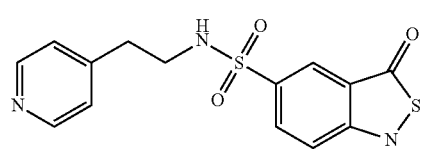

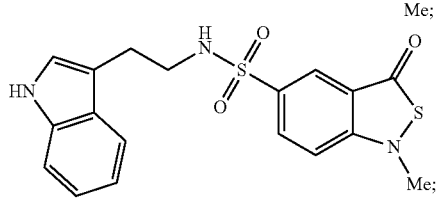

-continued

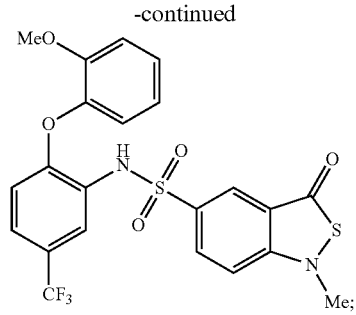

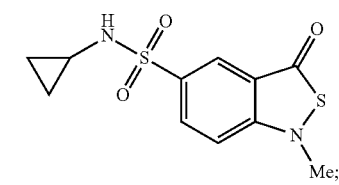

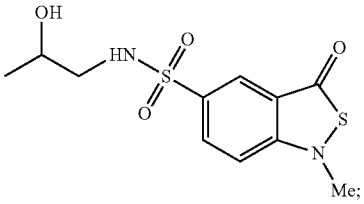

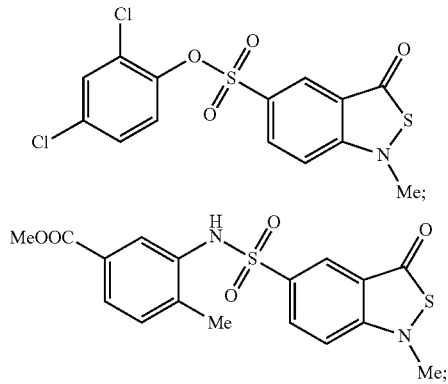

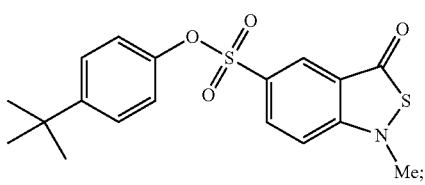

-continued

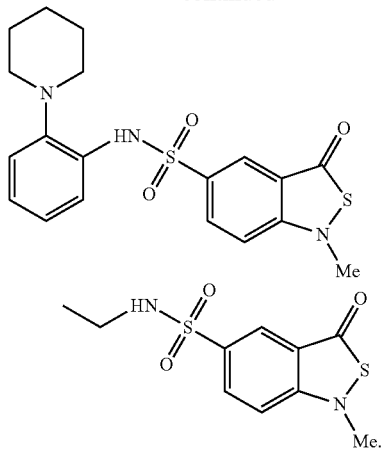
or

2. A compound according to claim 1, wherein:
R$^1$ is substituted or unsubstituted C$_{1-10}$ alkyl, substituted or unsubstituted heterocycle, or substituted or unsubstituted C$_{6-10}$ aryl;
R$^2$ is unsubstituted C$_{1-6}$ alkyl;
R$^3$ is H, substituted or unsubstituted C$_{1-6}$ alkyl, halogen;
R$^4$ is H, substituted or unsubstituted C$_{1-6}$ alkyl, halogen;
R$^5$ is H, substituted or unsubstituted C$_{1-6}$ alkyl, halogen;
X is O or NH;
with the proviso that the compound of Formula I does not have one of the following structures:

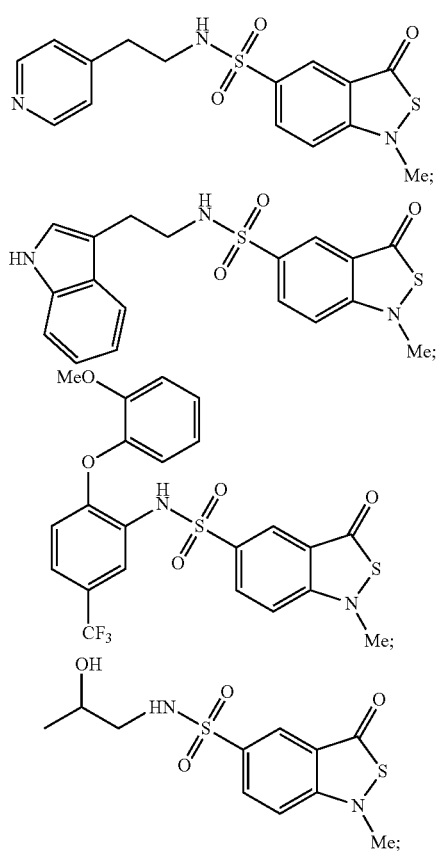

-continued

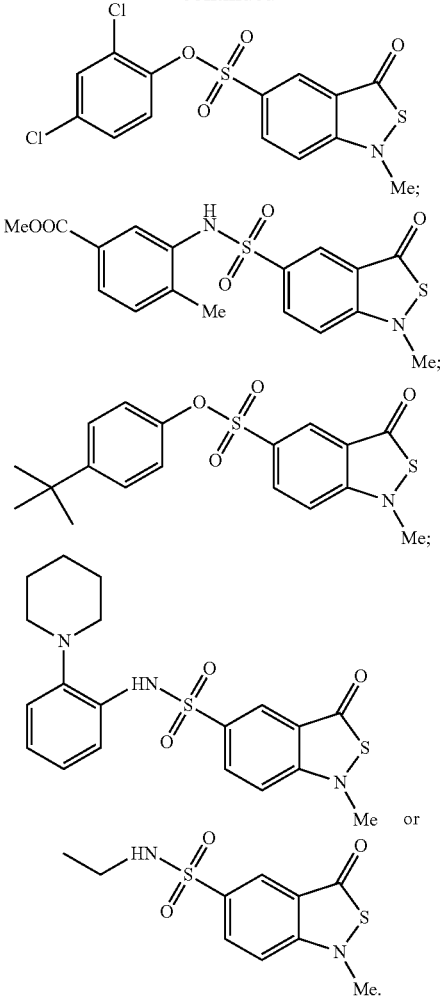

3. A compound according to claim 1, wherein:
R$^1$ is substituted or unsubstituted C$_{1-10}$ alkyl;
R$^2$ is unsubstituted C$_{1-6}$ alkyl;
R$^3$ is H;
R$^4$ is H;
R$^5$ is H;
X is NH;
with the proviso that the compound of Formula I does not have one of the following structures:

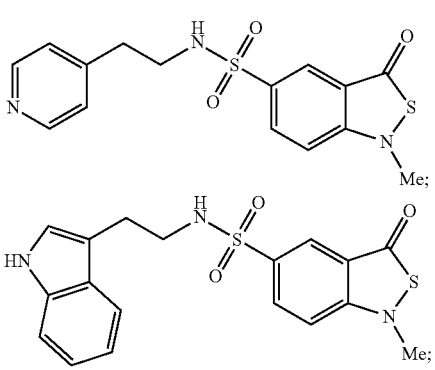

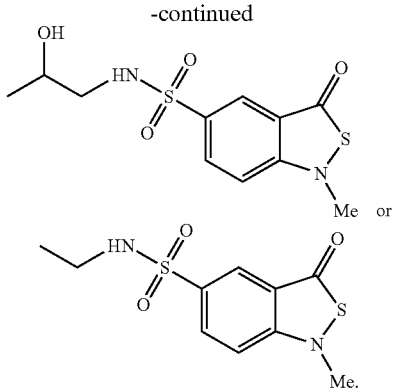

4. A compound according to claim 1, wherein:
$R^1$ is substituted or unsubstituted heterocycle,
$R^2$ is unsubstituted $C_{1-6}$ alkyl;
$R^3$ is H;
$R^4$ is H;
$R^5$ is H; and
X is NH.

5. A compound according to claim 1, wherein:
$R^1$ is substituted or unsubstituted $C_{6-10}$ aryl;
$R^2$ is unsubstituted $C_{1-6}$ alkyl;
$R^3$ is H;
$R^4$ is H;
$R^5$ is H;
X is O or NH;
with the proviso that the compound of Formula I does not have one of the following structures:

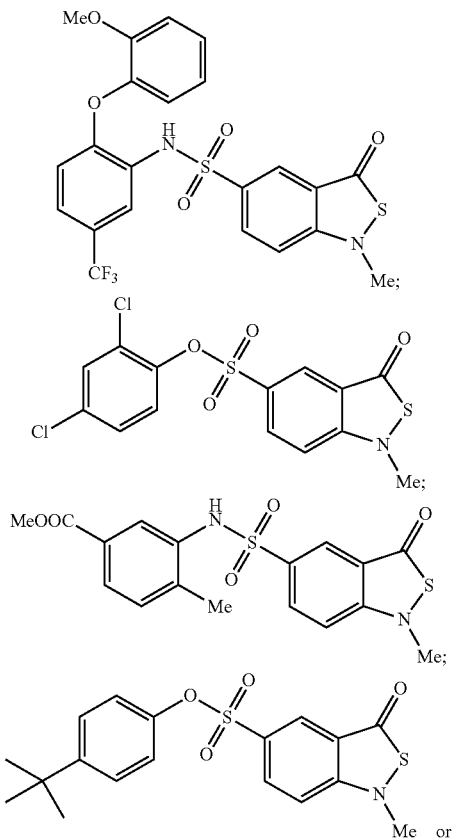

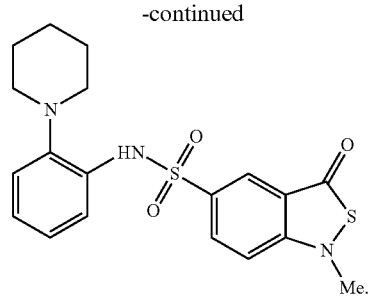

6. A compound according to claim 1, wherein:
$R^1$ is substituted or unsubstituted $C_{6-10}$ aryl;
$R^2$ is unsubstituted $C_{1-6}$ alkyl;
$R^3$ is H;
$R^4$ is H;
$R^5$ is H;
X is O;
with the proviso that the compound of Formula I does not have one of the following structures:

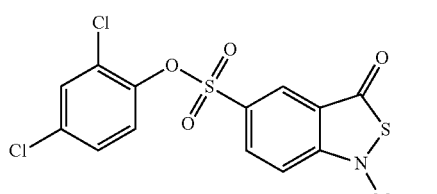

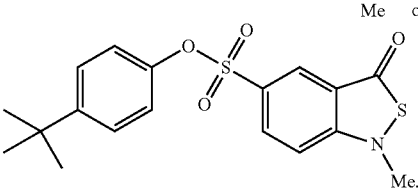

7. A compound according to claim 1, wherein:
$R^1$ is substituted or unsubstituted $C_{6-10}$ aryl;
$R^2$ is unsubstituted $C_{1-6}$ alkyl;
$R^3$ is H;
$R^4$ is H;
$R^5$ is H;
X is NH;
with the proviso that the compound of Formula I does not have one of the following structures:

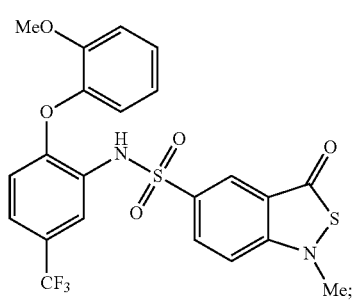

-continued

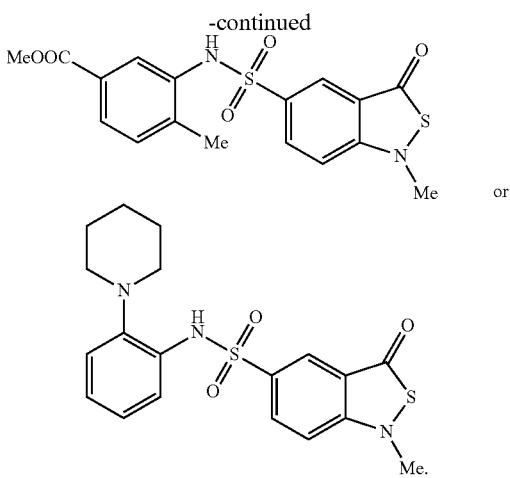

or

8. A compound according to claim 1, wherein:
R¹ is substituted or unsubstituted $C_{3-10}$ cycloalkyl;
R² is unsubstituted $C_{1-6}$ alkyl;
R³ is H;
R⁴ is H;
R⁵ is H;
X is NH;
with the proviso that the compound of Formula I does not have the following structure:

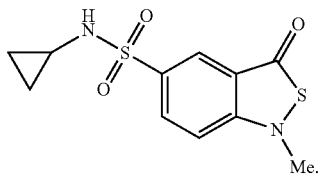 [SMILES: Cn1sc(=O)c2cc(S(=O)(=O)NC3CC3)ccc21]

9. A compound according to claim 1 selected from:
N-{5-chloro-2-[(4-oxopiperidin-1-yl)carbonyl]pyridin-3-yl}-1-methyl-3-oxo-1,3-dihydro-2,1-benzisothiazole-5-sulfonamide;
N-(2,3-dimethoxyphenyl)-1-methyl-3-oxo-1,3-dihydro-2,1-benzisothiazole-5-sulfonamide;
N-(2,3-dihydro-1,4-benzodioxin-5-yl)-1-methyl-3-oxo-1,3-dihydro-2,1-benzisothiazole-5-sulfonamide;
1-isopropyl-3-oxo-N-{2-[(2-thienylsulfonyl)amino]phenyl}-1,3-dihydro-2,1-benzisothiazole-5-sulfonamide;
N-(2,2-difluoro-1,3-benzodioxol-4-yl)-1-methyl-3-oxo-1,3-dihydro-2,1-benzisothiazole-5-sulfonamide;
1-methyl-3-oxo-N-{2-[(2-thienylsulfonyl)amino]pyridin-3-yl}-1,3-dihydro-2,1-benzisothiazole-5-sulfonamide;
N-{5-chloro-2-[(2-thienylsulfonyl)amino]phenyl}-1-methyl-3-oxo-1,3-dihydro-2,1-benzisothiazole-5-sulfonamide;
N-{4-chloro-2-[(2-thienylsulfonyl)amino]phenyl}-1-methyl-3-oxo-1,3-dihydro-2,1-benzisothiazole-5-sulfonamide;
N-1,3-benzodioxol-4-yl-1-methyl-3-oxo-1,3-dihydro-2,1-benzisothiazole-5-sulfonamide;
N-[2-({[4-chloro-3-(trifluoromethyl)phenyl]sulfonyl}amino)phenyl]-1-methyl-3-oxo-1,3-dihydro-2,1-benzisothiazole-5-sulfonamide;
1-isopropyl-3-oxo-N-(2,2,3,3-tetrafluoro-2,3-dihydro-1,4-benzodioxin-5-yl)-1,3-dihydro-2,1-benzisothiazole-5-sulfonamide;
N-{4,5-dichloro-2-[(2-thienylsulfonyl)amino]phenyl}-1-methyl-3-oxo-1,3-dihydro-2,1-benzisothiazole-5-sulfonamide;
N-{5-chloro-2-[(2-thienylsulfonyl)amino]pyridin-3-yl}-1-methyl-3-oxo-1,3-dihydro-2,1-benzisothiazole-5-sulfonamide;
1-methyl-3-oxo-N-[3-(trifluoromethoxy)phenyl]-1,3-dihydro-2,1-benzisothiazole-5-sulfonamide;
N-dibenzo[b,e][1,4]dioxin-1-yl-1-methyl-3-oxo-1,3-dihydro-2,1-benzisothiazole-5-sulfonamide;
N-(7-chloro-2,3-dihydro-1,4-benzodioxin-5-yl)-1-methyl-3-oxo-1,3-dihydro-2,1-benzisothiazole-5-sulfonamide;
N-(2-{[(5-chloro-2-thienyl)sulfonyl]amino}phenyl)-1-methyl-3-oxo-1,3-dihydro-2,1-benzisothiazole-5-sulfonamide;
N-(2-{[(4,5-dichloro-2-thienyl)sulfonyl]amino}phenyl)-1-methyl-3-oxo-1,3-dihydro-2,1-benzisothiazole-5-sulfonamide;
1-methyl-3-oxo-N-{2-[(phenylsulfonyl)amino]phenyl}-1,3-dihydro-2,1-benzisothiazole-5-sulfonamide;
N-(2-{[(4-chlorophenyl)sulfonyl]amino}phenyl)-1-methyl-3-oxo-1,3-dihydro-2,1-benzisothiazole-5-sulfonamide;
N-{2-[(2-furylsulfonyl)amino]phenyl}-1-methyl-3-oxo-1,3-dihydro-2,1-benzisothiazole-5-sulfonamide;
N-{5-bromo-2-[(2-thienylsulfonyl)amino]phenyl}-1-methyl-3-oxo-1,3-dihydro-2,1-benzisothiazole-5-sulfonamide;
1-methyl-3-oxo-N-{2-[(2-thienylsulfonyl)amino]-5-(trifluoromethyl)phenyl}-1,3-dihydro-2,1-benzisothiazole-5-sulfonamide;
1-methyl-N-(2-{[(1-methyl-1H-imidazol-4-yl)sulfonyl]amino}phenyl)-3-oxo-1,3-dihydro-2,1-benzisothiazole-5-sulfonamide;
1-methyl-N-(2-{[(1-methyl-1H-pyrazol-3-yl)sulfonyl]amino}phenyl)-3-oxo-1,3-dihydro-2,1-benzisothiazole-5-sulfonamide;
1-methyl-N-(2-{[(1-methyl-1H-pyrazol-4-yl)sulfonyl]amino}phenyl)-3-oxo-1,3-dihydro-2,1-benzisothiazole-5-sulfonamide;
1-methyl-N-{4-methyl-2-[(2-thienylsulfonyl)amino]phenyl}-3-oxo-1,3-dihydro-2,1-benzisothiazole-5-sulfonamide;
N-{4-chloro-2-[(2-thienylsulfonyl)amino]-5-(trifluoromethyl)phenyl}-1-methyl-3-oxo-1,3-dihydro-2,1-benzisothiazole-5-sulfonamide;
N-{5-methoxy-2-[(2-thienylsulfonyl)amino]phenyl}-1-methyl-3-oxo-1,3-dihydro-2,1-benzisothiazole-5-sulfonamide;
1-methyl-3-oxo-N-{2-[(pyridin-3-ylsulfonyl)amino]phenyl}-1,3-dihydro-2,1-benzisothiazole-5-sulfonamide;
1-methyl-3-oxo-N-{2-[(4H-1,2,4-triazol-3-ylsulfonyl)amino]phenyl}-1,3-dihydro-2,1-benzisothiazole-5-sulfonamide;
N-{2-[(1H-imidazol-4-ylsulfonyl)amino]phenyl}-1-methyl-3-oxo-1,3-dihydro-2,1-benzisothiazole-5-sulfonamide;
N-(2-{[(3,4-dichlorophenyl)sulfonyl]amino}phenyl)-1-methyl-3-oxo-1,3-dihydro-2,1-benzisothiazole-5-sulfonamide;
N-(2-{[(2,5-dichlorophenyl)sulfonyl]amino}phenyl)-1-methyl-3-oxo-1,3-dihydro-2,1-benzisothiazole-5-sulfonamide;
N-(2-{[(2-chlorophenyl)sulfonyl]amino}phenyl)-1-methyl-3-oxo-1,3-dihydro-2,1-benzisothiazole-5-sulfonamide;

N-(2-{[(2-fluorophenyl)sulfonyl]amino}phenyl)-1-methyl-3-oxo-1,3-dihydro-2,1-benzisothiazole-5-sulfonamide;
N-[2-({[3,5-bis(trifluoromethyl)phenyl]sulfonyl}amino)phenyl]-1-methyl-3-oxo-1,3-dihydro-2,1-benzisothiazole-5-sulfonamide;
1-methyl-N-{5-methyl-2-[(2-thienylsulfonyl)amino]phenyl}-3-oxo-1,3-dihydro-2,1-benzisothiazole-5-sulfonamide;
N-{2-fluoro-6-[(2-thienylsulfonyl)amino]phenyl}-1-methyl-3-oxo-1,3-dihydro-2,1-benzisothiazole-5-sulfonamide;
N-{5-cyano-2-[(2-thienylsulfonyl)amino]phenyl}-1-methyl-3-oxo-1,3-dihydro-2,1-benzisothiazole-5-sulfonamide;
N-[5-chloro-2-({[4-chloro-3-(trifluoromethyl)phenyl]sulfonyl}amino)phenyl]-1-methyl-3-oxo-1,3-dihydro-2,1-benzisothiazole-5-sulfonamide;
methyl 3-{[(1-methyl-3-oxo-1,3-dihydro-2,1-benzisothiazol-5-yl)sulfonyl]amino}-4-[(2-thienylsulfonyl)amino]benzoate;
1-methyl-3-oxo-N-[2-({[4-(trifluoromethyl)phenyl]sulfonyl}amino)phenyl]-1,3-dihydro-2,1-benzisothiazole-5-sulfonamide;
N-{2-[(3-furylsulfonyl)amino]phenyl}-1-methyl-3-oxo-1,3-dihydro-2,1-benzisothiazole-5-sulfonamide;
1-methyl-3-oxo-N-[2-({[3-(trifluoromethyl)phenyl]sulfonyl}amino)phenyl]-1,3-dihydro-2,1-benzisothiazole-5-sulfonamide;
N-(2-{[(3,5-dichlorophenyl)sulfonyl]amino}phenyl)-1-methyl-3-oxo-1,3-dihydro-2,1-benzisothiazole-5-sulfonamide;
N-(2-{[(3,5-difluorophenyl)sulfonyl]amino}phenyl)-1-methyl-3-oxo-1,3-dihydro-2,1-benzisothiazole-5-sulfonamide;
N-(2-{[(3-fluorophenyl)sulfonyl]amino}phenyl)-1-methyl-3-oxo-1,3-dihydro-2,1-benzisothiazole-5-sulfonamide;
N-(2-{[(4-methoxyphenyl)sulfonyl]amino}phenyl)-1-methyl-3-oxo-1,3-dihydro-2,1-benzisothiazole-5-sulfonamide;
N-(5-chloro-2-{[(3-chlorophenyl)sulfonyl]amino}phenyl)-1-methyl-3-oxo-1,3-dihydro-2,1-benzisothiazole-5-sulfonamide;
N-(5-chloro-2-{[(3,4-dichlorophenyl)sulfonyl]amino}phenyl)-1-methyl-3-oxo-1,3-dihydro-2,1-benzisothiazole-5-sulfonamide;
N-{4-methoxy-2-[(2-thienylsulfonyl)amino]phenyl}-1-methyl-3-oxo-1,3-dihydro-2,1-benzisothiazole-5-sulfonamide;
N-{4,5-dimethyl-2-[(2-thienylsulfonyl)amino]phenyl}-1-methyl-3-oxo-1,3-dihydro-2,1-benzisothiazole-5-sulfonamide;
N-{4-cyano-2-[(2-thienylsulfonyl)amino]phenyl}-1-methyl-3-oxo-1,3-dihydro-2,1-benzisothiazole-5-sulfonamide;
methyl 4-{[(1-methyl-3-oxo-1,3-dihydro-2,1-benzisothiazol-5-yl)sulfonyl]amino}-3-[(2-thienylsulfonyl)amino]benzoate;
N-(5-chloro-2-{[(3,5-dichlorophenyl)sulfonyl]amino}phenyl)-1-methyl-3-oxo-1,3-dihydro-2,1-benzisothiazole-5-sulfonamide;
N-(5-chloro-2-{[(3-methoxyphenyl)sulfonyl]amino}phenyl)-1-methyl-3-oxo-1,3-dihydro-2,1-benzisothiazole-5-sulfonamide;
N-(5-chloro-2-{[(5-methyl-2-thienyl)sulfonyl]amino}phenyl)-1-methyl-3-oxo-1,3-dihydro-2,1-benzisothiazole-5-sulfonamide;
N-(5-chloro-2-{[(4-methoxyphenyl)sulfonyl]amino}phenyl)-1-methyl-3-oxo-1,3-dihydro-2,1-benzisothiazole-5-sulfonamide;
N-(5-chloro-2-{[(3,4-dimethoxyphenyl)sulfonyl]amino}phenyl)-1-methyl-3-oxo-1,3-dihydro-2,1-benzisothiazole-5-sulfonamide;
N-{5-isopropyl-2-[(2-thienylsulfonyl)amino]phenyl}-1-methyl-3-oxo-1,3-dihydro-2,1-benzisothiazole-5-sulfonamide;
N-{4-isopropyl-2-[(2-thienylsulfonyl)amino]phenyl}-1-methyl-3-oxo-1,3-dihydro-2,1-benzisothiazole-5-sulfonamide;
N-(5-chloro-2-{[(4-methylphenyl)sulfonyl]amino}phenyl)-1-methyl-3-oxo-1,3-dihydro-2,1-benzisothiazole-5-sulfonamide;
N-(5-chloro-2-{[(4-hydroxyphenyl)sulfonyl]amino}phenyl)-1-methyl-3-oxo-1,3-dihydro-2,1-benzisothiazole-5-sulfonamide;
N-{5-chloro-4-methyl-2-[(2-thienylsulfonyl)amino]phenyl}-1-methyl-3-oxo-1,3-dihydro-2,1-benzisothiazole-5-sulfonamide;
N-{4-chloro-5-methyl-2-[(2-thienylsulfonyl)amino]phenyl}-1-methyl-3-oxo-1,3-dihydro-2,1-benzisothiazole-5-sulfonamide;
N-[5-chloro-2-({[4-(dimethylamino)phenyl]sulfonyl}amino)phenyl]-1-methyl-3-oxo-1,3-dihydro-2,1-benzisothiazole-5-sulfonamide;
N-{5-(dimethylamino)-2-[(2-thienylsulfonyl)amino]phenyl}-1-methyl-3-oxo-1,3-dihydro-2,1-benzisothiazole-5-sulfonamide;
N-{4-(dimethylamino)-2-[(2-thienylsulfonyl);amino]phenyl}-1-methyl-3-oxo-1,3-dihydro-2,1-benzisothiazole-5-sulfonamide;
N-(5-chloro-2-{[(4-isopropylphenyl)sulfonyl]amino}phenyl)-1-methyl-3-oxo-1,3-dihydro-2,1-benzisothiazole-5-sulfonamide;
N-(5-chloro-2-{[(2-methoxyphenyl)sulfonyl]amino}phenyl)-1-methyl-3-oxo-1,3-dihydro-2,1-benzisothiazole-5-sulfonamide;
N-(4-{[(4-chloro-2-{[(1-methyl-3-oxo-1,3-dihydro-2,1-benzisothiazol-5-yl)sulfonyl]amino}phenyl)amino]sulfonyl}phenyl)acetamide;
N-(4-chloro-2-{[(1-methyl-3-oxo-1,3-dihydro-2,1-benzisothiazol-5-yl)sulfonyl]amino}phenyl)-4-methoxybenzamide;
N-[5-chloro-2-({[3-(dimethylamino)phenyl]sulfonyl}amino)phenyl]-1-methyl-3-oxo-1,3-dihydro-2,1-benzisothiazole-5-sulfonamide;
1-methyl-3-oxo-N-{3-[(2-thienylsulfonyl)amino]-2-naphthyl}-1,3-dihydro-2,1-benzisothiazole-5-sulfonamide;
N-{5-ethyl-2-[(2-thienylsulfonyl)amino]phenyl}-1-methyl-3-oxo-1,3-dihydro-2,1-benzisothiazole-5-sulfonamide;
rel-1-methyl-3-oxo-N-{(1R,2R)-2-[(2-thienylsulfonyl)amino]cyclohexyl}-1,3-dihydro-2,1-benzisothiazole-5-sulfonamide;
N-(5-chloro-2-{[(4-ethoxyphenyl)sulfonyl]amino}phenyl)-1-methyl-3-oxo-1,3-dihydro-2,1-benzisothiazole-5-sulfonamide;
N-(5-chloro-2-{[(4-isopropoxyphenyl)sulfonyl]amino}phenyl)-1-methyl-3-oxo-1,3-dihydro-2,1-benzisothiazole-5-sulfonamide;

N-{5-chloro-2-[(2-thienylmethyl)amino]phenyl}-1-methyl-3-oxo-1,3-dihydro-2,1-benzisothiazole-5-sulfonamide;
N-(5-chloro-2-{[(2,4-dimethoxyphenyl)sulfonyl]amino}phenyl)-1-methyl-3-oxo-1,3-dihydro-2,1-benzisothiazole-5-sulfonamide;
N-(4,5-dichloro-2-{[(4-methoxyphenyl)sulfonyl]amino}phenyl)-1-methyl-3-oxo-1,3-dihydro-2,1-benzisothiazole-5-sulfonamide;
rel-1-methyl-3-oxo-N-{(1R,2S)-2-[(2-thienylsulfonyl)amino]cyclohexyl}-1,3-dihydro-2,1-benzisothiazole-5-sulfonamide;
N-(4,5-dichloro-2-{[(3-methoxyphenyl)sulfonyl]amino}phenyl)-1-methyl-3-oxo-1,3-dihydro-2,1-benzisothiazole-5-sulfonamide;
N-{2-chloro-6-[(2-thienylsulfonyl)amino]phenyl}-1-methyl-3-oxo-1,3-dihydro-2,1-benzisothiazole-5-sulfonamide;
N-(4,5-dichloro-2-{[(4,5-dichloro-2-thienyl)sulfonyl]amino}phenyl)-1-methyl-3-oxo-1,3-dihydro-2,1-benzisothiazole-5-sulfonamide;
N-[4,5-dichloro-2-({[4-chloro-3-(trifluoromethyl)phenyl]sulfonyl}amino)phenyl]-1-methyl-3-oxo-1,3-dihydro-2,1-benzisothiazole-5-sulfonamide;
N-(4,5-dichloro-2-{[(5-methyl-2-thienyl)sulfonyl]amino}phenyl)-1-methyl-3-oxo-1,3-dihydro-2,1-benzisothiazole-5-sulfonamide;
1-methyl-3-oxo-N-{3-[(2-thienylsulfonyl)amino]phenyl}-1,3-dihydro-2,1-benzisothiazole-5-sulfonamide;
N-{1,1-dimethyl-2-[(2-thienylsulfonyl)amino]ethyl}-1-methyl-3-oxo-1,3-dihydro-2,1-benzisothiazole-5-sulfonamide;
1-methyl-N-{3-methyl-2-[(2-thienylsulfonyl)amino]phenyl}-3-oxo-1,3-dihydro-2,1-benzisothiazole-5-sulfonamide;
N-{3-chloro-2-[(2-thienylsulfonyl)amino]phenyl}-1-methyl-3-oxo-1,3-dihydro-2,1-benzisothiazole-5-sulfonamide;
1-methyl-N-{2-methyl-2-[(2-thienylsulfonyl)amino]propyl}-3-oxo-1,3-dihydro-2,1-benzisothiazole-5-sulfonamide;
1-methyl-3-oxo-N-(2-{[(2-thienylsulfonyl)amino]methyl}phenyl)-1,3-dihydro-2,1-benzisothiazole-5-sulfonamide;
1-methyl-3-oxo-N-{2-[(2-thienylsulfonyl)amino]benzyl}-1,3-dihydro-2,1-benzisothiazole-5-sulfonamide;
rel-N-[(1R,2R)-2-{[(1-methyl-3-oxo-1,3-dihydro-2,1-benzisothiazol-5-yl)sulfonyl]amino}cyclohexyl]thiophene-2-carboxamide;
N-{3-methoxy-2-[(2-thienylsulfonyl)amino]phenyl}-1-methyl-3-oxo-1,3-dihydro-2,1-benzisothiazole-5-sulfonamide;
N-{1-[(1-methyl-3-oxo-1,3-dihydro-2,1-benzisothiazol-5-yl)sulfonyl]pyrrolidin-3-yl}thiophene-2-sulfonamide;
1-methyl-3-oxo-N-[1-(2-thienylsulfonyl)pyrrolidin-3-yl]-1,3-dihydro-2,1-benzisothiazole-5-sulfonamide;
1-methyl-3-oxo-N-[1-(2-thienylsulfonyl)piperidin-3-yl]-1,3-dihydro-2,1-benzisothiazole-5-sulfonamide;
1-methyl-3-oxo-N-(2-{[(2-thienylamino)carbonyl]amino}phenyl)-1,3-dihydro-2,1-benzisothiazole-5-sulfonamide;
1-methyl-3-oxo-N-(2,4,5-trichlorophenyl)-1,3-dihydro-2,1-benzisothiazole-5-sulfonamide;
N-(3-chlorophenyl)-1-methyl-3-oxo-1,3-dihydro-2,1-benzisothiazole-5-sulfonamide;
1-methyl-3-oxo-N-[3-(trifluoromethyl)phenyl]-1,3-dihydro-2,1-benzisothiazole-5-sulfonamide;
N-(3,4-dichlorophenyl)-1-methyl-3-oxo-1,3-dihydro-2,1-benzisothiazole-5-sulfonamide;
N-(4-chloro-2,5-dimethylphenyl)-1-methyl-3-oxo-1,3-dihydro-2,1-benzisothiazole-5-sulfonamide;
N-(4-chloro-2-methoxy-5-methylphenyl)-1-methyl-3-oxo-1,3-dihydro-2,1-benzisothiazole-5-sulfonamide;
N-(3-methoxyphenyl)-1-methyl-3-oxo-1,3-dihydro-2,1-benzisothiazole-5-sulfonamide;
1-methyl-N-[3-(methylthio)phenyl]-3-oxo-1,3-dihydro-2,1-benzisothiazole-5-sulfonamide;
rel-N-[(1R,2R)-2-({[4-chloro-3-(trifluoromethyl)phenyl]sulfonyl}amino)cyclohexyl]-1-methyl-3-oxo-1,3-dihydro-2,1-benzisothiazole-5-sulfonamide;
rel-N-[(1R,2S)-2-({[4-chloro-3-(trifluoromethyl)phenyl]sulfonyl}amino)cyclohexyl]-1-methyl-3-oxo-1,3-dihydro-2,1-benzisothiazole-5-sulfonamide; and
1-methyl-3-oxo-N-{3-[(trifluoromethyl)thio]phenyl}-1,3-dihydro-2,1-benzisothiazole-5-sulfonamide.

10. A pharmaceutical composition comprising as active ingredient a therapeutically effective amount of a compound according to claim 1 and a pharmaceutically acceptable adjuvant, diluent or carrier.

11. A pharmaceutical composition according to claim 10 wherein the compound is selected from:
N-{5-chloro-2-[(4-oxopiperidin-1-yl)carbonyl]pyridin-3-yl}-1-methyl-3-oxo-1,3-dihydro-2,1-benzisothiazole-5-sulfonamide;
N-(2,3-dimethoxyphenyl)-1-methyl-3-oxo-1,3-dihydro-2,1-benzisothiazole-5-sulfonamide;
N-(2,3-dihydro-1,4-benzodioxin-5-yl)-1-methyl-3-oxo-1,3-dihydro-2,1-benzisothiazole-5-sulfonamide;
1-isopropyl-3-oxo-N-{2-[(2-thienylsulfonyl)amino]phenyl}-1,3-dihydro-2,1-benzisothiazole-5-sulfonamide;
N-(2,2-difluoro-1,3-benzodioxol-4-yl)-1-methyl-3-oxo-1,3-dihydro-2,1-benzisothiazole-5-sulfonamide;
1-methyl-3-oxo-N-{2-[(2-thienylsulfonyl)amino]pyridin-3-yl}-1,3-dihydro-2,1-benzisothiazole-5-sulfonamide;
N-{5-chloro-2-[(2-thienylsulfonyl)amino]phenyl}-1-methyl-3-oxo-1,3-dihydro-2,1-benzisothiazole-5-sulfonamide;
N-{4-chloro-2-[(2-thienylsulfonyl)amino]phenyl}-1-methyl-3-oxo-1,3-dihydro-2,1-benzisothiazole-5-sulfonamide;
N-1,3-benzodioxol-4-yl-1-methyl-3-oxo-1,3-dihydro-2,1-benzisothiazole-5-sulfonamide;
N-[2-({[4-chloro-3-(trifluoromethyl)phenyl]sulfonyl}amino)phenyl]-1-methyl-3-oxo-1,3-dihydro-2,1-benzisothiazole-5-sulfonamide;
1-isopropyl-3-oxo-N-(2,2,3,3-tetrafluoro-2,3-dihydro-1,4-benzodioxin-5-yl)-1,3-dihydro-2,1-benzisothiazole-5-sulfonamide;
N-{4,5-dichloro-2-[(2-thienylsulfonyl)amino]phenyl}-1-methyl-3-oxo-1,3-dihydro-2,1-benzisothiazole-5-sulfonamide;
N-{5-chloro-2-[(2-thienylsulfonyl)amino]pyridin-3-yl}-1-methyl-3-oxo-1,3-dihydro-2,1-benzisothiazole-5-sulfonamide;
1-methyl-3-oxo-N-[3-(trifluoromethoxy)phenyl]-1,3-dihydro-2,1-benzisothiazole-5-sulfonamide;
N-dibenzo[b,e][1,4]dioxin-1-yl-1-methyl-3-oxo-1,3-dihydro-2,1-benzisothiazole-5-sulfonamide;
N-(7-chloro-2,3-dihydro-1,4-benzodioxin-5-yl)-1-methyl-3-oxo-1,3-dihydro-2,1-benzisothiazole-5-sulfonamide;

N-(2-{[(5-chloro-2-thienyl)sulfonyl]amino}phenyl)-1-methyl-3-oxo-1,3-dihydro-2,1-benzisothiazole-5-sulfonamide;
N-(2-{[(4,5-dichloro-2-thienyl)sulfonyl]amino}phenyl)-1-methyl-3-oxo-1,3-dihydro-2,1-benzisothiazole-5-sulfonamide;
1-methyl-3-oxo-N-{2-[(phenylsulfonyl)amino]phenyl}-1,3-dihydro-2,1-benzisothiazole-5-sulfonamide;
N-(2-{[(4-chlorophenyl)sulfonyl]amino}phenyl)-1-methyl-3-oxo-1,3-dihydro-2,1-benzisothiazole-5-sulfonamide;
N-{2-[(2-furylsulfonyl)amino]phenyl}-1-methyl-3-oxo-1,3-dihydro-2,1-benzisothiazole-5-sulfonamide;
N-{5-bromo-2-[(2-thienylsulfonyl)amino]phenyl}-1-methyl-3-oxo-1,3-dihydro-2,1-benzisothiazole-5-sulfonamide;
1-methyl-3-oxo-N-{2-[(2-thienylsulfonyl)amino]-5-(trifluoromethyl)phenyl}-1,3-dihydro-2,1-benzisothiazole-5-sulfonamide;
1-methyl-N-(2-{[(1-methyl-1H-imidazol-4-yl)sulfonyl]amino}phenyl)-3-oxo-1,3-dihydro-2,1-benzisothiazole-5-sulfonamide;
1-methyl-N-(2-{[(1-methyl-1H-pyrazol-3-yl)sulfonyl]amino}phenyl)-3-oxo-1,3-dihydro-2,1-benzisothiazole-5-sulfonamide;
1-methyl-N-(2-{[(1-methyl-1H-pyrazol-4-yl)sulfonyl]amino}phenyl)-3-oxo-1,3-dihydro-2,1-benzisothiazole-5-sulfonamide;
1-methyl-N-{4-methyl-2-[(2-thienylsulfonyl)amino]phenyl}-3-oxo-1,3-dihydro-2,1-benzisothiazole-5-sulfonamide;
N-{4-chloro-2-[(2-thienylsulfonyl)amino]-5-(trifluoromethyl)phenyl}-1-methyl-3-oxo-1,3-dihydro-2,1-benzisothiazole-5-sulfonamide;
N-{5-methoxy-2-[(2-thienylsulfonyl)amino]phenyl}-1-methyl-3-oxo-1,3-dihydro-2,1-benzisothiazole-5-sulfonamide;
1-methyl-3-oxo-N-{2-[(pyridin-3-ylsulfonyl)amino]phenyl}-1,3-dihydro-2,1-benzisothiazole-5-sulfonamide;
1-methyl-3-oxo-N-{2-[(4H-1,2,4-triazol-3-ylsulfonyl)amino]phenyl}-1,3-dihydro-2,1-benzisothiazole-5-sulfonamide;
N-{2-[(1H-imidazol-4-ylsulfonyl)amino]phenyl}-1-methyl-3-oxo-1,3-dihydro-2,1-benzisothiazole-5-sulfonamide;
N-(2-{[(3,4-dichlorophenyl)sulfonyl]amino}phenyl)-1-methyl-3-oxo-1,3-dihydro-2,1-benzisothiazole-5-sulfonamide;
N-(2-{[(2,5-dichlorophenyl)sulfonyl]amino}phenyl)-1-methyl-3-oxo-1,3-dihydro-2,1-benzisothiazole-5-sulfonamide;
N-(2-{[(2-chlorophenyl)sulfonyl]amino}phenyl)-1-methyl-3-oxo-1,3-dihydro-2,1-benzisothiazole-5-sulfonamide;
N-(2-{[(2-fluorophenyl)sulfonyl]amino}phenyl)-1-methyl-3-oxo-1,3-dihydro-2,1-benzisothiazole-5-sulfonamide;
N-[2-({[3,5-bis(trifluoromethyl)phenyl]sulfonyl}amino)phenyl]-1-methyl-3-oxo-1,3-dihydro-2,1-benzisothiazole-5-sulfonamide;
1-methyl-N-{5-methyl-2-[(2-thienylsulfonyl)amino]phenyl}-3-oxo-1,3-dihydro-2,1-benzisothiazole-5-sulfonamide;
N-{2-fluoro-6-[(2-thienylsulfonyl)amino]phenyl}-1-methyl-3-oxo-1,3-dihydro-2,1-benzisothiazole-5-sulfonamide;
N-{5-cyano-2-[(2-thienylsulfonyl)amino]phenyl}-1-methyl-3-oxo-1,3-dihydro-2,1-benzisothiazole-5-sulfonamide;
N-[5-chloro-2-({[4-chloro-3-(trifluoromethyl)phenyl]sulfonyl}amino)phenyl]-1-methyl-3-oxo-1,3-dihydro-2,1-benzisothiazole-5-sulfonamide;
methyl 3-{[(1-methyl-3-oxo-1,3-dihydro-2,1-benzisothiazol-5-yl)sulfonyl]amino}-4-[(2-thienylsulfonyl)amino]benzoate;
1-methyl-3-oxo-N-[2-({[4-(trifluoromethyl)phenyl]sulfonyl}amino)phenyl]-1,3-dihydro-2,1-benzisothiazole-5-sulfonamide;
N-{2-[(3-furylsulfonyl)amino]phenyl}-1-methyl-3-oxo-1,3-dihydro-2,1-benzisothiazole-5-sulfonamide;
1-methyl-3-oxo-N-[2-({[3-(trifluoromethyl)phenyl]sulfonyl}amino)phenyl]-1,3-dihydro-2,1-benzisothiazole-5-sulfonamide;
N-(2-{[(3,5-dichlorophenyl)sulfonyl]amino}phenyl)-1-methyl-3-oxo-1,3-dihydro-2,1-benzisothiazole-5-sulfonamide;
N-(2-{[(3,5-difluorophenyl)sulfonyl]amino}phenyl)-1-methyl-3-oxo-1,3-dihydro-2,1-benzisothiazole-5-sulfonamide;
N-(2-{[(3-fluorophenyl)sulfonyl]amino}phenyl)-1-methyl-3-oxo-1,3-dihydro-2,1-benzisothiazole-5-sulfonamide;
N-(2-{[(4-methoxyphenyl)sulfonyl]amino}phenyl)-1-methyl-3-oxo-1,3-dihydro-2,1-benzisothiazole-5-sulfonamide;
N-(5-chloro-2-{[(3-chlorophenyl)sulfonyl]amino}phenyl)-1-methyl-3-oxo-1,3-dihydro-2,1-benzisothiazole-5-sulfonamide;
N-(5-chloro-2-{[(3,4-dichlorophenyl)sulfonyl]amino}phenyl)-1-methyl-3-oxo-1,3-dihydro-2,1-benzisothiazole-5-sulfonamide;
N-{4-methoxy-2-[(2-thienylsulfonyl)amino]phenyl}-1-methyl-3-oxo-1,3-dihydro-2,1-benzisothiazole-5-sulfonamide;
N-{4,5-dimethyl-2-[(2-thienylsulfonyl)amino]phenyl}-1-methyl-3-oxo-1,3-dihydro-2,1-benzisothiazole-5-sulfonamide;
N-{4-cyano-2-[(2-thienylsulfonyl)amino]phenyl}-1-methyl-3-oxo-1,3-dihydro-2,1-benzisothiazole-5-sulfonamide;
methyl 4-{[(1-methyl-3-oxo-1,3-dihydro-2,1-benzisothiazol-5-yl)sulfonyl]amino}-3-[(2-thienylsulfonyl)amino]benzoate;
N-(5-chloro-2-{[(3,5-dichlorophenyl)sulfonyl]amino}phenyl)-1-methyl-3-oxo-1,3-dihydro-2,1-benzisothiazole-5-sulfonamide;
N-(5-chloro-2-{[(3-methoxyphenyl)sulfonyl]amino}phenyl)-1-methyl-3-oxo-1,3-dihydro-2,1-benzisothiazole-5-sulfonamide;
N-(5-chloro-2-{[(5-methyl-2-thienyl)sulfonyl]amino}phenyl)-1-methyl-3-oxo-1,3-dihydro-2,1-benzisothiazole-5-sulfonamide;
N-(5-chloro-2-{[(4-methoxyphenyl)sulfonyl]amino}phenyl)-1-methyl-3-oxo-1,3-dihydro-2,1-benzisothiazole-5-sulfonamide;
N-(5-chloro-2-{[(3,4-dimethoxyphenyl)sulfonyl]amino}phenyl)-1-methyl-3-oxo-1,3-dihydro-2,1-benzisothiazole-5-sulfonamide;
N-{5-isopropyl-2-[(2-thienylsulfonyl)amino]phenyl}-1-methyl-3-oxo-1,3-dihydro-2,1-benzisothiazole-5-sulfonamide;

N-{4-isopropyl-2-[(2-thienylsulfonyl)amino]phenyl}-1-methyl-3-oxo-1,3-dihydro-2,1-benzisothiazole-5-sulfonamide;
N-(5-chloro-2-{[(4-methylphenyl)sulfonyl]amino}phenyl)-1-methyl-3-oxo-1,3-dihydro-2,1-benzisothiazole-5-sulfonamide;
N-(5-chloro-2-{[(4-hydroxyphenyl)sulfonyl]amino}phenyl)-1-methyl-3-oxo-1,3-dihydro-2,1-benzisothiazole-5-sulfonamide;
N-{5-chloro-4-methyl-2-[(2-thienylsulfonyl)amino]phenyl}-1-methyl-3-oxo-1,3-dihydro-2,1-benzisothiazole-5-sulfonamide;
N-{4-chloro-5-methyl-2-[(2-thienylsulfonyl)amino]phenyl}-1-methyl-3-oxo-1,3-dihydro-2,1-benzisothiazole-5-sulfonamide;
N-[5-chloro-2-({[4-(dimethylamino)phenyl]sulfonyl}amino)phenyl]-1-methyl-3-oxo-1,3-dihydro-2,1-benzisothiazole-5-sulfonamide;
N-{5-(dimethylamino)-2-[(2-thienylsulfonyl)amino]phenyl}-1-methyl-3-oxo-1,3-dihydro-2,1-benzisothiazole-5-sulfonamide;
N-{4-(dimethylamino)-2-[(2-thienylsulfonyl);amino]phenyl}-1-methyl-3-oxo-1,3-dihydro-2,1-benzisothiazole-5-sulfonamide;
N-(5-chloro-2-{[(4-isopropylphenyl)sulfonyl]amino}phenyl)-1-methyl-3-oxo-1,3-dihydro-2,1-benzisothiazole-5-sulfonamide;
N-(5-chloro-2-{[(2-methoxyphenyl)sulfonyl]amino}phenyl)-1-methyl-3-oxo-1,3-dihydro-2,1-benzisothiazole-5-sulfonamide;
N-(4-{[(4-chloro-2-{[(1-methyl-3-oxo-1,3-dihydro-2,1-benzisothiazol-5-yl)sulfonyl]amino}phenyl)amino]sulfonyl}phenyl)acetamide;
N-(4-chloro-2-{[(1-methyl-3-oxo-1,3-dihydro-2,1-benzisothiazol-5-yl)sulfonyl]amino}phenyl)-4-methoxybenzamide;
N-[5-chloro-2-({[3-(dimethylamino)phenyl]sulfonyl}amino)phenyl]-1-methyl-3-oxo-1,3-dihydro-2,1-benzisothiazole-5-sulfonamide;
1-methyl-3-oxo-N-{3-[(2-thienylsulfonyl)amino]-2-naphthyl}-1,3-dihydro-2,1-benzisothiazole-5-sulfonamide;
N-{5-ethyl-2-[(2-thienylsulfonyl)amino]phenyl}-1-methyl-3-oxo-1,3-dihydro-2,1-benzisothiazole-5-sulfonamide;
rel-1-methyl-3-oxo-N-{(1R,2R)-2-[(2-thienylsulfonyl)amino]cyclohexyl}-1,3-dihydro-2,1-benzisothiazole-5-sulfonamide
N-(5-chloro-2-{[(4-ethoxyphenyl)sulfonyl]amino}phenyl)-1-methyl-3-oxo-1,3-dihydro-2,1-benzisothiazole-5-sulfonamide;
N-(5-chloro-2-{[(4-isopropoxyphenyl)sulfonyl]amino}phenyl)-1-methyl-3-oxo-1,3-dihydro-2,1-benzisothiazole-5-sulfonamide;
N-{5-chloro-2-[(2-thienylmethyl)amino]phenyl}-1-methyl-3-oxo-1,3-dihydro-2,1-benzisothiazole-5-sulfonamide;
N-(5-chloro-2-{[(2,4-dimethoxyphenyl)sulfonyl]amino}phenyl)-1-methyl-3-oxo-1,3-dihydro-2,1-benzisothiazole-5-sulfonamide;
N-(4,5-dichloro-2-{[(4-methoxyphenyl)sulfonyl]amino}phenyl)-1-methyl-3-oxo-1,3-dihydro-2,1-benzisothiazole-5-sulfonamide;
rel-1-methyl-3-oxo-N-{(1R,2S)-2-[(2-thienylsulfonyl)amino]cyclohexyl}-1,3-dihydro-2,1-benzisothiazole-5-sulfonamide;
N-(4,5-dichloro-2-{[(3-methoxyphenyl)sulfonyl]amino}phenyl)-1-methyl-3-oxo-1,3-dihydro-2,1-benzisothiazole-5-sulfonamide;
N-{2-chloro-6-[(2-thienylsulfonyl)amino]phenyl}-1-methyl-3-oxo-1,3-dihydro-2,1-benzisothiazole-5-sulfonamide;
N-(4,5-dichloro-2-{[(4,5-dichloro-2-thienyl)sulfonyl]amino}phenyl)-1-methyl-3-oxo-1,3-dihydro-2,1-benzisothiazole-5-sulfonamide;
N-[4,5-dichloro-2-({[4-chloro-3-(trifluoromethyl)phenyl]sulfonyl}amino)phenyl]-1-methyl-3-oxo-1,3-dihydro-2,1-benzisothiazole-5-sulfonamide;
N-(4,5-dichloro-2-{[(5-methyl-2-thienyl)sulfonyl]amino}phenyl)-1-methyl-3-oxo-1,3-dihydro-2,1-benzisothiazole-5-sulfonamide;
1-methyl-3-oxo-N-{3-[(2-thienylsulfonyl)amino]phenyl}-1,3-dihydro-2,1-benzisothiazole-5-sulfonamide;
N-{1,1-dimethyl-2-[(2-thienylsulfonyl)amino]ethyl}-1-methyl-3-oxo-1,3-dihydro-2,1-benzisothiazole-5-sulfonamide;
1-methyl-N-{3-methyl-2-[(2-thienylsulfonyl)amino]phenyl}-3-oxo-1,3-dihydro-2,1-benzisothiazole-5-sulfonamide;
N-{3-chloro-2-[(2-thienylsulfonyl)amino]phenyl}-1-methyl-3-oxo-1,3-dihydro-2,1-benzisothiazole-5-sulfonamide;
1-methyl-N-{2-methyl-2-[(2-thienylsulfonyl)amino]propyl}-3-oxo-1,3-dihydro-2,1-benzisothiazole-5-sulfonamide;
1-methyl-3-oxo-N-(2-{[(2-thienylsulfonyl)amino]methyl}phenyl)-1,3-dihydro-2,1-benzisothiazole-5-sulfonamide;
1-methyl-3-oxo-N-{2-[(2-thienylsulfonyl)amino]benzyl}-1,3-dihydro-2,1-benzisothiazole-5-sulfonamide;
rel-N-[(1R,2R)-2-{[(1-methyl-3-oxo-1,3-dihydro-2,1-benzisothiazol-5-yl)sulfonyl]amino}cyclohexyl]thiophene-2-carboxamide;
N-{3-methoxy-2-[(2-thienylsulfonyl)amino]phenyl}-1-methyl-3-oxo-1,3-dihydro-2,1-benzisothiazole-5-sulfonamide;
N-{1-[(1-methyl-3-oxo-1,3-dihydro-2,1-benzisothiazol-5-yl)sulfonyl]pyrrolidin-3-yl}thiophene-2-sulfonamide;
1-methyl-3-oxo-N-[1-(2-thienylsulfonyl)pyrrolidin-3-yl]-1,3-dihydro-2,1-benzisothiazole-5-sulfonamide;
1-methyl-3-oxo-N-[1-(2-thienylsulfonyl)piperidin-3-yl]-1,3-dihydro-2,1-benzisothiazole-5-sulfonamide;
1-methyl-3-oxo-N-(2-{[(2-thienylamino)carbonyl]amino}phenyl)-1,3-dihydro-2,1-benzisothiazole-5-sulfonamide;
1-methyl-3-oxo-N-(2,4,5-trichlorophenyl)-1,3-dihydro-2,1-benzisothiazole-5-sulfonamide;
N-(3-chlorophenyl)-1-methyl-3-oxo-1,3-dihydro-2,1-benzisothiazole-5-sulfonamide;
1-methyl-3-oxo-N-[3-(trifluoromethyl)phenyl]-1,3-dihydro-2,1-benzisothiazole-5-sulfonamide;
N-(3,4-dichlorophenyl)-1-methyl-3-oxo-1,3-dihydro-2,1-benzisothiazole-5-sulfonamide;
N-(4-chloro-2,5-dimethylphenyl)-1-methyl-3-oxo-1,3-dihydro-2,1-benzisothiazole-5-sulfonamide;
N-(4-chloro-2-methoxy-5-methylphenyl)-1-methyl-3-oxo-1,3-dihydro-2,1-benzisothiazole-5-sulfonamide;
N-(3-methoxyphenyl)-1-methyl-3-oxo-1,3-dihydro-2,1-benzisothiazole-5-sulfonamide;
1-methyl-N-[3-(methylthio)phenyl]-3-oxo-1,3-dihydro-2,1-benzisothiazole-5-sulfonamide;

rel-N-[(1R,2R)-2-({[4-chloro-3-(trifluoromethyl)phenyl] sulfonyl}amino)cyclohexyl]-1-methyl-3-oxo-1,3-dihydro-2,1-benzisothiazole-5-sulfonamide;

rel-N-[(1R,2S)-2-({[4-chloro-3-(trifluoromethyl)phenyl] sulfonyl}amino)cyclohexyl]-1-methyl-3-oxo-1,3-dihydro-2,1-benzisothiazole-5-sulfonamide; and 1-methyl-3-oxo-N-{3-[(trifluoromethyl)thio]phenyl}-1,3-dihydro-2,1-benzisothiazole-5-sulfonamide.

12. A method of treating a disorder associated with chemokine receptor inhibition, which comprises administering to a mammal in need thereof, a pharmaceutical composition comprising a therapeutically effective amount of at least one compound of Formula I

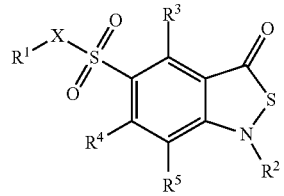

Formula I wherein:

R¹ is substituted or unsubstituted $C_{1-10}$ alkyl, substituted or unsubstituted heterocycle, substituted or unsubstituted $C_{3-10}$ cycloalkyl, substituted or unsubstituted $C_{3-10}$ cycloalkenyl or substituted or unsubstituted $C_{6-10}$ aryl;

R² is substituted or unsubstituted $C_{1-6}$ alkyl;

R³ is H, substituted or unsubstituted $C_{1-6}$ alkyl, halogen, substituted or unsubstituted —$OC_{1-3}$ alkyl, CN, NO₂, $C_{2-6}$ alkenyl, $C_{2-6}$ alkynyl, C(O)R⁶, NR⁷R⁸ or hydroxyl;

R⁴ is H, substituted or unsubstituted $C_{1-6}$ alkyl, halogen, substituted or unsubstituted —$OC_{1-3}$ alkyl, CN, NO₂, $C_{2-6}$ alkenyl, $C_{2-6}$ alkynyl, C(O)R⁶, NR⁷R⁸ or hydroxyl;

R⁵ is H, substituted or unsubstituted $C_{1-6}$ alkyl, halogen, substituted or unsubstituted —$OC_{1-3}$ alkyl, CN, NO₂, $C_{2-6}$ alkenyl, $C_{2-6}$ alkynyl, C(O)R⁶, NR⁷R⁸ or hydroxyl;

X is O, S or NH;

R⁶ is H or substituted or unsubstituted $C_{1-6}$ alkyl;

R⁷ is H or substituted or unsubstituted $C_{1-6}$ alkyl;

R⁸ is H or substituted or unsubstituted $C_{1-6}$ alkyl;

with the proviso that the compound of Formula I does not have one of the following structures:

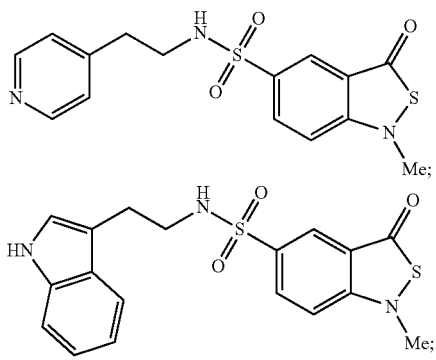

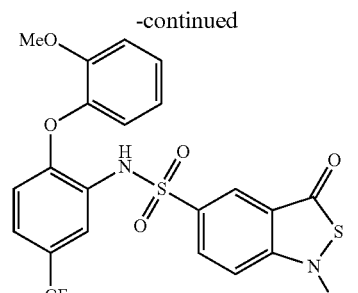

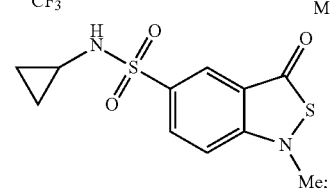

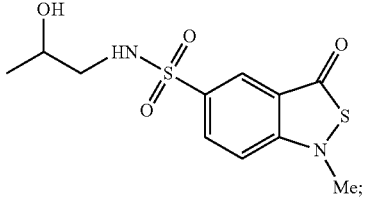

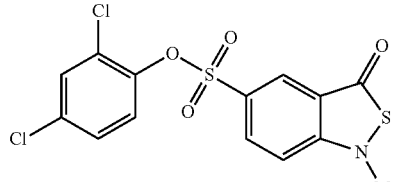

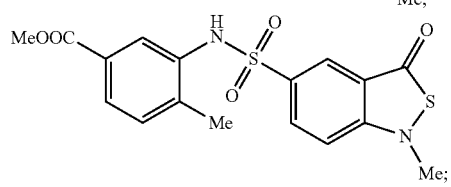

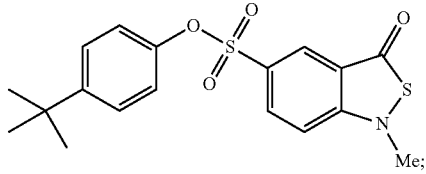

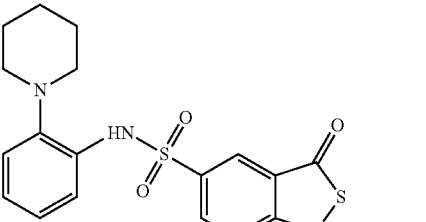

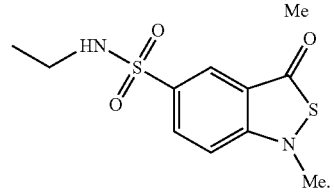

13. A method of claim 12, wherein the pharmaceutical composition is administered to the mammal to treat ocular inflammatory diseases including uveitis, dry eye, Keratitis, allergic eye disease, maculopathies, retinal degeneration, non-exudative age related macular degeneration, exudative age related macular degeneration, choroidal neovascularization, diabetic retinopathy, acute macular neuroretinopathy, central serous chorioretinopathy, cystoid macular edema, diabetic macular edema and retinitis.

14. The method of claim 13 wherein the mammal is a human.

\* \* \* \* \*

UNITED STATES PATENT AND TRADEMARK OFFICE
CERTIFICATE OF CORRECTION

| | | |
|---|---|---|
| PATENT NO. | : 8,524,745 B2 | Page 1 of 2 |
| APPLICATION NO. | : 13/710697 | |
| DATED | : September 3, 2013 | |
| INVENTOR(S) | : Haiqing Yuan et al. | |

It is certified that error appears in the above-identified patent and that said Letters Patent is hereby corrected as shown below:

Title Page, Item (56), under "Other Publications", in column 1, line 4, delete "pharmacaphore" and insert -- pharmacophore --, therefor.

Title Page, Item (56), under "Other Publications", in column 1, line 5, delete "realtionsip" and insert -- relationship --, therefor.

Title Page, Item (56), under "Other Publications", in column 1, line 6, delete "hormome" and insert -- hormone --, therefor.

In the Specification

In column 1, line 41, delete "atheroscelorsis" and insert -- atherosclerosis --, therefor.

In column 2, line 20, delete "maybe" and insert -- may be --, therefor.

In column 10, line 67, delete "(RY)" and insert -- (Ry) --, therefor.

In column 11, line 10, delete "Rx" and insert -- $R^x$ --, therefor.

In column 12, line 3, delete "phenylethyl2benzoate," and insert -- phenylethyl-2-benzoate, --, therefor.

In column 13, line 25, delete "2phenyl" and insert -- 2-phenyl --, therefor.

In column 17, line 26, delete ";amino" and insert -- ; amino --, therefor.

In column 17, line 54, delete "sulfonamide" and insert -- sulfonamide; --, therefor.

In column 19, line 40, delete "Stahal" and insert -- Stahl --, therefor.

In column 19, line 41, delete "Chemica" and insert -- Chimica --, therefor.

In column 19, line 49, delete ""Stahal" and insert -- Stahl --, therefor.

In column 19, line 50, delete "Chemica" and insert -- Chimica --, therefor.

In column 20, line 49, delete "vasuclar" and insert -- vascular --, therefor.

In column 21, line 1, delete "(PONS)," and insert -- (POHS), --, therefor.

Signed and Sealed this
Tenth Day of December, 2013

Margaret A. Focarino
*Commissioner for Patents of the United States Patent and Trademark Office*

CERTIFICATE OF CORRECTION (continued)
U.S. Pat. No. 8,524,745 B2

In column 21, line 9, delete "accosiated" and insert -- associated --, therefor.

In column 21, line 26, delete "pigement" and insert -- pigment --, therefor.

In column 21, line 55, delete "vasuclar" and insert -- vascular --, therefor.

In column 22, line 7, delete "(PONS)," and insert -- (POHS), --, therefor.

In column 22, line 15, delete "accosiated" and insert -- associated --, therefor.

In column 22, line 32, delete "pigement" and insert -- pigment --, therefor.

In column 25, line 33, delete "20%#30%" and insert -- 20%→30% --, therefor.

In column 26, line 24, delete "Substitutents" and insert -- Substituents --, therefor.

In column 28, line 11, delete "diasteroisomeric" and insert -- diastereoisomeric --, therefor.

In column 30, line 55, delete "catchol" and insert -- catechol --, therefor.

In column 72, line 39, delete "MuItiPROBE" and insert -- MultiPROBE --, therefor.

In columns 71-72, line 20, delete "methy1" and insert -- methyl --, therefor.

In columns 71-72, line 24, delete "benzodioxo1" and insert -- benzodioxol --, therefor.

In columns 73-74, line 39, delete "methy1" and insert -- methyl --, therefor.

In columns 73-74, line 42, delete "methy1" and insert -- methyl --, therefor.

In columns 73-74, line 48, delete "methy1" and insert -- methyl --, therefor.

In columns 73-74, line 54, delete "methy1" and insert -- methyl --, therefor.

In columns 75-76, line 37, delete "phenyl}1" and insert -- phenyl}-1 --, therefor.

In columns 75-76, line 45, delete "pheny1}" and insert -- phenyl} --, therefor.

In columns 75-76, line 57, delete "methy1" and insert -- methyl --, therefor.

In columns 75-76, line 75, delete "thienylsulfony1" and insert -- thienylsulfonyl --, therefor.

In columns 75-76, line 76, delete "yl+sulfonyl" and insert -- yl]sulfonyl --, therefor.

In columns 77-78, line 73, delete "methy1" and insert -- methyl --, therefor.

In columns 77-78, line 76, delete "methy1" and insert -- methyl --, therefor.

In the Claims

In column 88, line 35, in claim 9, ";amino" and insert -- amino --, therefor.

In column 93, line 23, in claim 11, delete ";amino" and insert -- amino --, therefor.